(12) United States Patent
Gu

(10) Patent No.: US 11,866,731 B2
(45) Date of Patent: Jan. 9, 2024

(54) MODIFIED IMMUNE CELLS AND USES THEREOF

(71) Applicant: CHINEO MEDICAL TECHNOLOGY CO., LTD., Beijing (CN)

(72) Inventor: Weiyue Gu, Beijing (CN)

(73) Assignee: CHINEO MEDICAL TECHNOLOGY CO., LTD, Beijing (CN)

(*) Notice: Subject to any disclaimer, the term of this patent is extended or adjusted under 35 U.S.C. 154(b) by 471 days.

(21) Appl. No.: 15/733,076

(22) PCT Filed: Nov. 12, 2018

(86) PCT No.: PCT/CN2018/115079
§ 371 (c)(1),
(2) Date: May 8, 2020

(87) PCT Pub. No.: WO2019/091478
PCT Pub. Date: May 16, 2019

(65) Prior Publication Data
US 2020/0354676 A1  Nov. 12, 2020

(30) Foreign Application Priority Data

Nov. 10, 2017 (CN) ............ 201711101450.X
Jan. 9, 2018 (CN) ............ 201810017770.5
Jan. 16, 2018 (CN) ............ 201810037682.1
Jun. 11, 2018 (WO) ............ PCT/CN2018/090638
Jul. 2, 2018 (WO) ............ PCT/CN2018/094126
Nov. 9, 2018 (WO) ............ PCT/CN2018/114897

(51) Int. Cl.
*A61P 35/00* (2006.01)
*A61K 35/17* (2015.01)
*C07K 16/30* (2006.01)
*C12N 15/86* (2006.01)
*C12N 5/0783* (2010.01)
*C07K 14/725* (2006.01)
*C07K 16/28* (2006.01)

(52) U.S. Cl.
CPC ............ *C12N 5/0636* (2013.01); *A61K 35/17* (2013.01); *A61P 35/00* (2018.01); *C07K 14/7051* (2013.01); *C07K 16/2803* (2013.01); *C07K 16/30* (2013.01); *C12N 15/86* (2013.01); *C07K 2319/02* (2013.01); *C07K 2319/03* (2013.01); *C12N 2740/15043* (2013.01)

(58) Field of Classification Search
CPC ...... C12N 5/0636; C12N 15/86; A61K 35/17; A61P 35/00; C07K 14/7051; C07K 16/2803; C07K 16/30; C07K 2319/02; C07K 2319/03
USPC .................................................. 424/93.21
See application file for complete search history.

(56) References Cited

FOREIGN PATENT DOCUMENTS

| CN | 103965361 A | 8/2014 |
|---|---|---|
| CN | 104946589 A | 9/2015 |
| CN | 105153315 A | 12/2015 |
| WO | 2013019615 A2 | 2/2013 |
| WO | 2016112195 A1 | 7/2016 |
| WO | 2016122738 A1 | 8/2016 |
| WO | 2016141357 A1 | 9/2016 |

OTHER PUBLICATIONS

Machine-translation of CN103965361A (pp. 1-27, Aug. 24, 2022).*
Machine-translation of CN105153315A (pp. 1-16, Aug. 24, 2022).*
International Search Report issued on International Application PCT/CN2018/115079, dated Feb. 22, 2019, 7 pages.
Liu, X., et al., "A Chimeric Switch-Receptor Targeting PD1 Augments the Efficacy of Second-Generation CAR T Cells in Advanced Solid Tumors", Cancer Research., Mar. 15, 2016, vol. 76, pp. 1578-1590, 14 pgs.
European Patent Application No. EP 18 87 7126, Supplemental European Search Report, dated Jul. 16, 2021, 33 pgs.
Moon, E.K., et al., "Bloackade of Programmed Death 1 Augments the Ability of Human T Cells Engineered to Target NY-ESO-1 to Control Tumor Growth after Adoptive Transfer" Clinical Cancer Research, vol. 22, No. 2, Jan. 15, 2016, 23 pgs.
Newick, Kheng, et al., "CAR T Cell Therapy for Solid Tumors", Annual Review of Medicine, Selected Topics in the Clinical Sciences [Online] vol. 68, No. 1, Jan. 14, 2017, pp. 139-152, 17 pgs.
Moon, E.K., et al., "Multifactorial T-Cell Hypofunction That is Reversible Can Limit the Efficacy of Chimeric Antigen Receptor-Transduced Human T-Cells in solid Tumors", Clinical Cancer Research, vol. 20, No. 16, Jun. 11, 2014, pp. 4262-4273, 13 pgs.

* cited by examiner

Primary Examiner — Yan Xiao
(74) Attorney, Agent, or Firm — Leber IP Law; Shelly M. Fujikawa

(57) ABSTRACT

Provided are modified immune cells including tumor infiltrating lymphocyte (TIL) or B cells, a composition comprising the immune cells, and a method of treating neoplastic or cancer conditions comprising administering to a subject the immune cells.

14 Claims, 24 Drawing Sheets

Specification includes a Sequence Listing.

| Dilution | 3 | 9 | 27 |
|---|---|---|---|
| FACS | | | |
| PD1+ % | 97.4% | 91.0% | 89.5% |
| Titer (TU/ml) | 2337600 | 6552000 | 19332000 |

| Dilution | 81 | 243 | 729 |
|---|---|---|---|
| FACS | | | |
| PD1+ % | 66.2% | 43.6% | 20.8% |
| Titer (TU/ml) | 42897600 | 84758400 | 121305600 |

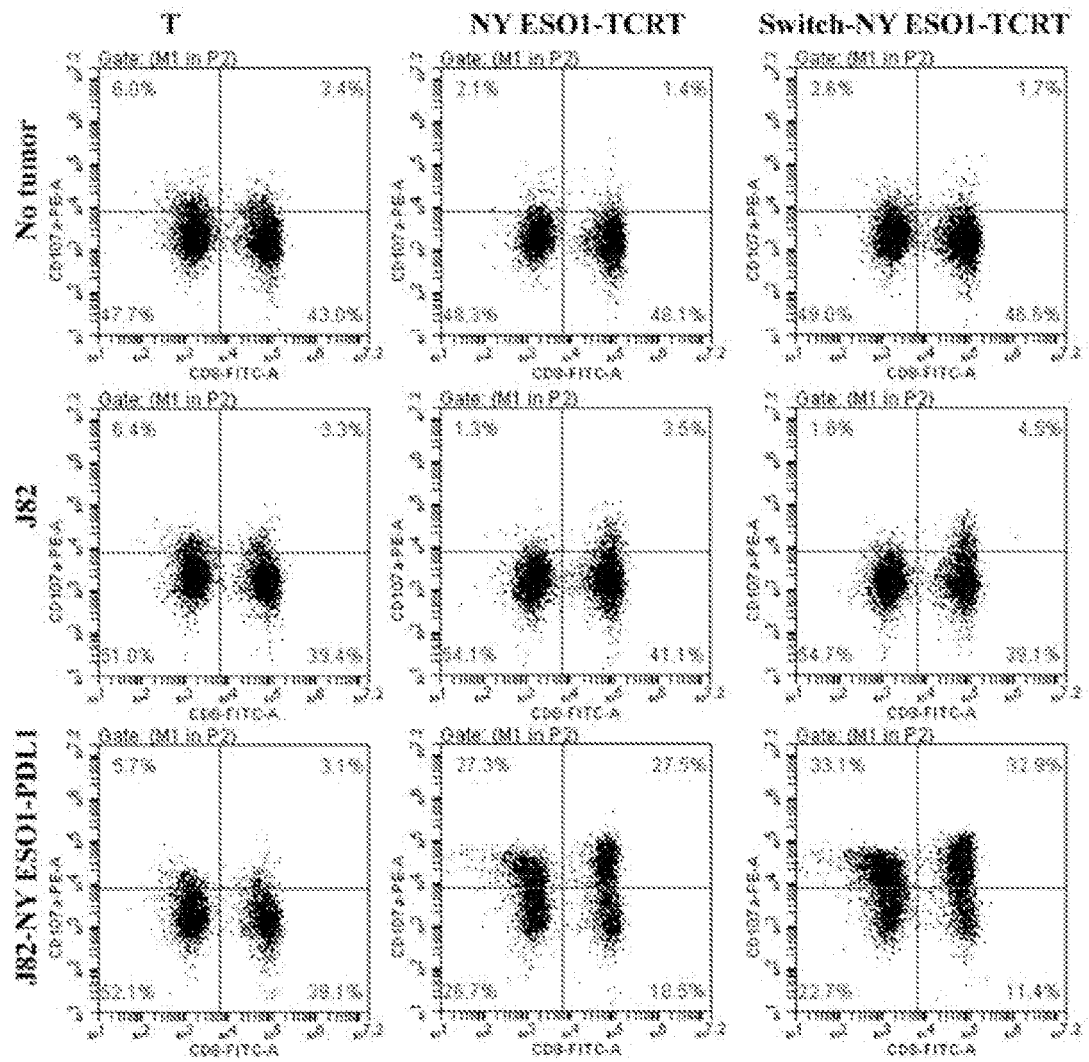
FIG. 6A
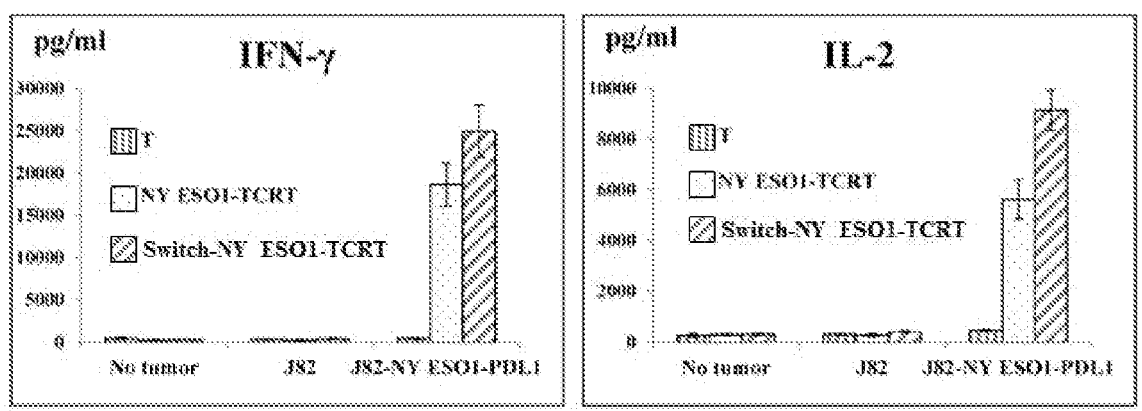
FIG. 6B
FIG. 6C

Liver new metastatic lesion

| Lesion No. | Lesion sites | D4 (Baseline) | D29 | D56 | D83 |
|---|---|---|---|---|---|
| 1 | Retroperitoneal lymph nodes (short diameter) | 24 mm | 20 mm | 19 mm | No progression |
| 2 | Liver metastasis (long diameter) | 11 mm | 19 mm | 23 mm | No progression |
| | Sum of target lesions | 35 mm | 39 mm | 42 mm | No progression |
| | | | Increased by 11% | Increased by 20% | |
| | New metastatic lesion or not | | no | yes | yes |
| | Assessment | | SD | PD | PD |

Abdominal wall subcutaneous metastatic lesion

Liver metastatic lesion

Spleen and stomach interstitial lymph nodes metastatic lesions

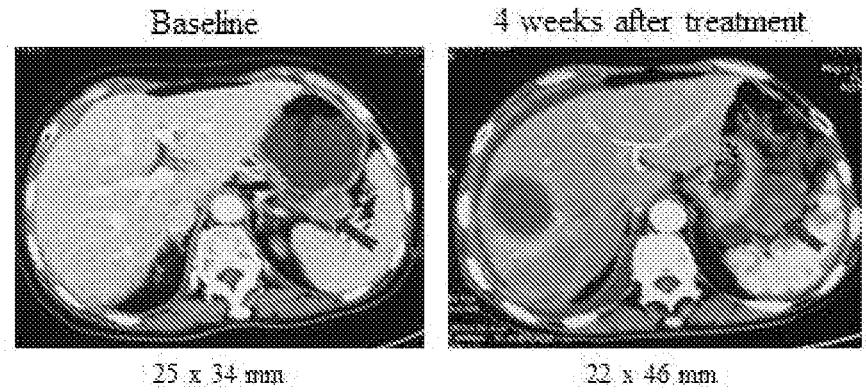

FIG. 22C

| Lesion No. | Lesion sites | Baseline | 4 weeks after treatment |
|---|---|---|---|
| 1 | Peritoneal subcutaneous (long diameter) | 52 mm | 37 mm |
| 2 | Liver metastasis (long diameter) | 71 mm | 72 mm |
| 3 | Spleen and stomach interstitial lymph nodes metastasis (short diameter) | 25 mm | 22 mm |
| | Sum of target lesions | 148 mm | 131 mm |
| | | | Decreased by 12% |
| | New metastatic lesion or not | | No |
| | Assessment | | SD |

FIG. 22D

Para-vascular lymph nodes

D3 Baseline   D 45

22 x 28 mm  7 x 13 mm

Retroperitoneal lymph nodes

D3 Baseline   D 45

22 x 28 mm  12 x 15 mm

Left inguinal lymph nodes

D3 Baseline — 23 x 34 mm
D 45 — 22 x 35 mm

| Lesion No. | Lesion sites | D3 (Baseline) | D 73 |
|---|---|---|---|
| 1 | Para-vascular lymph nodes (short diameter) | 22 mm | 7 mm |
| 2 | Retroperitoneal lymph nodes (short diameter) | 22 mm | 12 mm |
| 3 | Left inguinal lymph nodes (short diameter) | 23 mm | 22 mm |
| | Sum of target lesions | 67 mm | 41 mm |
| | | | Decreased by 37.9% |
| | New metastatic lesion or not | | No |
| | Assessment | | PR |

Left lung metastasis lesions
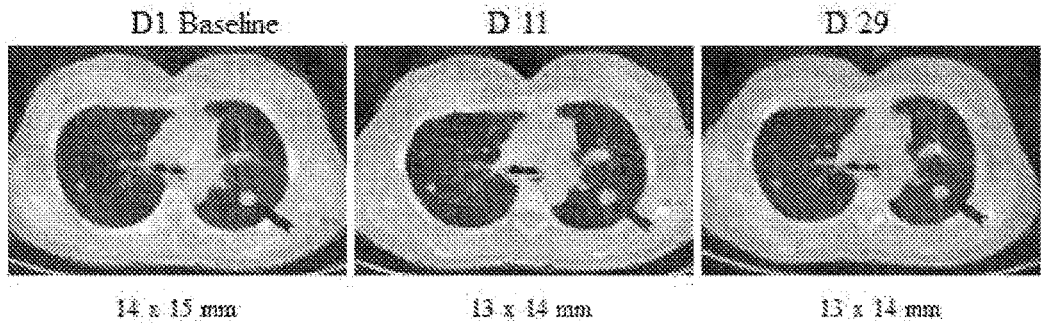
FIG. 24A
Right lung metastasis lesions
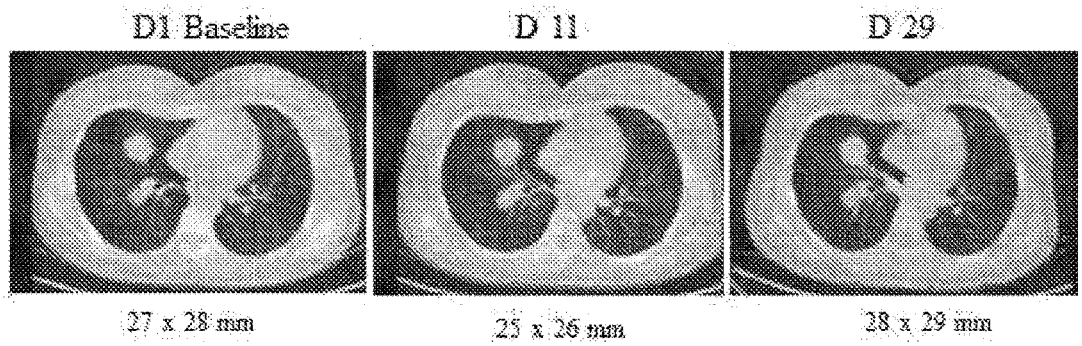
FIG. 24B
| Lesion No. | Lesion sites | D1 (Baseline) | D 11 | D 29 |
|---|---|---|---|---|
| 1 | Left lung metastasis (long diameter) | 15 mm | 14 mm | 14 mm |
| 2 | Right lung metastases (long diameter) | 28 mm | 26 mm | 29 mm |
| | Sum of target lesions | 43 mm | 40 mm | 43 mm |
| | | | Decreased by 7% | No change |
| | New metastatic lesion or not | | No | No |
| | Assessment | | SD | SD |
FIG. 24C

MODIFIED IMMUNE CELLS AND USES THEREOF

CROSS-REFERENCE

This application is a national phase entry of International Patent Application No. PCT/CN2018/1115079, filed Nov. 12, 2018, which claims priority from CN Patent Application No. 201711101450.X filed on Nov. 10, 2017, CN Patent Application No. 201810017770.5 filed on Jan. 9, 2018, CN Patent Application No. 201810037682.1 filed on Jan. 16, 2018, PCT International Application No. PCT/CN2018/090638 filed on Jun. 11, 2018, PCT International Application No. PCT/CN2018/094126 filed on Jul. 2, 2018 and PCT International Application No. PCT/CN2018/114897 filed on Nov. 9, 2018, the entire disclosures of which are incorporated herein by reference.

INCORPORATION BY REFERENCE OF MATERIAL IN ASCII TEXT FILE

This application incorporates by reference the Sequence Listing contained in the following file:
a) File name: 0291-001US1_20201006_Sequence_Listing.txt; created Oct. 6, 2020, 10 KB in size.

BACKGROUND

Immunotherapy can involve modifying a patient's own immune cells to redirect cellular cytotoxicity to cells of interest, for example tumor cells. Modified immune cells, such as T cells, expressing chimeric antigen receptors (CAR) can utilize endogenous immune cell signaling for immune cell cytotoxicity.

Conventional methods of immunotherapy suffer from various deficiencies. Such deficiencies include insufficient signaling from co-stimulatory receptors for persistent and/or adequate immune responses for therapeutic effects, inadequate specificity of modified immune cells for diseased cells such as cancer cells (e.g., on-target off-tumor effects and toxicities), and activation of immunosuppressive mechanisms, all of which can minimize the effect of immune responses.

SUMMARY

In view of the foregoing, there exists a considerable need for alternative systems and methods to carry out immunotherapy. The compositions and methods of the present disclosure address this need, and provide additional advantages as well. In particular, the various aspects of the disclosure provide compositions and methods for eliciting an immune cell activation signal via signaling through binding a ligand that would normally illicit an immune cell inactivation signal. The compositions and methods may also elicit an immune cell activation signal via binding a B cell surface protein.

In an aspect, the present disclosure provides a modified immune cell that specifically binds to a tumor antigen, the modified immune cell comprising a chimeric stimulating molecule, wherein the chimeric stimulating molecule comprises: an extracellular domain (ECD) of a protein that, in an unmodified immune cell, elicits an immune cell inactivation signal upon binding to its ligand, wherein the ECD is fused to an intracellular domain (ICD) of a co-stimulatory molecule that mediates an immune cell activation signal, wherein binding of the chimeric stimulating molecule to the ligand yields the immune cell activation signal in the modified immune cell instead of the immune cell inactivation signal.

In some embodiments, the modified immune cell is a tumor infiltrating lymphocyte (TIL), wherein optionally, the TIL may express at least one of PD-1, CD137, and TIM-3.

In an aspect, the present disclosure provides a modified T cell that specifically binds to a neoantigen, the modified T cell comprising a switch molecule, wherein the switch molecule comprises: an extracellular domain (ECD) of a protein that, in an unmodified T cell, elicits an immune cell activation signal upon binding to its ligand, wherein the ECD is fused to an intracellular domain (ICD) of a co-stimulatory molecule that mediates an immune cell activation signal, wherein binding of the switch molecule to the ligand yields the immune cell activation signal in the modified T cell instead of the immune cell inactivation signal.

In some embodiments, the T cell may comprise a T cell receptor (TCR) complex which exhibits specific binding to the neoantigen. In some embodiments, the TCR complex may be an endogenous TCR complex. In some embodiments, the TCR complex may be an exogenous TCR complex.

In some embodiments, the neoantigen may comprise a peptide fragment of a protein encoded by a mutated gene, wherein the gene is selected from ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT. In some embodiments, the neoantigen may comprise a peptide fragment of a protein encoded by a mutated gene, wherein the gene is selected from JAK2, KRAS, BRAF, TP53, PIK3CA, EGFR, IDH1, NRAS, CTNNB1, NPM1, CALR, FGFR3, CDKN2A, KIT, MYD88, APC, HRAS, MED12, DNMT3A, GNAS, IDH2, KCNJ5, PTEN, NOTCH1, SF3B1, FLT3, ASXL1, SRSF2, FOXL2, PTPN11, GNAQ, RET, HLA-A, MPL, IKZF1, KMT2C, TET2, PDGFRA, FBXW7, H3F3A, ALK, CEBPA, ESR1, AKT1, RUNX1, GNA11, VHL, WT1, U2AF1, ABL1, ERBB2, DICER1, NOTCH4, EZH2, HNF1A, SMARCB1, CXCR4, PLCG1, TSHR, PRKACA, RHOA, STAT3, POLE, SETBP1, MET, AR, STK11, NF2, CBL, HLA-B, PRKCB, ATR, PPP2R1A, CASC5, CD79B, PBRM1, PTK2B, GATA2, KMT2D, SULT1A1, FLNB, PRPF8, RNF43, MSH6, FGFR2, SMAD4, JAK3, USP8, DLC1, ESRP1, LRP1B, MYH11, BRCA1, CARD11, HSP90AB1, MAP3K9, ADAMTSL3, PDGFRB, RPTOR, ROS1, NFKBIE, AMER1, KLF4, RAC1, TERT, MYOD1, ATP1A1, CSF3R, NOTCH2, CCR4, PAX5, SPTAN1, MLH1, CUBN, RNF213, SMO, ABCC4, AXIN2, CSF1R, PER1, PKHD1, IL7R, RB1, ARID1A, ATM, FES, MTHFR, PTCH2, FANCI, CDH5, CIC, IL6ST, MYH9, NF1, TGFBR2, INSR, PTPN12, TNFAIP3, MEN1, NSD1, SLITRK6, SYT1, TNKS, CCND3, PSMD13, CYP2D6, HELQ, LPHN3, PRAME, STAT5B, BCL6, CCDC6, CCND1, FLCN, LMO2, MUC1, NFKBIZ, NRP2, CTCF, HIST1H3B, KEAP1, SLC22A2, ABCC2, EED, GATA1, GLI3, IKZF3, PIK3CG, XPO1, CHRNA3, MAP2K1, SETD2, ZNF668, CCND2, FLT4, NT5C2, RECQL4, SSX1, ALOX12B, CDKN1B, ELF3, INPP4B, MARVELD3, MLLT4, MLPH, NTRK3, SPOP, BCL2, EPHB1, ERCC4, ERCC6, ETNK1, JAK1, LRP2, MUTYH, NFKBIA, ARNT, BRCA2, and CDH2.

In some embodiments, the neoantigen may be selected based on a genetic profile of a tumor sample from an individual. In some embodiments, the neoantigen may be selected based on a somatic mutation profile of a tumor sample from an individual.

In some embodiments, the protein that, in an unmodified TIL or an unmodified T cell, elicits an immune cell inactivation signal upon binding to its ligand may be a signaling receptor. In some embodiments, the protein that, in an unmodified TIL or an unmodified T cell, elicits an immune cell inactivation signal upon binding to its ligand may be a checkpoint receptor, a cytokine receptor, a chemokine receptor, a growth factor receptor, or a hormone receptor. In some embodiments, the protein that, in an unmodified TIL or an unmodified T cell, elicits an immune cell inactivation signal upon binding to its ligand may be selected from the group consisting of transforming growth factor-beta receptor (TGF-beta-R), programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and TIGIT.

In some embodiments, the co-stimulatory molecule may be interleukin-2 receptor (IL-2R), interleukin-12 receptor (IL-12R), CD2, CD3, CD4, CD7, CD8, CD27, CD28, CD30, CD40, 4-1BB/CD137, ICOS, lymphocyte function-associated antigen-1 (LFA-1), LIGHT, NKG2C, or OX40.

In some embodiments, the immune cell activation signal may be mediated by an activation factor. In some embodiments, the activation factor is a soluble cytokine, a soluble chemokine, or a growth factor. In some embodiments, the activation factor is a soluble cytokine, and wherein the soluble cytokine is IL-1, IL-2, IL-6, IL-7, IL-8, IL-10, IL-12, IL-15, IL-21, TNF, TGF, IFN, or any functional fragment or variant thereof. In some embodiments, the immune cell activation signal may comprise a clonal expansion of the modified TIL or modified T cell; cytokine release by the modified TIL or modified T cell; cytotoxicity of the modified TIL or modified T cell; proliferation of the modified TIL or modified T cell; differentiation, dedifferentiation or transdifferentiation of the modified TIL or modified T cell; movement and/or trafficking of the modified TIL or modified T cell; exhaustion and/or reactivation of the modified TIL or modified T cell; and release of other intercellular molecules, metabolites, chemical compounds, or combinations thereof by the modified TIL or modified T cell.

In some embodiments, upon binding of the switch molecule to the ligand, the modified TIL or modified T cell may exhibit enhanced neoantigen binding as compared to an unmodified TIL or an unmodified T cell.

In some embodiments, the modified TIL or modified T cell may exhibit increased cytotoxicity against a target cell as compared to an unmodified TIL or an unmodified T cell, when the switch molecule binds to the ligand and the modified TIL or modified T cell binds to the neoantigen present on the target cell.

In some embodiments, the modified TIL or modified T cell may exhibit increased cytokine secretion as compared to an unmodified TIL or an unmodified T cell, when the switch molecule binds the ligand and the modified TIL or modified T cell binds to the neoantigen present on a target cell. In some embodiments, the cytokine may be IFN-gamma or IL-2.

In an aspect, the present disclosure provides a modified immune cell comprising a chimeric antigen receptor (CAR) and a T cell receptor (TCR) complex which exhibits specific binding to a neoantigen, wherein the CAR comprises: (a) an antigen interacting domain capable of binding a B cell surface protein; (b) a transmembrane domain; and (c) an intracellular signaling domain.

In some embodiments, the immune cell may be a tumor infiltrating lymphocyte (TIL). In some embodiments, the TIL may be a triple positive T cell expressing PD-1, CD137, and TIM-3. In some embodiments, the TCR complex which exhibits specific binding to a neoantigen may be an endogenous TCR complex. In some embodiments, the TCR complex which exhibits specific binding to a neoantigen may be an exogenous TCR complex.

In some embodiments, the neoantigen may comprise a peptide fragment of a protein encoded by a mutated gene, wherein the gene is selected from ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 1B, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, PAGE2, PAGE5, PDG-FRα, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT.

In some embodiments, the neoantigen may be selected based on a genetic profile of a tumor sample from an individual. In some embodiments, the neoantigen may be selected based on a somatic mutation profile of a tumor sample from an individual.

In some embodiments, the B cell surface protein is selected from CD19, CD20, and CD22.

In some embodiments, the intracellular signaling domain may comprise an immunoreceptor tyrosine-based activation motif (ITAM). In some embodiments, the intracellular signaling domain may comprise an immunoreceptor tyrosine-based inhibition motif (ITIM). In some embodiments, the intracellular signaling domain may comprise an intracellular domain of a molecule selected from: an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MHC complex, NFAT, NF-κB, PLC-γ, iC3b, C3dg, C3d, and Zap70.

In some embodiments, the intracellular signaling domain may comprise an intracellular domain of CD3 ζ. In some embodiments, the intracellular domain of CD3 ζ may comprise an ITAM. In some embodiments, the CAR may further comprise a co-stimulatory domain. In some embodiments, the co-stimulatory domain may comprise a signaling domain of a MHC class I molecule, a TNF receptor protein, an immunoglobulin-like protein, a cytokine receptor, an integrin, a signaling lymphocytic activation molecule (SLAM protein), an activating NK cell receptor, or a Toll ligand receptor.

In some embodiments, the co-stimulatory domain may comprise a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4 β1, Integrin α4 β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6.

In some embodiments, upon contacting the immune cell to the B cell surface protein, the immune cell may exhibit enhanced proliferation as compared to an unmodified immune cell. In some embodiments, the enhanced proliferation may be ascertained in vitro. In some embodiments, the enhanced proliferation may be ascertained in vivo. In some embodiments, the immune cell may exhibit at least a 2-fold increase in proliferation after at least about 24, 48, or 96 hours after the contacting, as compared to an unmodified immune cell.

In an aspect, the present disclosure provides a modified tumor infiltrating lymphocyte (TIL) that specifically binds to a neoantigen, wherein the modified TIL comprises: (a) a switch molecule comprising an extracellular domain (ECD) of a protein that, in an unmodified TIL, elicits an immune cell inactivation signal upon binding to its ligand, wherein the ECD is fused to an intracellular domain (ICD) of co-stimulatory molecule that mediates an immune cell activation signal, and wherein binding of the switch molecule to the ligand yields the immune cell activation signal instead of the immune cell inactivation signal in the modified TIL, and (b) a chimeric antigen receptor comprising (i) an antigen interacting domain capable of binding a B cell surface protein; (ii) a transmembrane domain; and (iii) an intracellular signaling domain.

In an aspect, the present disclosure provides a modified immune cell that specifically binds to a neoantigen, wherein the modified immune cell comprises: (a) a switch molecule comprising an extracellular domain (ECD) of a protein that, in a unmodified immune cell, elicits an immune cell inactivation signal upon binding to its ligand, wherein the ECD is fused to an intracellular domain (ICD) of co-stimulatory molecule that mediates an immune cell activation signal, and wherein binding of the switch molecule to the ligand yields an immune cell activation signal instead of the immune cell inactivation signal in the modified immune cell, and (b) a chimeric antigen receptor comprising (i) an antigen interacting domain capable of binding a B cell surface protein; (ii) a transmembrane domain; and (iii) an intracellular signaling domain.

In some embodiments, the immune cell may comprise a T cell receptor (TCR) complex exhibiting specific binding to a neoantigen. In some embodiments, the TCR complex may be an endogenous TCR complex. In some embodiments, the TCR complex is an exogenous TCR complex.

In some embodiments, the neoantigen comprises a peptide fragment of a protein encoded by a mutated gene, wherein the gene is selected from ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT.

In some embodiments, the neoantigen may be selected based on a genetic profile of a tumor sample from an individual. In some embodiments, the neoantigen may be selected based on a somatic mutation profile of a tumor sample from an individual.

In some embodiments, the protein that, in an unmodified TIL or an unmodified immune cell, elicits an immune cell inactivation signal upon binding to its ligand may be a signaling receptor. In some embodiments, the protein that, in an unmodified TIL or an unmodified immune cell, elicits an immune cell inactivation signal upon binding to its ligand may be a checkpoint receptor, a cytokine receptor, a chemokine receptor, a growth factor receptor, or a hormone receptor. In some embodiments, the protein that, in an unmodified TIL or an unmodified immune cell, elicits an immune cell inactivation signal upon binding to its ligand may be selected from transforming growth factor-beta receptor (TGF-beta-R), programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and TIGIT.

In some embodiments, the co-stimulatory molecule may be interleukin-2 receptor (IL-2R), interleukin-12 receptor (IL-12R), CD2, CD3, CD4, CD7, CD8, CD27, CD28, CD30, CD40, 4-1BB/CD137, ICOS, lymphocyte function-associated antigen-1 (LFA-1), LIGHT, NKG2C, or OX40.

In some embodiments, the immune cell activation signal may be mediated by an activation factor. In some embodiments, the activation factor may be a soluble cytokine, a soluble chemokine, or a growth factor. In some embodiments, the activation factor may be a soluble cytokine, and wherein the soluble cytokine is IL-1, IL-2, IL-6, IL-7, IL-8, IL-10, IL-12, IL-15, IL-21, TNF, TGF, IFN, or any functional fragment or variant thereof.

In some embodiments, the immune cell activation signal may comprise a clonal expansion of the modified TIL or modified immune cell; cytokine release by the modified TIL or modified immune cell; cytotoxicity of the modified TIL or modified immune cell; proliferation of the modified TIL or modified immune cell; differentiation, dedifferentiation or transdifferentiation of the modified TIL or modified immune cell; movement and/or trafficking of the modified TIL or modified immune cell; exhaustion and/or reactivation of the modified TIL or modified immune cell; and release of other intercellular molecules, metabolites, chemical compounds, or combinations thereof by the modified TIL or modified immune cell.

In some embodiments, the B cell surface protein may be selected from CD19, CD20, and CD22.

In some embodiments, the intracellular signaling domain may comprise an immunoreceptor tyrosine-based activation motif (ITAM). In some embodiments, the intracellular signaling domain may comprise an immunoreceptor tyrosine-based inhibition motif (ITIM). In some embodiments, the intracellular signaling domain may comprise an intracellular domain of a molecule selected from: an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MHC complex, NFAT, NF-κB, PLC-γ, iC3b, C3dg, C3d, and Zap70.

In some embodiments, the intracellular signaling domain may comprise an intracellular domain of CD3 ζ. In some embodiments, the intracellular domain of CD3 ζ may comprise an ITAM. In some embodiments, the CAR may further comprise a co-stimulatory domain. In some embodiments, the co-stimulatory domain may comprise a signaling domain of a MHC class I molecule, a TNF receptor protein, an immunoglobulin-like protein, a cytokine receptor, an integrin, a signaling lymphocytic activation molecule (SLAM protein), an activating NK cell receptor, or a Toll ligand receptor.

In some embodiments, the co-stimulatory domain may comprise a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4 β1, Integrin α4 β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6.

In some embodiments, upon binding of the switch molecule to the ligand, the modified TIL or modified immune cell may exhibit enhanced neoantigen binding as compared to an unmodified TIL or an unmodified immune cell.

In some embodiments, the modified TIL or modified T cell may exhibit increased cytotoxicity against a target cell as compared to an unmodified TIL or an unmodified T cell, when the switch molecule binds to the ligand and the modified TIL or modified immune cell binds to the neoantigen present on the target cell.

In some embodiments, the modified TIL or modified immune cell may exhibit increased cytokine secretion as compared to an unmodified TIL or an unmodified immune cell, when the switch molecule binds the ligand and the modified TIL or modified immune cell binds to the neoantigen present on a target cell. In some embodiments, the cytokine may be IFN-gamma or IL-2.

In an aspect, the present disclosure provides a method of treating a cancer of a subject, comprising: (a) administering to a subject a modified TIL, modified T cell, or a modified immune cell of any one of the preceding claims; and (b) contacting the target cell of the cancer expressing a neoantigen with the modified TIL, modified T cell, or modified immune cell under conditions that induces cytotoxicity of the modified TIL, modified T cell, or modified immune cell against the target cell of the cancer, thereby inducing death of the target cell of the cancer.

In an aspect, the present disclosure provides a method of expanding a T cell population, the method comprising: (a) providing a population of T cells comprising at least a modified immune cell of any one of claims 21-40; and (b) exposing the population of T cells with the B-cell surface protein to effect expansion of the population of T cells. In some embodiments, the population of T cells may be exposed to a B cell comprising the B-cell surface protein.

In an aspect, the present disclosure provides a method of expanding a T cell population, comprising: (a) introducing a nucleic acid encoding a chimeric antigen receptor (CAR) into the T cell population, thereby producing a first CAR-expressing cell population, wherein the CAR comprises (i) an antigen interacting domain capable of binding a B cell surface protein; (ii) a transmembrane domain; and (iii) an intracellular signaling domain; and (b) contacting the first CAR-expressing cell population with a B cell surface protein, thereby producing an expanded and/or activated immune cell population.

In an aspect, the present disclosure provides a composition comprising one or more polynucleotides that encodes one or more of: (a) a switch molecule, wherein the switch molecule comprises an extracellular domain (ECD) of a protein that, in a unmodified immune cell, elicits an immune inactivation signal upon binding to its ligand, wherein the ECD is fused to an intracellular domain (ICD) of co-stimulatory protein that mediates an immune cell activation signal; and (b) an antigen specific T cell receptor complex, or one or more components thereof.

Another aspect of the present disclosure provides a composition comprising one or more polynucleotides that encodes one or more of: (a) an antigen specific T cell receptor complex, or one or more components thereof; and (b) a chimeric antigen receptor comprising (i) an antigen interacting domain capable of binding a B cell surface protein; (ii) a transmembrane domain; and (iii) an intracellular signaling domain. In some embodiments, the antigen specific T cell receptor complex may bind a neoantigen.

In some embodiments, the neoantigen may comprise a peptide fragment of a protein encoded by a mutated gene, wherein the gene is selected from ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT.

In some embodiments, the protein that, in an unmodified TIL or an unmodified T cell, elicits an immune cell inactivation signal upon binding to its ligand may be a signaling receptor. In some embodiments, the protein may be a checkpoint receptor, a cytokine receptor, a chemokine receptor, a growth factor receptor, or a hormone receptor. In some embodiments, the protein may be selected from the group consisting of transforming growth factor-beta receptor (TGF-beta-R), programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and TIGIT.

In some embodiments, the co-stimulatory protein that mediates an immune cell activations signal may be interleukin-2 receptor (IL-2R), interleukin-12 receptor (IL-12R), CD2, CD3, CD4, CD7, CD8, CD27, CD28, CD30, CD40, 4-1BB/CD137, ICOS, lymphocyte function-associated antigen-1 (LFA-1), LIGHT, NKG2C, OR OX40.

In some embodiments, the B cell surface protein may be selected from CD19, CD20, and CD22. In some embodiments, the intracellular signaling domain may comprise an intracellular domain of a molecule selected from: an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 q, DAP10, DAP12, FYN, LAT, Lck, MAPK, MHC complex, NFAT, NF-κB, PLC-γ, iC3b, C3dg, C3d, and Zap70.

In some embodiments, the chimeric antigen receptor may further comprise a co-stimulatory domain. In some embodiments, the co-stimulatory domain may comprise a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4 β1, Integrin α4 β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6.

In an aspect, the present disclosure provides a composition comprising one or more polynucleotides that encodes one or more of: (a) a switch molecule, wherein the switch molecule comprises an extracellular domain (ECD) of a protein that, in a unmodified immune cell, elicits an immune inactivation signal upon binding to its ligand, wherein the ECD is fused to an intracellular domain (ICD) of co-stimulatory protein that mediates an immune cell activation signal; (b) an antigen specific T cell receptor complex, or one or more components thereof; and (c) a chimeric antigen receptor comprising (i) an antigen interacting domain capable of binding a B cell surface protein; (ii) a transmembrane domain; and (iii) an intracellular signaling domain.

In an aspect, the present disclosure provides a modified tumor infiltrating lymphocyte (TIL) that specifically binds to a neoantigen, the modified TIL comprising a chimeric stimulating molecule, wherein the chimeric stimulating molecule comprises: a polypeptide extracellular domain (PED) that binds to the neoantigen, wherein the PED is fused to an intracellular domain (ICD) of a co-stimulatory molecule that mediates an immune cell activation signal, wherein binding of the chimeric stimulating molecule to the neoantigen yields the immune cell activation signal in the modified TIL.

In an aspect, the present disclosure provides modified immune cell comprising: (a) a switch molecule comprising an extracellular domain (ECD) of a protein that, in a unmodified immune cell, elicits an immune cell inactivation signal upon binding to its ligand, wherein said ECD is fused to an intracellular domain (ICD) of co-stimulatory molecule that mediates an immune cell activation signal, and wherein binding of the switch molecule to the ligand yields an immune cell activation signal instead of said immune cell inactivation signal in said modified immune cell, and (b) a chimeric antigen receptor (CAR) comprising (i) an antigen interacting domain capable of binding a B cell surface protein; (ii) a transmembrane domain; and (iii) an intracellular signaling domain.

In some embodiments, the modified immune cell may express at least one of PD1, CD137, and TIM3. In some embodiments, the immune cell may be obtained from a tumor. In some embodiments, the immune cell may be obtained from peripheral blood mononuclear cells. In some embodiments, the immune cell may comprise an endogenous TCR complex. In some embodiments, the immune cell may comprise an exogenous TCR complex. In some embodiments, the TCR complex may bind to a tumor cell. In some embodiments, the TCR complex may bind to a neoantigen. In some embodiments, the protein that in an unmodified immune cell, elicits an immune cell inactivation signal upon binding to its ligand may be a signaling receptor. In some embodiments, said protein that, in an unmodified immune cell, elicits an immune cell inactivation signal upon binding to its ligand may be a checkpoint receptor, a cytokine receptor, a chemokine receptor, a growth factor receptor, or a hormone receptor. In some embodiments, said protein that, in an unmodified immune cell, elicits an immune cell inactivation signal upon binding to its ligand may be selected from the group consisting of transforming growth factor-beta receptor (TGF-beta-R), programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and TIGIT. In some embodiments, said co-stimulatory molecule may be interleukin-2 receptor (IL-2R), interleukin-12 receptor (IL-12R), CD2, CD3, CD4, CD7, CD8, CD27, CD28, CD30, CD40, 4-1BB/CD137, ICOS, lymphocyte function-associated antigen-1 (LFA-1), LIGHT, NKG2C, or OX40. In some embodiments, said immune cell activation signal may be mediated by an activation factor. In some embodiments, the activation factor may be a soluble cytokine, a soluble chemokine, or a growth factor. In some embodiments, said activation factor may be a soluble cytokine, and wherein said soluble cytokine is IL-1, IL-2, IL-6, IL-7, IL-8, IL-10, IL-12, IL-15, IL-21, TNF, TGF, IFN, or any functional fragment or variant thereof. In some embodiments, said immune cell activation signal may comprise a clonal expansion of the modified immune cell; cytokine release by the modified immune cell; cytotoxicity of the modified immune cell; proliferation of the modified immune cell; differentiation, dedifferentiation or transdifferentiation of the modified immune cell; movement and/or trafficking of the modified immune cell; exhaustion and/or reactivation of the modified immune cell; and release of other intercellular molecules, metabolites, chemical compounds, or combinations thereof by the modified immune cell. In some embodiments, said B cell surface protein may be selected from CD19, CD20, and CD22. In some embodiments, said intracellular signaling domain may comprise an immunoreceptor tyrosine-based activation motif (ITAM). In some embodiments, said intracellular signaling domain may comprise an immunoreceptor tyrosine-based inhibition motif (ITIM). In some embodiments, said intracellular signaling domain may comprise an intracellular domain of a molecule selected from: an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MHC complex, NFAT, NF-κB, PLC-γ, iC3b, C3dg, C3d, and Zap70. In some embodiments, said intracellular signaling domain may comprise an intracellular domain of CD3 ζ. In some embodiments, said intracellular domain of CD3 ζ may comprise an ITAM. In some embodiments, said CAR further may comprise a co-stimulatory domain. In some embodiments, the co-stimulatory domain may comprise a signaling domain of a MHC class I molecule, a TNF receptor protein, an immunoglobulin-like protein, a cytokine receptor, an integrin, a signaling lymphocytic activation molecule (SLAM protein), an activating NK cell receptor, or a Toll ligand receptor. In some embodiments, the co-stimulatory domain may comprise a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4 β1, Integrin α407/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6. In some embodiments, upon contacting said immune cell to said B cell surface protein, said immune cell may exhibit enhanced proliferation as compared to an unmodified immune cell. In some embodiments, said enhanced proliferation may be ascertained in vitro. In some embodiments, said enhanced proliferation may be ascertained in vivo. In some embodiments, said immune cell may exhibit at least a 2-fold increase in proliferation after at least about 24, 48, or 96 hours after said contacting, as compared to an unmodified immune cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A-6C illustrates the expression of CD107a (a) and the release of IFN-γ (b) and IL-2 (c) in the T cells cultured with tumor cells, in an in vitro assay of NY-ESO-1 targeting TCR-T cells expressing PD1/CD28 switch molecule.

FIGS. 22A-D are tumor image analysis for Subjects 1-4.
FIGS. 24A-C are tumor image analysis for Subjects 1-4.

DETAILED DESCRIPTION

Figure 1:
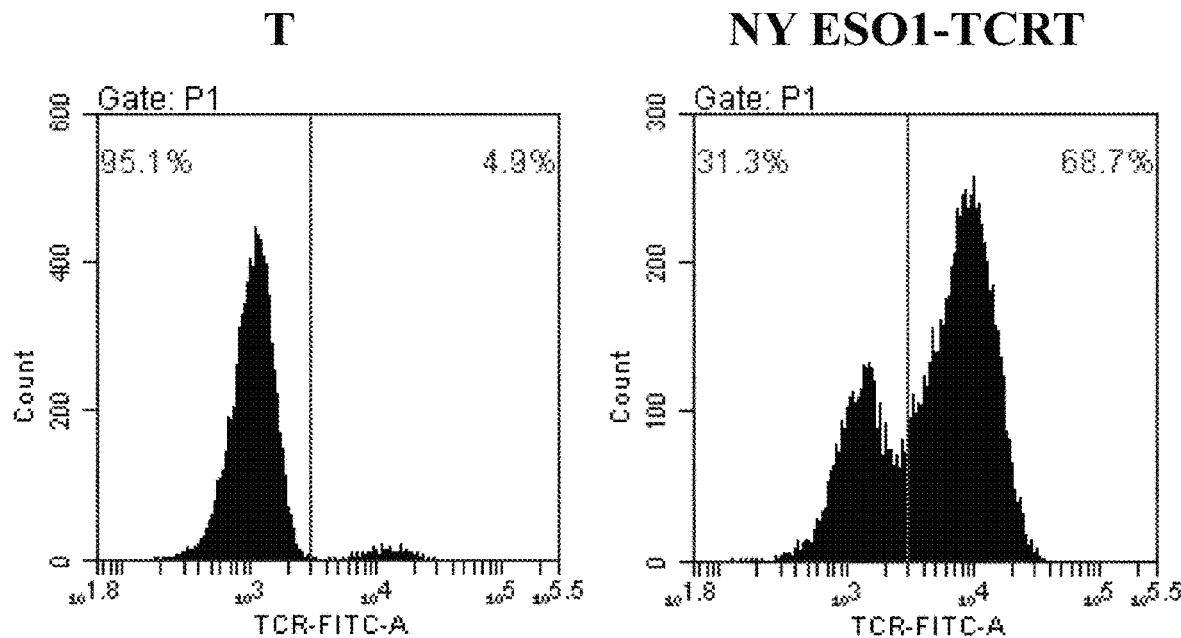
FIG. 1 illustrates T cell receptor (TCR) expression of T cells with or without transduction of the NY-ESO-1 TCR gene.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

As used in the specification and claims, the singular forms "a," "an," and "the" include plural references unless the context clearly dictates otherwise. For example, the term "a switch molecule" includes a plurality of switch molecules.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g. a cell can be a synthetically made, sometimes termed an artificial cell).

The term "antigen," as used herein, refers to a molecule or fragment thereof capable of being bound by a selective binding agent. As an example, an antigen can be a ligand that can be bound by a selective binding agent such as a receptor. As another example, an antigen can be an antigenic molecule that can be bound by a selective binding agent such as an immunological protein (e.g., an antibody). An antigen can also refer to a molecule or fragment thereof capable of being used in an animal to produce antibodies capable of binding to that antigen.

The term "neoantigen," as used herein, generally refers to tumor-specific antigens arising from mutations in a gene.

The resulting mutated proteins, or fragments thereof, can trigger an antitumor T cell response.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The term "antibody," as used herein, refers to a proteinaceous binding molecule with immunoglobulin-like functions. The term antibody includes antibodies (e.g., monoclonal and polyclonal antibodies), as well as derivatives, variants, and fragments thereof. Antibodies include, but are not limited to, immunoglobulins (Ig's) of different classes (i.e. IgA, IgG, IgM, IgD and IgE) and subclasses (such as IgG1, IgG2, etc.). A derivative, variant or fragment thereof can refer to a functional derivative or fragment which retains the binding specificity (e.g., complete and/or partial) of the corresponding antibody. Antigen-binding fragments include Fab, Fab', F(ab')$_2$, variable fragment (Fv), single chain variable fragment (scFv), minibodies, diabodies, and single-domain antibodies ("sdAb" or "nanobodies" or "camelids"). The term antibody includes antibodies and antigen-binding fragments of antibodies that have been optimized, engineered or chemically conjugated. Examples of antibodies that have been optimized include affinity-matured antibodies. Examples of antibodies that have been engineered include Fc optimized antibodies (e.g., antibodies optimized in the fragment crystallizable region) and multispecific antibodies (e.g., bispecific antibodies).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels.

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "expression" refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state.

The term "regulating" with reference to expression or activity, as used herein, refers to altering the level of expression or activity. Regulation can occur at the transcription level and/or translation level.

The terms "peptide," "polypeptide," and "protein" are used interchangeably herein to refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer can be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids can include natural amino acids and non-natural amino acids, which have been chemically modified to include a group or a chemical moiety not naturally present on the amino acid. Amino acid analogues can refer to amino acid derivatives. The term "amino acid" includes both D-amino acids and L-amino acids.

The terms "derivative," "variant," and "fragment," when used herein with reference to a polypeptide, refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

As used herein, "fusion" can refer to a protein and/or nucleic acid comprising one or more non-native sequences (e.g., moieties). A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as Alexa fluor dyes, Cyanine3 dye, Cyanine5 dye.

The phrase "exogenous T cell receptor (TCR) complex" or "exogenous TCR complex," as used herein, refers to a TCR complex in which one or more chains of the TCR are introduced into the genome of an immune cell that may or may not endogenously express the TCR. In some cases, an exogenous TCR complex can refer to a TCR complex in which one or more chains of an endogenous TCR complex have one or more mutated sequences, for example at either the nucleic acid or amino acid level. Expression of an exogenous TCR on an immune cell can confer binding specificity for an epitope or antigen (e.g., an epitope or antigen preferentially present on the surface of a cancer cell or other disease-causing cell or particle). An exogenous TCR complex can comprise a TCR-alpha, a TCR-beta chain, a CD3-gamma chain, a CD3-delta chain, a CD3-zeta chain, or any combination thereof, which is introduced into the genome. In some cases, the chain introduced into the genome may replace the endogenously occurring chain.

The terms "subject," "individual," and "patient" are used interchangeably herein to refer to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the quantity of a composition, for example a composition comprising immune cells such as lymphocytes (e.g., T lymphocytes and/or NK cells) of the present disclosure, that is sufficient to result in a desired activity upon administration to a subject in need thereof. Within the context of the present disclosure, the term "therapeutically effective" refers to that quantity of a composition that is sufficient to delay the manifestation, arrest the progression, relieve or alleviate at least one symptom of a disorder treated by the methods of the present disclosure.

The term "genetic profile," as used herein, refers to information about specific genes, including variations and gene expression in an individual or in a certain type of tissue. A genetic profile can be used for neoantigen selection. The term "somatic mutation profile," as used herein, refers to information about specific genes associated with somatic mutation, including but not limited to specific genes resulted from somatic mutation. A somatic mutation profile can be used for neoantigen selection.

In an aspect, the present disclosure provides a modified tumor infiltrating lymphocyte (TIL) that specifically binds to tumor associated antigen, including but not limited to a neoantigen. The modified TIL can comprise a chimeric stimulating molecule. The chimeric stimulating molecule can comprise a polypeptide extracellular domain (PED) that binds to the neoantigen. The PED can be fused to an intracellular domain (ICD) of a co-stimulatory molecule that mediates an immune cell activation signal. Binding of the chimeric stimulating molecule to the neoantigen can yield the immune cell activation signal in the modified TIL. In some embodiments, the PED can be an extracellular domain of a surface protein of an unmodified TIL. In some embodiments, examples of the PED include antibodies, as well as derivatives, variants, and fragments thereof.

In an aspect, the present disclosure provides a modified tumor infiltrating lymphocyte (TIL) that specifically binds to a neoantigen, the modified TIL comprising a switch molecule. The switch molecule can comprise an extracellular domain (ECD) of a protein that, in an unmodified TIL, elicits an immune cell inactivation signal upon binding to its ligand. The ECD can be fused to an intracellular domain (ICD) of a co-stimulatory molecule that mediates an immune cell activation signal. Binding of the switch molecule to the ligand can yield the immune cell activation signal in the modified TIL instead of the immune cell inactivation signal.

The TIL can be any cell obtained from a tumor. For example, the TIL can be a cell that has migrated to a tumor. A TIL can be a cell that has infiltrated a tumor. In some embodiments, the TIL is a white blood cell that has migrated into a tumor from the bloodstream of a subject. A TIL can be, for example, a T cell, B cell, monocyte, or natural killer (NK) cell. In some cases, a modified TIL comprises a CD8+ cytotoxic T cell (lymphocyte), Th1 and Th17 CD4+ T cell, a natural killer cell, a dendritic cell, or M1 macrophage. A population of immune cells comprising TILs can be a mixed population of cells. A population of TILs can comprise cells of different phenotypes, cells of different degrees of differentiation, cells of different lineages, or any combination thereof. TILs can generally be defined either biochemically, using cell surface markers, or functionally, by their ability to infiltrate tumors and effect treatment. TILs can be categorized based on expression one or more of the following biomarkers: CD4, CD8, TCR alpha beta, CD25, CD27, CD28, CD56, CD137, CCR7, CD45Ra, CD95, PD-1, and TIM-3. In some embodiments, the modified TIL expresses at least one of PD-1, CD137, and TIM-3. In some cases, a TIL can be functionally defined by its ability to infiltrate solid tumors upon reintroduction into a patient. In some cases, the modified TIL comprises a "primary TIL," referring to a TIL that is obtained from a patient tissue sample. In some cases, the modified TIL comprises a "secondary TILs," referring to a TIL that is has been expanded or proliferated. A TIL can exhibit specific binding to a neoantigen. In some cases, the TCR complex of the TIL confers the antigen binding specificity (e.g., neoantigen binding).

In an aspect, the present disclosure provides a modified T cell that specifically binds to a neoantigen, the modified T cell comprising a switch molecule. The switch molecule can comprise an extracellular domain (ECD) of a protein that, in an unmodified T cell, elicits an immune cell inactivation signal upon binding to its ligand. The ECD may be fused to an intracellular domain (ICD) of a co-stimulatory molecule that mediates an immune cell activation signal. Binding of the switch molecule to the ligand can yield the immune cell activation signal in the modified T cell instead of the immune cell inactivation signal.

The modified T cell can comprise a T cell receptor (TCR) complex which exhibits specific binding to the neoantigen. In some embodiments, the TCR complex is an endogenous TCR complex. In some embodiments, the TCR is an exogenous TCR complex. The TCR complex, e.g., endogenous or exogenous, of the modified immune cell can confer the antigen binding specificity (e.g., neoantigen binding) of the immune cell. In some embodiments, the present disclosure provides a modified T cell comprising an endogenous TCR complex that specifically binds to a neoantigen, said modified T cell comprising a chimeric stimulating molecule, wherein said chimeric stimulating molecule comprises: a polypeptide extracellular domain (PED) that binds to a membrane protein on a cell including but not limited to a tumor cell, wherein said PED is fused to an intracellular domain (ICD) of a co-stimulatory molecule that mediates an immune cell activation signal, wherein binding of said chimeric stimulating molecule to said membrane protein yields said immune cell activation signal in said modified T cell.

Binding of a modified immune cell, such as a modified T cell or a modified TIL provided herein, to a neoantigen can activate the immune cell. The switch molecule of the modified cell can be used to provide further control over immune cell activities, such as but not limited to, immune cell activation and expansion. Binding of the switch molecule to its ligand in the modified immune cell, such as a modified T cell or modified TIL, can elicit an immune cell activation signal in the modified immune cell instead of the immune cell inactivation signal. Eliciting the immune cell activation signal in the modified immune cell instead of the immune cell inactivation signal may minimize an immune-suppressive effect in the immune cell. Minimizing an immune-suppressive effect in the immune cell can increase the effectiveness of the immune cell in an immune response, for example by increasing immune cell cytotoxicity against a target cell, such as a tumor cell.

The switch molecule can comprise an extracellular domain (ECD) of a protein that, in an unmodified immune cell, elicits an immune cell inactivation signal upon binding to its ligand. The protein can be a signaling receptor or any functional fragment, derivative, or variant thereof. In some cases, the signaling receptor can be a membrane bound receptor. A signaling receptor can, in response to ligand binding, induce one or more signaling pathways in a cell. In some cases, the signaling receptor can be a non-membrane bound receptor. The switch molecule can comprise a fragment, for example an extracellular domain, of a receptor selected from a G-protein coupled receptor (GPCR); an integrin receptor; a cadherin receptor; a catalytic receptor (e.g., kinases); a death receptor; a checkpoint receptor; a cytokine receptor; a chemokine receptor; a growth factor receptor; a hormone receptor; and an immune receptor.

In some embodiments, the switch molecule comprises a fragment of an immune checkpoint receptor, which may be involved in regulation of the immune system. Non-limiting examples of such receptors include, but are not limited to, programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and T-cell immunoreceptor with Ig and ITIM domains (TIGIT).

In some embodiments, the switch molecule comprises at least an extracellular fragment of a TCR, which may be involved in recognizing a neoantigen of a target cell (e.g., a cancer cell antigen or a tumor antigen). In some examples, the switch molecule can comprise the extracellular variable regions of the TCR u and/or R chains.

A switch molecule comprising an immune checkpoint receptor, or any derivative, variant or fragment thereof, can bind an antigen comprising any suitable immune checkpoint receptor ligand, or any derivative, variant or fragment thereof. Non-limiting examples of such ligands include, but are not limited to, B7-1, B7-H3, B7-H4, HVEM (Herpesvirus Entry Mediator), AP2M1, CD80, CD86, SHP-2, PPP2R5A, MHC (e.g., class I, class II), PD-L1, and PD-L2.

In some embodiments, the switch molecule comprises a fragment of a cytokine receptor. Cytokine receptors can serve a variety of functions, non-limiting examples of which include immune cell regulation and mediating inflammation. In some embodiments, the switch molecule comprises a cytokine receptor, for example a type I cytokine receptor or a type II cytokine receptor, or any derivative, variant or fragment thereof. In some embodiments, the switch molecule comprises an interleukin receptor (e.g., IL-2R, IL-3R, IL-4R, IL-5R, IL-6R, IL-7R, IL-9R, IL-11R, IL-12R, IL-13R, IL-15R, IL-21R, IL-23R, IL-27R, and IL-31R), a colony stimulating factor receptor (e.g., erythropoietin receptor, CSF-1R, CSF-2R, GM-CSFR, and G-CSFR), a hormone receptor/neuropeptide receptor (e.g., growth hormone receptor, prolactin receptor, and leptin receptor), or any derivative, variant or fragment thereof. In some embodiments, the switch molecule comprises a type II cytokine receptor, or any derivative, variant or fragment thereof. In some embodiments, the switch molecule comprises an interferon receptor (e.g., IFNAR1, IFNAR2, and IFNGR), an interleukin receptor (e.g., IL-10R, IL-20R, IL-22R, and IL-28R), a tissue factor receptor (also called platelet tissue factor), or any derivative, variant or fragment thereof.

In some embodiments, the switch molecule can comprise at least an extracellular region (e.g., ligand binding domain) of a catalytic receptor such as a receptor tyrosine kinase (RTK), or any derivative, variant or fragment thereof. In some embodiments, the switch molecule comprises a class I RTK (e.g., the epidermal growth factor (EGF) receptor family including EGFR; the ErbB family including ErbB-2, ErbB-3, and ErbB-4), a class II RTK (e.g., the insulin receptor family including INSR, IGF-1R, and IRR), a class III RTK (e.g., the platelet-derived growth factor (PDGF) receptor family including PDGFR-α, PDGFR-β, CSF-1R, KIT/SCFR, and FLK2/FLT3), a class IV RTK (e.g., the fibroblast growth factor (FGF) receptor family including FGFR-1, FGFR-2, FGFR-3, and FGFR-4), a class V RTK (e.g., the vascular endothelial growth factor (VEGF) receptor family including VEGFR1, VEGFR2, and VEGFR3), a class VI RTK (e.g., the hepatocyte growth factor (HGF) receptor family including hepatocyte growth factor receptor (HGFR/MET) and RON), a class VII RTK (e.g., the tropomyosin receptor kinase (Trk) receptor family including TRKA, TRKB, and TRKC), a class VIII RTK (e.g., the ephrin (Eph) receptor family including EPHA1, EPHA2, EPHA3, EPHA4, EPHA5, EPHA6, EPHA7, EPHA8, EPHB1, EPHB2, EPHB3, EPHB4, EPHB5, and EPHB6), a class IX RTK (e.g., AXL receptor family such as AXL, MER, and TRYO3), a class X RTK (e.g., LTK receptor family such as LTK and ALK), a class XI RTK (e.g., TIE receptor family such as TIE and TEK), a class XII RTK (e.g., ROR receptor family ROR1 and ROR2), a class XIII RTK (e.g., the discoidin domain receptor (DDR) family such as DDR1 and DDR2), a class XIV RTK (e.g., RET receptor family such as RET), a class XV RTK (e.g., KLG receptor family including PTK7), a class XVI RTK (e.g., RYK receptor family including Ryk), a class XVII RTK (e.g., MuSK receptor family such as MuSK), or any derivative, variant or fragment thereof.

A switch molecule comprising a RTK, or any derivative, variant or fragment thereof, can bind an antigen comprising any suitable RTK ligand, or any derivative, variant or fragment thereof. Non limiting examples of RTK ligands include growth factors, cytokines, and hormones. Growth factors include, for example, members of the epidermal growth factor family (e.g., epidermal growth factor or EGF, heparin-binding EGF-like growth factor or HB-EGF, transforming growth factor-α or TGF-α, amphiregulin or AR, epiregulin or EPR, epigen, betacellulin or BTC, neuregulin-1 or NRG1, neuregulin-2 or NRG2, neuregulin-3 or NRG3, and neuregulin-4 or NRG4), the fibroblast growth factor family (e.g., FGF1, FGF2, FGF3, FGF4, FGF5, FGF6, FGF7, FGF8, FGF9, FGF10, FGF11, FGF12, FGF13, FGF14, FGF15/19, FGF16, FGF17, FGF18, FGF20, FGF21, and FGF23), the vascular endothelial growth factor family (e.g., VEGF-A, VEGF-B, VEGF-C, VEGF-D, and PIGF), and the platelet-derived growth factor family (e.g., PDGFA, PDGFB, PDGFC, and PDGFD). Hormones include, for example, members of the insulin/IGF/ relaxin family (e.g., insulin, insulin-like growth factors, relaxin family peptides including relaxin1, relaxin2, relaxin3, Leydig cell-specific insulin-like peptide (gene INSL3), early placenta insulin-like peptide (ELIP) (gene INSL4), insulin-like peptide 5 (gene INSL5), and insulin-like peptide 6).

In some embodiments, a switch molecule comprises at least an extracellular region (e.g., ligand binding domain) of a catalytic receptor such as a receptor threonine/serine kinase (RTSK), or any derivative, variant or fragment thereof. A switch molecule can comprise a type I RTSK, type II RTSK, or any derivative, variant or fragment thereof. A switch molecule can comprise a type I receptor, or any derivative, variant or fragment thereof, selected from the group consisting of: ALK1 (ACVRL1), ALK2 (ACVR1A), ALK3 (BMPR1A), ALK4 (ACVR1B), ALK5 (TGFβR1), ALK6 (BMPR1B), and ALK7 (ACVR1C). A switch molecule can comprise a type II receptor, or any derivative, variant or fragment thereof, selected from the group consisting of: TGFβR2, BMPR2, ACVR2A, ACVR2B, and AMHR2 (AMHR). In some embodiments, the switch molecule comprises a TGF-β receptor, or any derivative, variant or fragment thereof.

A switch molecule comprising a RTSK, or any derivative, variant or fragment thereof, can bind an antigen comprising any suitable RTSK ligand, or any derivative, variant or fragment thereof.

The switch molecule can comprise an intracellular domain (ICD) of a co-stimulatory molecule that elicits an immune cell activation signal. The co-stimulatory molecule may bind a ligand. In some cases, the co-stimulatory molecule may be activated by a ligand responsive protein. In some embodiments, the co-stimulatory molecule is operable to regulate a proliferative and/or survival signal in the immune cell. In some embodiments, the ICD is an intracellular domain of a co-stimulatory molecule selected from an MHC class I protein, an MHC class II protein, a TNF receptor protein, an immunoglobulin-like protein, a cytokine receptor, an integrin, a signaling lymphocytic activation molecule (SLAM protein), an activating NK cell receptor, BTLA, or a Toll ligand receptor. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD3, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD5, CD53, CD58/LFA-3, CD69, CD7, CD8 α, CD8 f, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, IL-12R, Integrin α4/CD49d, Integrin α4 β1, Integrin α4 β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/ TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/ TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6.

The ECD and the ICD of a switch molecule can be joined by a transmembrane domain, for example by a membrane spanning segment. In some embodiments, the membrane spanning segment comprises a polypeptide. The membrane spanning polypeptide can have any suitable polypeptide sequence. In some cases, the membrane spanning polypeptide comprises a polypeptide sequence of a membrane spanning portion of an endogenous or wild-type membrane spanning protein. In some embodiments, the membrane spanning polypeptide comprises a polypeptide sequence having at least 1 (e.g., at least 2, 3, 4, 5, 6, 7, 8, 9, 10 or greater) of an amino acid substitution, deletion, and insertion compared to a membrane spanning portion of an endogenous or wild-type membrane spanning protein. In some embodiments, the membrane spanning polypeptide comprises a non-natural polypeptide sequence, such as the sequence of a polypeptide linker. The polypeptide linker may be flexible or rigid. The polypeptide linker can be structured or unstructured. In some embodiments, the membrane spanning polypeptide transmits a signal from the ECD to the ICD, for example a signal indicating ligand-binding.

Binding of a ligand to the switch molecule can yield an immune cell activation signal in the modified immune cell. In some embodiments, the immune cell activation signal is mediated by an activation factor. The activation factor can be an immunomodulating molecule. The activation factor may bind, activate, or stimulate T cells or other immune cells to modulate their activity. In some embodiments, the activation factor can be secreted from the immune cell. The activation factor can be, for example, a soluble cytokine, a soluble chemokine, or a growth factor molecule. Non-limiting examples of activation factors which can mediate the immune cell activation include a soluble cytokine, such as IL-1, IL-2, IL-6, IL-7, IL-8, IL-10, IL-12, IL-15, IL-21, tumor necrosis factor (TNF), transforming growth factor (TGF), interferon (IFN), or any functional fragment or variant thereof.

The immune cell activation signal can comprise or result in a clonal expansion of the modified immune cell (e.g., modified TIL or modified T cell); cytokine release by the modified immune cell (e.g., modified TIL or modified T cell); cytotoxicity of the modified immune cell (e.g., modified TIL or modified T cell); proliferation of the modified immune cell (e.g., modified TIL or modified T cell); differentiation, dedifferentiation or transdifferentiation of the modified immune cell (e.g., modified TIL or modified T cell); movement and/or trafficking of the modified immune cell (e.g., modified TIL or modified T cell); exhaustion and/or reactivation of the modified immune cell (e.g., modified TIL or modified T cell); and release of other intercellular molecules, metabolites, chemical compounds, or combinations thereof by the modified immune cell (e.g., modified TIL or modified T cell).

In some embodiments, the immune cell activity comprises or results in clonal expansion of the immune cell. Clonal expansion can comprise the generation of daughter cells arising from the immune cell. The daughter cells resulting from clonal expansion can comprise the switch molecule. Clonal expansion of the modified immune cell can be greater than that of a comparable immune cell lacking the switch molecule. Clonal expansion of the modified immune cell can be about 5 fold to about 10 fold, about 10 fold to about 20 fold, about 20 fold to about 30 fold, about 30 fold to about 40 fold, about 40 fold to about 50 fold, about 50 fold to about 60 fold, about 60 fold to about 70 fold, about 70 fold to about 80 fold, about 80 fold to about 90 fold, about 90 fold to about 100 fold, about 100 fold to about 200 fold, about 200 fold to about 300 fold, about 300 fold to about 400 fold, about 400 fold to about 500 fold, about 500 fold to about 600 fold, or about 600 fold to about 700 fold greater than a comparable immune cell lacking the switch molecule. In some embodiments, determining clonal expansion can comprise quantifying a number of immune cells, for example with and without switch molecules and after ligand binding to the switch molecule. Quantifying a number of immune cells can be achieved by a variety of techniques, non-limiting examples of which include flow cytometry, Trypan Blue exclusion, and hemocytometry.

In some embodiments, the immune cell activity comprises or results in cytokine release by the immune cell. In some embodiments, the immune cell activity comprises or results in the release of intercellular molecules, metabolites, chemical compounds or combinations thereof. Cytokine release by the modified immune cell can comprise the release of IL-1, IL-2, IL-4, IL-5, IL-6, IL-13, IL-17, IL-21, IL-22, IFNγ, TNFα, CSF, TGFβ, granzyme, and the like. In some embodiments, cytokine release may be quantified using enzyme-linked immunosorbent assay (ELISA), flow cytometry, western blot, and the like. Cytokine release by a modified immune cell can be greater than that of a comparable immune cell lacking the switch molecule. A modified immune cell provided herein can generate about 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold, 40 fold, 50 fold, 60 fold, 70 fold, 80 fold, 90 fold, 100 fold, 150 fold, 200 fold, 250 fold, or over 300 fold greater cytokine release as compared to a comparable immune cell lacking the switch molecule. The modified immune cell can exhibit increased cytokine secretion as compared to a comparable immune cell lacking the switch molecule (e.g., unmodified), when the switch molecule binds to the ligand and the modified immune cell binds to the neoantigen present on a target cell. In some embodiments, the cytokine secreted is IFNγ or IL-2. In some embodiments, cytokine release can be quantified in vitro or in vivo.

In some embodiments, the immune cell activity comprises or results in cytotoxicity of the immune cell. In some cases, cytotoxicity of the modified immune cells provided herein can be used for killing a target cell. An immune cell or population of immune cells expressing a switch molecule can induce death of a target cell. Killing of a target cell can be useful for a variety of applications, including, but not limited to, treating a disease or disorder in which a cell population is desired to be eliminated or its proliferation desired to be inhibited. Cytotoxicity can also refer to the release of cytotoxic cytokines, for example IFNγ or granzyme, by the immune cell. In some cases, modified immune cells provided herein may have altered (i) release of cytotoxins such as perforin, granzymes, and granulysin and/or (ii) induction of apoptosis via Fas-Fas ligand interaction between the T cells and target cells. In some embodiments, cytotoxicity can be quantified by a cytotoxicity assay including, a co-culture assay, ELISPOT, chromium release cytotoxicity assay, and the like. Cytotoxicity of a modified immune cell provided herein can be greater than that of a comparable immune cell lacking the switch molecule. The modified immune cell can exhibit increased cytotoxicity against a target cell as compared to a comparable immune cell lacking the switch molecule (e.g., unmodified), when the switch molecule binds to the ligand and the modified immune cell binds to the neoantigen present on the target cell. A modified immune cell of the disclosure can be about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% more cytotoxic to target cells as compared to a comparable immune cell lacking the switch molecule. A modified immune cell of the disclosure can induce death of target cells that is at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% greater than that of a comparable immune cell lacking the switch molecule. In some embodiments, an immune cell provided herein can induce apoptosis in target cells displaying target epitopes (e.g., neoantigens) on their surface. In some embodiments, cytotoxicity can be determined in vitro or in vivo. In some embodiments, determining cytotoxicity can comprise determining a level of disease after administration of modified immune cells provided herein as compared to a level of disease prior to the administration. In some embodiments, determining cytotoxicity can comprise determining a level of disease after administration of modified immune cells provided herein and a level of disease after administration of comparable immune cells lacking the switch molecule.

In some embodiments, immune cell activity comprises or results in proliferation of the immune cell. Proliferation of the immune cell can refer to expansion of the immune cell. Proliferation of the immune cell can refer to phenotypic changes of the immune cell. Proliferation of a modified immune cell of the disclosure can be greater than that of a comparable immune cell lacking the switch molecule. Proliferation of a modified immune cell provided herein can be about 5 fold to about 10 fold, about 10 fold to about 20 fold, about 20 fold to about 30 fold, about 30 fold to about 40 fold, about 40 fold to about 50 fold, about 50 fold to about 60 fold, about 60 fold to about 70 fold, about 70 fold to about 80 fold, about 80 fold to about 90 fold, about 90 fold to about 100 fold, about 100 fold to about 200 fold, from about 200 fold to about 300 fold, from about 300 fold to about 400 fold, from about 400 fold to about 500 fold, from about 500 fold to about 600 fold, or from about 600 fold to about 700 fold greater than the proliferation of a comparable immune cell lacking the switch molecule. In some embodiments, proliferation can be determined by quantifying a number of immune cells. Quantifying a number of immune cells can comprise flow cytometry, Trypan Blue exclusion, and/or hemocytometry. Proliferation can also be determined by phenotypic analysis of the immune cells.

In some embodiments, immune cell activity can comprise or result in differentiation, dedifferentiation, or transdifferentiation of the immune cell. Differentiation, dedifferentiation, or transdifferentiation of an immune cell can be determined by evaluating phenotypic expression of markers of differentiation, dedifferentiation, or transdifferentiation on a cell surface by flow cytometry. In some embodiments, a modified immune cell provided herein has increased differentiation ability as compared to a comparable immune cell lacking the switch molecule. In some embodiments, an modified immune cell provided herein has increased dedifferentiation ability as compared to a comparable immune cell lacking the switch molecule. In some embodiments, a modified immune cell provided herein has greater transdifferentiation ability as compared to a comparable immune cell lacking the switch molecule.

In some embodiments, immune cell activity can comprise or result in movement and/or trafficking of the immune cell. In some embodiments, movement can be determined by quantifying localization of the immune cell to a target site. For example, modified immune cells provided herein can be quantified at a target site after administration, for example at a site that is not the target site. Quantification can be performed by isolating a lesion and quantifying a number of immune cells, for example tumor infiltrating lymphocytes, comprising the switch molecule. Movement and/or trafficking of an immune cell comprising a switch molecule can be greater than that of a comparable immune cell lacking the switch molecule. In some embodiments, the number of immune cells comprising the switch molecule at a target site, for example a tumor lesion, can be about 5×, 10×, 15×, 20×, 25×, 30×, 35×, or 40× that of the number of comparable immune cells lacking the switch molecule. Trafficking can also be determined in vitro utilizing a transwell migration assay. In some embodiments, the number of immune cells comprising the switch molecule at a target site, for example in a transwell migration assay, can be about 5×, 10×, 15×, 20×, 25×, 30×, 35×, or 40× that of the number of comparable immune cells lacking the switch molecule.

In some embodiments, immune cell activity can comprise or result in exhaustion and/or activation of the immune cell. Exhaustion and/or activation of an immune cell can be determined by phenotypic analysis by flow cytometry or microscopic analysis. For example, expression levels of markers of exhaustion, for instance programmed cell death protein 1 (PD1), lymphocyte activation gene 3 protein (LAG3), 2B4, CD160, Tim3, and T cell immunoreceptor with immunoglobulin and ITIM domains (TIGIT), can be determined quantitatively and/or qualitatively. In some cases, immune cells, such as T cells, can lose effector functions in a hierarchical manner and become exhausted. As a result of exhaustion, functions such as IL-2 production and cytokine expression, as well as high proliferative capacity, can be lost. Exhaustion can also be followed by defects in the production of IFNγ, TNF and chemokines, as well as in degranulation. Exhaustion or activation of a modified immune cell provided herein can be greater than that of a comparable immune cell lacking the switch molecule. In some embodiments, the immune cell provided herein can undergo at least about a 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold, 40 fold, 50 fold, 60 fold, 70 fold, 80 fold, 90 fold, 100 fold, 150 fold, 200 fold, 250 fold, or over 300 increase in exhaustion or activation as compared to a comparable immune cell lacking the switch molecule. In some embodiments, the immune cell comprising provided herein can undergo at least about a 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold, 40 fold, 50 fold, 60 fold, 70 fold, 80 fold, 90 fold, 100 fold, 150 fold, 200 fold, 250 fold, or over 300 decrease in exhaustion or activation as compared to a comparable immune cell lacking the switch molecule.

In some embodiments, upon binding of the switch molecule to the ligand, the modified immune cell (e.g., modified TIL or modified T cell) exhibits enhanced neoantigen binding as compared to a comparable immune cell lacking the switch molecule.

In an aspect, the present disclosure provides a modified immune cell comprising a chimeric antigen receptor (CAR) and a T cell receptor (TCR) complex which exhibits specific binding to a neoantigen. The CAR can comprise an antigen interacting domain capable of binding a B cell surface protein, a transmembrane domain, and an intracellular signaling domain.

The T cell receptor (TCR) complex which exhibits specific binding to the neoantigen can be an endogenous TCR complex or an exogenous TCR complex. The TCR complex, e.g., endogenous or exogenous, of the modified immune cell can confer the antigen binding specificity (e.g., neoantigen binding) of the immune cell.

In some embodiments, the immune cell is a tumor infiltrating lymphocyte (TIL). The TIL can be, for example, a T cell, B cell, monocyte, or natural killer (NK) cell. In some cases, the TIL comprises a CD8+ cytotoxic T cell (lymphocyte), Th1 and Th17 CD4+ T cell, a natural killer cell, a dendritic cell, or M1 macrophage. In some embodiments, the TIL can express at least one of PD-1, CD137, and TIM-3. In some cases, the modified TIL comprises a "primary TIL," referring to a TIL that is obtained from a patient tissue sample. In some cases, the modified TIL comprises a "secondary TILs," referring to a TIL that is has been expanded or proliferated.

The CAR can comprise an antigen interacting domain capable of binding a B cell surface protein. The B cell surface protein can be any protein that may be found on the surface of a B cell. Non-limiting examples include CD1d, CD5, CD10, CD11a, CD19, CD20, CD21, CD22, CD23, CD24, CD25, CD27, CD28, CD29, CD34, CD37, CD38, CD40, CD44, CD45, CD49b, CD69, CD72, CD74, CD80, CD83, CD84, CD86, CD93, CD95, CD117, CD127, CD138, CD147, CD148, CD185, CD270, CD284, and CD360. In some embodiments, the antigen interacting domain of the CAR can be capable of binding a surface protein on a non-B cell, as long as the binding to the surface protein does not significantly compromise the general health status or the immune system of the host. In some embodiments, the surface protein is a surfer protein on an immune cell. In some embodiments, the surface protein is a surface protein on a cell other than an immune cell. In some embodiments, the surface protein may be selected from, with the proviso that the binding to the surface protein does not significantly compromise the general health status or the immune system of the host, CD31, CD32, A, B, CD33, CD34, CD35, CD36, CD37, CD38, CD39, CD40, CD41, CD42, a, b, c, d, CD43, CD44, CD45, CD46, CD47, CD48, CD49 (a, b, c, d, e, f), CD50, CD51, CD52, CD53, CD54, CD55, CD56, CD57, CD58, CD59, CD61, CD62 (E, L, P), CD63, CD64 (A, B, C), CD66 (a, b, c, d, e, f), CD68, CD69, CD70, CD71, CD72, CD73, CD74, CD78, CD79 (a, b), CD80, CD81, CD82, CD83, CD84, CD85 (a, d, e, h, j, k), CD86, CD87, CD88, CD89, CD90, CD91, CD92, CD93, CD94, CD95, CD96, CD97, CD98, CD99, CD100, CD1 (a-c), 1A, 1D, 1E, CD2, CD3 (γ, δ, ε), CD4, CD5, CD6, CD7, CD8, a, CD9, CD10, CD11 (a, b, c, d), CD13, CD14, CD15, CD16, A, B, CD18, CD19, CD20, CD21, CD22, CD23, CD24, CD25, CD26, CD27, CD28, CD29, CD30, CD101, CD102, CD103, CD104, CD105, CD106, CD107 (a, b), CD108, CD109, CD110, CD111, CD112, CD113, CD114, CD115, CD116, CD117, CD118, CD119, CD120 (a, b), CD121 (a, b), CD122, CD123, CD124, CD125, CD126, CD127, CD129, CD130, CD131, CD132, CD133, CD134, CD135, CD136, CD137, CD138, CD140b, CD141, CD142, CD143, CD144, CD146, CD147, CD148, CD150, CD191, CD192, CD193, CD194, CD195, CD196, CD197, CDw198, CDw199, CD200, CD201, CD202b, CD204, CD205, CD206, CD207, CD208, CD209, CDw210 (a, b), CD212, CD213a (1, 2), CD217, CD218, (a, b), CD220, CD221, CD222, CD223, CD224, CD225, CD226, CD227, CD228, CD229, CD230, CD233, CD234, CD235 (a, b), CD236, CD238, CD239, CD240CE, CD240D, CD241, CD243, CD244, CD246, CD247, CD248, CD249, CD252, CD253, CD254, CD256, CD257, CD258, CD261, CD262, CD263, CD264, CD265, CD266, CD267, CD268, CD269, CD271, CD272, CD273, CD274, CD275, CD276, CD278, CD279, CD280, CD281, CD282, CD283, CD284, CD286, CD288, CD289, CD290, CD292, CDw293, CD294, CD295, CD297, CD298, CD299, CD300A, CD301, CD302, CD303, CD304, CD305, CD306, CD307, CD309, CD312, CD314, CD315, CD316, CD317, CD318, CD320, CD321, CD322, CD324, CD325, CD326, CD328, CD329, CD331, CD332, CD333, CD334, CD335, CD336, CD337, CD338, CD339, CD340, CD344, CD349, CD350, CD151, CD152, CD153, CD154, CD155, CD156 (a, b, c), CD157, CD158, (a, d, e, i, k), CD159 (a, c), CD160, CD161, CD162, CD163, CD164, CD166, CD167 (a, b), CD168, CD169, CD170, CD171, CD172 (a, b, g), CD174, CD177, CD178, CD179 (a, b), CD180, CD181, CD182, CD183, CD184, CD185, and CD186.

In some embodiments, the antigen interacting domain of the CAR can be capable of binding a B cell surface protein or a fragment thereof on a dead B cell. B cell apoptosis can occur before or after development of an immune response (e.g., an immune response towards a tumor cell). Thus, a dead B cell or its debris can still have the B cell surface protein or the fragment thereof presented on the surface. The ability of the CAR to target both live and dead B cells may increase the chance of the immune cell comprising the CAR to (i) bind the B cell surface protein and (i) initiate signaling of the intracellular signaling domain. In some cases, the signaling of the intracellular signaling domain may promote expansion (proliferation) of the immune cell comprising the CAR.

In some embodiments, the antigen interacting domain of the CAR can be capable of binding a B cell surface protein or a fragment thereof that is coupled (e.g., via a covalent and/or non-covalent bond) to a surface of particles (e.g., nanoparticles). The particles may be any particulate materials comprising organic and/or inorganic material. The particles may have various shapes and sizes. The particles may be about 1 nanometers (nm) to about 50 micrometers (μm) in at least one dimension. The particles may be at least about 1 nm, 5 nm, 10 nm, 50 nm, 100 nm, 500 nm, 1 μm, 5 μm, 10 μm, 50 μm, or more in at least one dimension. The particles may be at most about 50 μm, 10 μm, 5 μm, 1 μm, 500 nm, 100 nm, 50 nm, 10 nm, 5 nm, 1 nm, or less in at least one dimension. The particles may be nanoparticles, microparticles, nanospheres, microspheres, nanorods, microrods, nanofibers, nanoribbons, etc. Examples of the particle include metal nanoparticles (e.g., gold nanoparticles, silver nanoparticles, and iron nanoparticles), intermetallic nanosemiconductor nanoparticles, core-shell nanoparticles, particles with an inorganic core with a polymer shell, particles with an organic core with a polymer shell, and mixtures thereof. Alternatively, the particles can be organic nanoparticles, such as crosslinked polymers, hydrogel polymers, biodegradable polymers, polylactide (PLA), polyglycolide (PGA), polycaprolactone (PCL), copolymers, polysaccharides, starch, cellulose, chitosan, polyhydroxyalkanoates (PHA), PHB, PHV, lipids, peptides, peptide amphiphiles, polypeptides (e.g., proteins), or combinations thereof. The particles presenting the B cell surface protein on the surface may be introduced in vitro to the immune cell comprising the CAR that binds the B cell surface protein. Alternatively or in addition to, the particles presenting the B cell surface protein may be introduced in vivo (e.g., local or systemic injection) along with the immune cell comprising the CAR. Such particles may be used to expand the population of the immune cell comprising the CAR in vitro or in vivo.

The antigen binding domain can comprise any protein or molecule capable of binding to an antigen, e.g., B cell surface protein. Non-limiting examples of the antigen binding domain include, but are not limited to, a monoclonal antibody, a polyclonal antibody, a recombinant antibody, a human antibody, a humanized antibody, a murine antibody, or a functional derivative, variant or fragment thereof, including, but not limited to, a Fab, a Fab', a F(ab')$_2$, an Fv, a single-chain Fv (scFv), minibody, a diabody, and a single-domain antibody such as a heavy chain variable domain (VH), a light chain variable domain (VL) and a variable domain (VHH) of camelid derived nanobody. In some embodiments, the first antigen binding domain comprises at least one of a Fab, a Fab', a F(ab')$_2$, an Fv, and a scFv. In some embodiments, the antigen binding domain comprises an antibody mimetic. Antibody mimetics refer to molecules which can bind a target molecule with an affinity comparable to an antibody, and include single-chain binding molecules, cytochrome b562-based binding molecules, fibronectin or fibronectin-like protein scaffolds (e.g., adnectins), lipocalin scaffolds, calixarene scaffolds, A-domains and other scaffolds. In some embodiments, an antigen binding domain comprises a transmembrane receptor, or any derivative, variant, or fragment thereof. For example, an antigen binding domain can comprise at least a ligand binding domain of a transmembrane receptor.

In some embodiments, the antigen binding domain can comprise a scFV. A scFv can be derived from an antibody for which the sequences of the variable regions are known. In some embodiments, a scFv can be derived from an antibody sequence obtained from an available mouse hybridoma. A scFv can be obtained from whole-exomic sequencing of a tumor cell or primary cell. In some embodiments, a scFv can be altered. For instance, a scFv may be modified in a variety of ways. In some cases, a scFv can be mutated, so that the scFv may have higher affinity to its target. In some cases, the affinity of the scFv for its target can be optimized for targets expressed at low levels on normal tissues. This optimization can be performed to minimize potential toxicities, such as hypercytokinemia. In other cases, the cloning of a scFv that has a higher affinity for the membrane bound form of a target can be preferable over its soluble form counterpart. This modification can be performed if some targets can also be detected in soluble form at different levels and their targeting can cause unintended toxicity, such as hypercytokinemia.

The antigen binding domain of a CAR of a subject system can be linked to the intracellular signaling domain via a transmembrane domain. A transmembrane domain can be a membrane spanning segment. A transmembrane domain of a subject CAR can anchor the CAR to the plasma membrane of a cell, for example an immune cell. In some embodiments, the membrane spanning segment comprises a polypeptide. The membrane spanning polypeptide linking the antigen binding domain and the intracellular signaling domain of the CAR can have any suitable polypeptide sequence. In some cases, the membrane spanning polypeptide comprises a polypeptide sequence of a membrane spanning portion of an endogenous or wild-type membrane spanning protein. In some embodiments, the membrane spanning polypeptide comprises a polypeptide sequence having at least 1 (e.g., at least 2, 3, 4, 5, 6, 7, 8, 9, 10 or greater) of an amino acid substitution, deletion, and insertion compared to a membrane spanning portion of an endogenous or wild-type membrane spanning protein. In some embodiments, the membrane spanning polypeptide comprises a non-natural polypeptide sequence, such as the sequence of a polypeptide linker. The polypeptide linker may be flexible or rigid. The polypeptide linker can be structured or unstructured. In some embodiments, the membrane spanning polypeptide transmits a signal from an extracellular region of a cell to an intracellular region, for via the antigen binding domain. A native transmembrane portion of CD28 can be used in a CAR. In other cases, a native transmembrane portion of CD8 alpha can also be used in a CAR.

A CAR of the present disclosure can comprise a signaling domain, or any derivative, variant, or fragment thereof, involved in immune cell signaling. The intracellular signaling domain of a CAR can induce activity of an immune cell comprising the CAR. The intracellular signaling domain can transduce the effector function signal and direct the cell to perform a specialized function. The signaling domain can comprise signaling domains of other molecules. In some cases, a truncated portion of the signaling domain is used in a CAR.

In some embodiments, the intracellular signaling domain comprises multiple signaling domains involved in immune cell signaling, or any derivatives, variants, or fragments thereof. For example, the intracellular signaling domain can comprise at least 2 immune cell signaling domains, e.g., at least 2, 3, 4, 5, 7, 8, 9, or 10 immune cell signaling domains. An immune cell signaling domain can be involved in regulating primary activation of the TCR complex in either a stimulatory way or an inhibitory way. The intracellular signaling domain may be that of a T-cell receptor (TCR) complex. The intracellular signaling domain of a subject CAR can comprise a signaling domain of an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MHC complex, NFAT, NF-κB, PLC-γ, iC3b, C3dg, C3d, and Zap70. In some embodiments, the signaling domain includes an immunoreceptor tyrosine-based activation motif or ITAM. A signaling domain comprising an ITAM can comprise two repeats of the amino acid sequence YxxL/I separated by 6-8 amino acids, wherein each x is independently any amino acid, producing the conserved motif YxxL/Ix(6-8)YxxL/I. A signaling domain comprising an ITAM can be modified, for example, by phosphorylation when the antigen binding domain is bound to an epitope. A phosphorylated ITAM can function as a docking site for other proteins, for example proteins involved in various signaling pathways. In some embodiments, the primary signaling domain comprises a modified ITAM domain, e.g., a mutated, truncated, and/or optimized ITAM domain, which has altered (e.g., increased or decreased) activity compared to the native ITAM domain.

In some embodiments, the intracellular signaling domain of a subject CAR comprises an FcγR signaling domain (e.g., ITAM). The FcγR signaling domain can be selected from FcγRI (CD64), FcγRIIA (CD32), FcγRIIB (CD32), FcγRIIIA (CD16a), and FcγRIIIB (CD16b). In some embodiments, the intracellular signaling domain comprises an FcεR signaling domain (e.g., ITAM). The FcεR signaling domain can be selected from FcεRI and FcεRII (CD23). In some embodiments, the intracellular signaling domain comprises an FcαR signaling domain (e.g., ITAM). The FcαR signaling domain can be selected from FcαRI (CD89) and Fcα/μR. In some embodiments, the intracellular signaling domain comprises a CD3 ζ signaling domain. In some embodiments, the primary signaling domain comprises an ITAM of CD3 ζ.

In some embodiments, an intracellular signaling domain of a subject CAR comprises an immunoreceptor tyrosine-based inhibition motif or ITIM. A signaling domain comprising an ITIM can comprise a conserved sequence of amino acids (S/I/V/LxYxxI/V/L) that is found in the cytoplasmic tails of some inhibitory receptors of the immune system. A primary signaling domain comprising an ITIM can be modified, for example phosphorylated, by enzymes such as a Src kinase family member (e.g., Lck). Following phosphorylation, other proteins, including enzymes, can be recruited to the ITIM. These other proteins include, but are not limited to, enzymes such as the phosphotyrosine phosphatases SHP-1 and SHP-2, the inositol-phosphatase called SHIP, and proteins having one or more SH2 domains (e.g., ZAP70). A intracellular signaling domain can comprise a signaling domain (e.g., ITIM) of BTLA, CD5, CD31, CD66a, CD72, CMRF35H, DCIR, EPO-R, FcγRIIB (CD32), Fc receptor-like protein 2 (FCRL2), Fc receptor-like protein 3 (FCRL3), Fc receptor-like protein 4 (FCRL4), Fc receptor-like protein 5 (FCRL5), Fc receptor-like protein 6 (FCRL6), protein G6b (G6B), interleukin 4 receptor (IL4R), immunoglobulin superfamily receptor translocation-associated 1 (IRTA1), immunoglobulin superfamily receptor translocation-associated 2 (IRTA2), killer cell immunoglobulin-like receptor 2DL1 (KIR2DL1), killer cell immunoglobulin-like receptor 2DL2 (KIR2DL2), killer cell immunoglobulin-like receptor 2DL3 (KIR2DL3), killer cell immunoglobulin-like receptor 2DL4 (KIR2DL4), killer cell immunoglobulin-like receptor 2DL5 (KIR2DL5), killer cell immunoglobulin-like receptor 3DL1 (KIR3DL1), killer cell immunoglobulin-like receptor 3DL2 (KIR3DL2), leukocyte immunoglobulin-like receptor subfamily B member 1 (LIR1), leukocyte immunoglobulin-like receptor subfamily B member 2 (LIR2), leukocyte immunoglobulin-like receptor subfamily B member 3 (LIR3), leukocyte immunoglobulin-like receptor subfamily B member 5 (LIR5), leukocyte immunoglobulin-like receptor subfamily B member 8 (LIR8), leukocyte-associated immunoglobulin-like receptor 1 (LAIR-1), mast cell function-associated antigen (MAFA), NKG2A, natural cytotoxicity triggering receptor 2 (NKp44), NTB-A, programmed cell death protein 1 (PD-1), PILR, SIGLECL1, sialic acid binding Ig like lectin 2 (SIGLEC2 or CD22), sialic acid binding Ig like lectin 3 (SIGLEC3 or CD33), sialic acid binding Ig like lectin 5 (SIGLEC5 or CD170), sialic acid binding Ig like lectin 6 (SIGLEC6), sialic acid binding Ig like lectin 7 (SIGLEC7), sialic acid binding Ig like lectin 10 (SIGLEC10), sialic acid binding Ig like lectin 11 (SIGLEC11), sialic acid binding Ig like lectin 4 (SIGLEC4), sialic acid binding Ig like lectin 8 (SIGLEC8), sialic acid binding Ig like lectin 9 (SIGLEC9), platelet and endothelial cell adhesion molecule 1 (PECAM-1), signal regulatory protein (SIRP 2), and signaling threshold regulating transmembrane adaptor 1 (SIT). In some embodiments, the intracellular signaling domain comprises a modified ITIM domain, e.g., a mutated, truncated, and/or optimized ITIM domain, which has altered (e.g., increased or decreased) activity compared to the native ITIM domain.

In some embodiments, the intracellular signaling domain comprises at least 2 ITAM domains (e.g., at least 3, 4, 5, 6, 7, 8, 9, or 10 ITAM domains). In some embodiments, the intracellular signaling domain comprises at least 2 ITIM domains (e.g., at least 3, 4, 5, 6, 7, 8, 9, or 10 ITIM domains) (e.g., at least 2 primary signaling domains). In some embodiments, the intracellular signaling domain comprises both ITAM and ITIM domains.

In some cases, the intracellular signaling domain of a subject CAR can include a co-stimulatory domain. In some embodiments, a co-stimulatory domain, for example from co-stimulatory molecule, can provide co-stimulatory signals for immune cell signaling, such as signaling from ITAM and/or ITIM domains, e.g., for the activation and/or deactivation of immune cell activity. In some embodiments, a co-stimulatory domain is operable to regulate a proliferative and/or survival signal in the immune cell. In some embodiments, a co-stimulatory signaling domain comprises a signaling domain of a MHC class I protein, MHC class II protein, TNF receptor protein, immunoglobulin-like protein, cytokine receptor, integrin, signaling lymphocytic activation molecule (SLAM protein), activating NK cell receptor, BTLA, or a Toll ligand receptor. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD5, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4 β1, Integrin α407/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6. In some embodiments, the intracellular signaling domain comprises multiple co-stimulatory domains, for example at least two, e.g., at least 3, 4, or 5 co-stimulatory domains. Co-stimulatory signaling regions may provide a signal synergistic with the primary effector activation signal and can complete the requirements for activation of a T cell. In some embodiments, the addition of co-stimulatory domains to the CAR can enhance the efficacy and persistence of the immune cells provided herein.

Binding of the CAR to the B cell surface protein can enhance immune cell proliferation as compared to an immune cell lacking the CAR. Proliferation of the immune cell can refer to expansion of the immune cell. Proliferation of the immune cell can refer to phenotypic changes of the immune cell. Proliferation of an immune cell comprising a CAR provided herein can be greater than that of a comparable immune cell lacking the CAR which exhibits binding to a B cell surface protein. Proliferation of an immune cell comprising the CAR can be about 5 fold to about 10 fold, about 10 fold to about 20 fold, about 20 fold to about 30 fold, about 30 fold to about 40 fold, about 40 fold to about 50 fold, about 50 fold to about 60 fold, about 60 fold to about 70 fold, about 70 fold to about 80 fold, about 80 fold to about 90 fold, about 90 fold to about 100 fold, about 100 fold to about 200 fold, from about 200 fold to about 300 fold, from about 300 fold to about 400 fold, from about 400 fold to about 500 fold, from about 500 fold to about 600 fold, from about 600 fold to about 700 fold greater than the proliferation of a comparable immune cell lacking the CAR. Proliferation of an immune cell comprising the CAR can be about 5 fold to about 10 fold, about 10 fold to about 20 fold, about 20 fold to about 30 fold, about 30 fold to about 40 fold, about 40 fold to about 50 fold, about 50 fold to about 60 fold, about 60 fold to about 70 fold, about 70 fold to about 80 fold, about 80 fold to about 90 fold, about 90 fold to about 100 fold, about 100 fold to about 200 fold, from about 200 fold to about 300 fold, from about 300 fold to about 400 fold, from about 400 fold to about 500 fold, from about 500 fold to about 600 fold, from about 600 fold to about 700 fold greater than the proliferation of a comparable immune cell lacking the CAR, and wherein the proliferation is ascertained at least about 12, 24, 36, 48, 60, 72, 84, or 96 hours after contacting the B cell to the B cell surface protein. The enhanced proliferation can be ascertained either in vitro or in vivo. In some embodiments, proliferation can comprise quantifying the number of immune cells. Quantifying a number of immune cells can comprise flow cytometry, Trypan Blue exclusion, and/or hemocytometry. Proliferation can also be determined by phenotypic analysis of the immune cells.

In an aspect, the present disclosure provides a modified immune cell that specifically binds to a neoantigen, wherein the modified immune cell comprises: (a) a chimeric stimulating molecule comprising a polypeptide extracellular domain (PED) that binds to the neoantigen, wherein the PED is fused to an intracellular domain (ICD) of a co-stimulatory molecule that mediates an immune cell activation signal, and wherein binding of the chimeric stimulating molecule to the neoantigen yields the immune cell activation signal in the modified immune cell, and (b) a chimeric antigen receptor comprising (i) an antigen interacting domain capable of binding a B cell surface protein; (ii) a transmembrane domain; and (iii) an intracellular signaling domain. In some embodiments, the PED can be an extracellular domain of a surface protein of an unmodified TIL. In some embodiments, examples of the PED include antibodies, as well as derivatives, variants, and fragments thereof.

In an aspect, the present disclosure provides a modified immune cell that specifically binds to a neoantigen, wherein the modified immune cell comprises: (a) a switch molecule comprising an extracellular domain (ECD) of a protein that, in an unmodified immune cell, elicits an immune cell inactivation signal upon binding to its ligand, wherein the ECD is fused to an intracellular domain (ICD) of a co-stimulatory molecule that mediates an immune cell activation signal, and wherein binding of the switch molecule to the ligand yields the immune cell activation signal in the modified immune cell instead of the immune cell inactivation signal, and (b) a chimeric antigen receptor comprising (i) an antigen interacting domain capable of binding a B cell surface protein; (ii) a transmembrane domain; and (iii) an intracellular signaling domain.

In an aspect, the present disclosure provides a modified tumor infiltrating lymphocyte (TIL) that specifically binds to a neoantigen, wherein the modified immune cell comprises: (a) a switch molecule comprising an extracellular domain (ECD) of a protein that, in an unmodified immune cell, elicits an immune cell inactivation signal upon binding to its ligand, wherein the ECD is fused to an intracellular domain (ICD) of a co-stimulatory molecule that mediates an immune cell activation signal, and wherein binding of the switch molecule to the ligand yields the immune cell activation signal in the modified TIL instead of the immune cell inactivation signal, and (b) a chimeric antigen receptor comprising (i) an antigen interacting domain capable of binding a B cell surface protein; (ii) a transmembrane domain; and (iii) an intracellular signaling domain.

In an aspect, the present disclosure provides a modified immune cell overexpressing a cytokine, for example a chemokine, wherein the immune cell is (i) a tumor infiltrating lymphocyte (TIL); (ii) a stromal tumor infiltrating lymphocyte (sTIL); or (iii) a T cell exhibiting specific binding to an antigen. The modified immune cell overexpressing the chemokine can be any modified immune cell provided herein.

Cytokines refer to proteins (e.g., chemokines, interferons, lymphokines, interleukins, and tumor necrosis factors) released by cells which can affect cell behavior. Cytokines are produced by a broad range of cells, including immune cells such as macrophages, B lymphocytes, T lymphocytes and mast cells, as well as endothelial cells, fibroblasts, and various stromal cells. A given cytokine can be produced by more than one type of cell. Cytokines can be involved in producing systemic or local immunomodulatory effects.

Certain cytokines can function as pro-inflammatory cytokines. Pro-inflammatory cytokines refer to cytokines involved in inducing or amplifying an inflammatory reaction. Pro-inflammatory cytokines can work with various cells of the immune system, such as neutrophils and leukocytes, to generate an immune response. Certain cytokines can function as anti-inflammatory cytokines. Anti-inflammatory cytokines refer to cytokines involved in the reduction of an inflammatory reaction. Anti-inflammatory cytokines, in some cases, can regulate a pro-inflammatory cytokine response. Some cytokines can function as both pro- and anti-inflammatory cytokines. Certain cytokines, e.g., chemokines, can function in chemotaxis. Chemokines can induce directed chemotaxis in nearby responsive cells.

In some embodiments, the expression of a cytokine having pro-inflammatory and/or chemotactic functions can be up-regulated in an immune cell. Up-regulating the expression of a cytokine having pro-inflammatory and/or chemotactic functions can be useful, for example, to stimulate an immune response against a target cell in immunotherapy.

Examples of cytokines that can be overexpressed by immune cells provided herein include, but are not limited to lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor;

transforming growth factors (TGFs) such as TGF-alpha, TGF-beta, TGF-beta1, TGF-beta2, and TGF-beta3; insulin-like growth factor-I and -II; erythropoietin (EPO); Flt-3L; stem cell factor (SCF); osteoinductive factors; interferons (IFNs) such as IFN-α, IFN-β, IFN-γ; colony stimulating factors (CSFs) such as macrophage-CSF (M-CSF); granulocyte-macrophage-CSF (GM-CSF); granulocyte-CSF (G-CSF); macrophage stimulating factor (MSP); interleukins (ILs) such as IL-1, IL-1a, IL-1b, IL-1RA, IL-18, IL-2, IL-3, IL-4, IL-5, IL-6, IL-7, IL-8, IL-9, IL-10, IL-11, IL-12, IL-13, IL-14, IL-15, IL-16, IL-17, IL-20; a tumor necrosis factor such as CD154, LT-beta, TNF-alpha, TNF-beta, 4-1BBL, APRIL, CD70, CD153, CD178, GITRL, LIGHT, OX40L, TALL-1, TRAIL, TWEAK, TRANCE; and other polypeptide factors including LIF, oncostatin M (OSM) and kit ligand (KL). Cytokine receptors refer to the receptor proteins which bind cytokines. Cytokine receptors may be both membrane-bound and soluble.

In some embodiments, the overexpressed cytokine is an interleukin (IL-1) family member (e.g., ligand), an IL-1 receptor family member, an interleukin-6 (IL-6) family member (e.g., ligand), an IL-6 receptor, an interleukin-10 (IL-10) family member (e.g., ligand), an IL-10 receptor, an interleukin-12 (IL-12) family member (e.g., ligand), an IL-12 receptor, an interleukin-17 (IL-17) family member (e.g., ligand), or an IL-17 receptor.

In some embodiments, the overexpressed cytokine is an interleukin-1 (IL-1) family member or related protein; a tumor necrosis factor (TNF) family member or related protein; an interferon (IFN) family member or related protein; an interleukin-6 (IL-6) family member or related protein; or a chemokine or related protein. In some embodiments, the cytokine is selected from IL18, IL18BP, IL1A, IL1B, IL1F10, IL1F3/IL1RA, IL1F5, IL1F6, IL1F7, IL1F8, IL1RL2, IL1F9, IL33, BAFF/BLyS/TNFSF138, 4-1BBL, CD153/CD30L/TNFSF8, CD40LG, CD70, Fas Ligand/FASLG/CD95L/CD178, EDA-A1, TNFSF14/LIGHT/CD258, TNFA, LTA/TNFB/TNFSF1, LTB/TNFC, CD70/CD27L/TNFSF7, TNFSF10/TRAIL/APO-2L(CD253), RANKL/OPGL/TNFSF11 (CD254), TNFSF12, TNF-alpha/TNFA, TNFSF13, TL1A/TNFSF15, OX-40L/TNFSF4/CD252, CD40L/CD154/TNFSF5, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, CLCF1, CNTF, IL11, IL31, IL6, Leptin, LIF, OSM, CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, and FAM19A5.

Cytokine expression can be evaluated using a variety of methods. Cytokine expression can be evaluated by assaying cell culture media (e.g., in vitro production) in which the modified immune cells are grown or sera (e.g., in vivo production) obtained from a subject having the modified immune cells for the presence of one or more cytokines. Cytokine levels can be quantified in various suitable units, including concentration, using any suitable assay. In some embodiments, cytokine protein is detected. In some embodiments, mRNA transcripts of cytokines are detected. Examples of cytokine assays include enzyme-linked immunosorbent assays (ELISA), immunoblot, immunofluorescence assays, radioimmunoassays, antibody arrays which allow various cytokines in a sample to be detected in parallel, bead-based arrays, quantitative PCR, microarray, etc. Other suitable methods may include proteomics approaches (2-D gels, MS analysis etc).

In some embodiments, the cytokine overexpressed by a modified immune cell provided herein is a chemokine. The chemokine can be, for example, a CC chemokine, a CXC chemokine, a C chemokine, and a CX3C chemokine. In some embodiments, the chemokine overexpressed by a modified immune cell is a CC chemokine selected from CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. said chemokine is a CXC chemokine selected from CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some embodiments, the chemokine overexpressed by a modified immune cell is a C chemokine selected from XCL1 and XCL2. In some embodiments, the chemokine overexpressed by an immune cell is a CX3C chemokine, and the CX3C chemokine is CX3CL1.

In an aspect, the present disclosure provides method of treating a cancer of a subject, comprising: (a) administering to a subject a modified TIL, modified T cell, or a modified immune cell of any one of the various embodiments of the aspects herein; and (b) contacting a target cell of the cancer expressing a neoantigen with the modified TIL, modified T cell, or modified immune cell under conditions that induces cytotoxicity of the modified TIL, modified T cell, or modified immune cell against the target cell of the cancer, thereby inducing death of the target cell of the cancer.

In an aspect, the present disclosure provides a method of expanding a T cell population, the method comprising: (a) providing a population of T cells comprising at least a modified immune cell of any one of the various embodiments of the aspects herein; (b) exposing the population of T cells to a B-cell surface protein to effect expansion of the population of T cells. In some embodiments, in (b), the population of T cells is exposed to a B cell comprising the B-cell surface protein.

In an aspect, the present disclosure provides a method of expanding a T cell population, comprising: (a) introducing a nucleic acid encoding a chimeric antigen receptor (CAR) into the T cell population, thereby producing a first CAR-expressing cell population, wherein the CAR comprises (i) an antigen interacting domain capable of binding a B cell surface protein; (ii) a transmembrane domain; and (iii) an intracellular signaling domain; and (b) contacting the first CAR-expressing cell population with a B cell surface protein, thereby producing an expanded and/or activated immune cell population.

In an aspect, the present disclosure provides a composition comprising one or more polynucleotides that encodes one or more of: (a) a switch molecule, wherein the switch molecule comprises an extracellular domain (ECD) of a protein that, in a unmodified immune cell, elicits an immune inactivation signal upon binding to its ligand, wherein the ECD is fused to an intracellular domain (ICD) of co-stimulatory protein that mediates an immune cell activation signal; and (b) an antigen specific T cell receptor complex, or one or more components thereof.

In an aspect, the present disclosure provides a composition comprising one or more polynucleotides that encodes one or more of: (a) an antigen specific T cell receptor complex, or one or more components thereof; and (b) a chimeric antigen receptor comprising (i) an antigen interacting domain capable of binding a B cell surface protein; (ii) a transmembrane domain; and (iii) an intracellular signaling domain.

In an aspect, the present disclosure provides a composition comprising one or more polynucleotides that encodes one or more of: (a) a switch molecule, wherein the switch molecule comprises an extracellular domain (ECD) of a protein that, in a unmodified immune cell, elicits an immune inactivation signal upon binding to its ligand, wherein said ECD is fused to an intracellular domain (ICD) of co-stimulatory protein that mediates an immune cell activation signal; (b) an antigen specific T cell receptor complex, or one or more components thereof; and (c) a chimeric antigen receptor comprising (i) an antigen interacting domain capable of binding a B cell surface protein; (ii) a transmembrane domain; and (iii) an intracellular signaling domain.

In various embodiments of the aspects herein, promoters that can be used with the compositions of the disclosure. Example promoters include those active in a eukaryotic, mammalian, non-human mammalian or human cell. The promoter can be an inducible or constitutively active promoter. Alternatively or additionally, the promoter can be tissue or cell specific.

Non-limiting examples of suitable eukaryotic promoters (i.e. promoters functional in a eukaryotic cell) can include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plant promoter. A database of plant promoters can be found (e.g., PlantProm). The expression vector may also contain a ribosome binding site for translation initiation and a transcription terminator. The expression vector may also include appropriate sequences for amplifying expression.

In various embodiments of the aspects herein, modified immune cells can specifically bind a neoantigen and/or a neoepitope. Neoantigens and neoepitopes generally refer to tumor-specific mutations that in some cases trigger an anti-tumor T cell response. For example, these endogenous mutations can be identified using a whole-exomic-sequencing approach. Tran E, et al., "Cancer immunotherapy based on mutation-specific CD4+ T cells in a patient with epithelial cancer," Science 344: 641-644 (2014). An modified immune cell (e.g., modified TIL or modified T cell) comprising a switch molecule can exhibit specific binding to a tumor-specific neo-antigen. Neoantigens bound by the immune cell can be expressed on a target cell, and for example, are encoded by mutations in an endogenous gene. In some cases, a neoantigen or neoepitope specifically bound by an immune cell can be encoded by a mutated gene. The gene can be selected from the group consisting of: ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B (encodes NY-ESO-1), DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, NY-ESO, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT. In some embodiments, the neoantigen is selected based on a genetic profile of a tumor sample from an individual. In some embodiments, the neoantigen may be selected based on a somatic mutation profile of a tumor sample from an individual.

In various embodiments of the aspects herein, a modified immune cell further comprises a kill switch. A kill switch can be activated to eliminate the immune cell in cases of severe toxicity, such as hypercytokinemia. This can happen when the immune system has such a strong response that many inflammatory cytokines are released, triggering mild to severe symptoms including fever, headache, rash, rapid heartbeat, low blood pressure, and trouble breathing. A kill switch can be a drug-inducible kill-switch. The kill switch can comprise an inducible caspase 9.

Various embodiments of the aspects herein comprise a cell, for example a modified immune cell. Cells, for example immune cells (e.g., lymphocytes including T cells and NK cells), can be obtained from a subject. Non-limiting examples of subjects include humans, dogs, cats, mice, rats, and transgenic species thereof. Examples of samples from a subject from which cells can be derived include, without limitation, skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues.

In some cases, a cell can be a population of T cells, NK cell, B cells, and the like obtained from a subject. T cells can be obtained from a number of sources, including PBMCs, bone marrow, lymph node tissue, cord blood, thymus tissue, and tissue from a site of infection, ascites, pleural effusion, spleen tissue, and tumors. In some embodiments, T cells can be obtained from a unit of blood collected from a subject using any number of techniques, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps.

Any of a variety of immune cells can be utilized in the aspects herein. In some embodiments, immune cells comprise granulocytes such as asophils, eosinophils, and neutrophils; mast cells; monocytes which can develop into macrophages; antigen-presenting cells such as dendritic cells; and lymphocytes such as natural killer cells (NK cells), B cells, and T cells. In some embodiments, an immune cell is an immune effector cell. An immune effector cell refers to an immune cell that can perform a specific function in response to a stimulus. In some embodiments, an immune cell is an immune effector cell which can induce cell death. In some embodiments, the immune cell is a lymphocyte. In some embodiments, the lymphocyte is a NK cell. In some embodiments the lymphocyte is a T cell. In some embodiments, the T cell is an activated T cell. T cells include both naive and memory cells (e.g. central memory or TCM, effector memory or TEM and effector memory RA or TEMRA), effector cells (e.g. cytotoxic T cells or CTLs or Tc cells), helper cells (e.g. Th1, Th2, Th3, Th9, Th7, TFH), regulatory cells (e.g. Treg, and Tr1 cells), natural killer T cells (NKT cells), tumor infiltrating lymphocytes (TILs), lymphocyte-activated killer cells (LAKs), αβ T cells, γδ T cells, and similar unique classes of the T cell lineage. T cells can be divided into two broad categories: CD8+ T cells and CD4+ T cells, based on which protein is present on the cell's surface. T cells expressing a subject system can carry out multiple functions, including killing infected cells and activating or recruiting other immune cells. CD8+ T cells are referred to as cytotoxic T cells or cytotoxic T lymphocytes (CTLs). CTLs expressing a subject system can be involved in recognizing and removing virus-infected cells and cancer cells. CTLs have specialized compartments, or granules, containing cytotoxins that cause apoptosis, e.g., programmed cell death. CD4+ T cells can be subdivided into four sub-sets—Th1, Th2, Th17, and Treg, with "Th" referring to "T helper cell," although additional sub-sets may exist. Th1 cells can coordinate immune responses against intracellular microbes, especially bacteria. They can produce and secrete molecules that alert and activate other immune cells, like bacteria-ingesting macrophages. Th2 cells are involved in coordinating immune responses against extracellular pathogens, like helminths (parasitic worms), by alerting B cells, granulocytes, and mast cells. Th17 cells can produce interleukin 17 (IL-17), a signaling molecule that activates immune and non-immune cells. Th17 cells are important for recruiting neutrophils.

In some embodiments, a population of immune cells provided herein can be heterogeneous. In some embodiments, cells used can be composed of a heterogeneous mixture of CD4 and CD8 T cells. The CD4 and CD8 cells can have phenotypic characteristics of circulating effector T cells. Said CD4 and CD8 cells can also have a phenotypic characteristic of effector-memory cells. In some embodiment, cells can be central-memory cells.

In some embodiments, cells include peripheral blood mononuclear cells (PBMC), peripheral blood lymphocytes (PBLs), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cell, including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be selected from a bulk population, for example, selecting T cells from whole blood. The T cells can also be expanded from a bulk population. The T cells can also be skewed towards particular populations and phenotypes. For example, the T cells can be skewed to phenotypically comprise, CD45RO (−), CCR7 (+), CD45RA (+), CD62L (+), CD27 (+), CD28 (+) and/or IL-7Rα (+). Suitable cells can be selected that comprise one of more markers selected from a list comprising: CD45RO (−), CCR7 (+), CD45RA (+), CD62L (+), CD27 (+), CD28 (+) and/or IL-7Rα (+). Cells also include stem cells such as, by way of example, embryonic stem cells, induced pluripotent stem cells, hematopoietic stem cells, neuronal stem cells and mesenchymal stem cells. Cells can comprise any number of primary cells, such as human cells, non-human cells, and/or mouse cells. Cells can be progenitor cells. Cells can be derived from the subject to be treated (e.g., patient). Cells can be derived from a human donor. Host cells can be stem memory TSCM cells comprised of CD45RO (−), CCR7 (+), CD45RA (+), CD62L+(L-selectin), CD27+, CD28+ and IL-7Rα+, said stem memory cells can also express CD95, IL-2Rβ, CXCR3, and LFA-1, and show numerous functional attributes distinctive of said stem memory cells. Host cells can be central memory TCM cells comprising L-selectin and CCR7, said central memory cells can secrete, for example, IL-2, but not IFNγ or IL-4. Cells can also be effector memory TEM cells comprising L-selectin or CCR7 and produce, for example, effector cytokines such as IFNγ and IL-4.

In various embodiments of the aspects herein, an immune cell comprises a lymphocyte. In some embodiments, the lymphocyte is a natural killer cell (NK cell). In some embodiments, the lymphocyte is a T cell. T cells can be obtained from a number of sources, including peripheral blood mononuclear cells, bone marrow, lymph node tissue, spleen tissue, umbilical cord, and tumors. In some embodiments, any number of T cell lines available can be used. Immune cells such as lymphocytes (e.g., cytotoxic lymphocytes) can preferably be autologous cells, although heterologous cells can also be used. T cells can be obtained from a unit of blood collected from a subject using any number of techniques, such as Ficoll separation. Cells from the circulating blood of an individual can be obtained by apheresis or leukapheresis. The apheresis product typically contains lymphocytes, including T cells, monocytes, granulocytes, B cells, other nucleated white blood cells, red blood cells, and platelets. The cells collected by apheresis can be washed to remove the plasma fraction and to place the cells in an appropriate buffer or media, such as phosphate buffered saline (PBS), for subsequent processing steps. After washing, the cells can be resuspended in a variety of biocompatible buffers, such as Ca-free, Mg-free PBS. Alternatively, the undesirable components of the apheresis sample can be removed and the cells directly resuspended in culture media. Samples can be provided directly by the subject, or indirectly through one or more intermediaries, such as a sample collection service provider or a medical provider (e.g. a physician or nurse). In some embodiments, isolating T cells from peripheral blood leukocytes can include lysing the red blood cells and separating peripheral blood leukocytes from monocytes by, for example, centrifugation through, e.g., a PERCOL™ gradient.

A specific subpopulation of T cells, such as CD4+ or CD8+ T cells, can be further isolated by positive or negative selection techniques. Negative selection of a T cell population can be accomplished, for example, with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate CD4+ cells, a monoclonal antibody cocktail can include antibodies to CD14, CD20, CD11b, CD16, HLA-DR, and CD8. The process of negative selection can be used to produce a desired T cell population that is primarily homogeneous. In some embodiments, a composition comprises a mixture of two or more (e.g. 2, 3, 4, 5, or more) different kind of T-cells.

In some embodiments, the immune cell is a member of an enriched population of cells. One or more desired cell types can be enriched by any suitable method, non-limiting examples of which include treating a population of cells to trigger expansion and/or differentiation to a desired cell type, treatment to stop the growth of undesired cell type(s), treatment to kill or lyse undesired cell type(s), purification of a desired cell type (e.g. purification on an affinity column to retain desired or undesired cell types on the basis of one or more cell surface markers). In some embodiments, the enriched population of cells is a population of cells enriched in cytotoxic lymphocytes selected from cytotoxic T cells (also variously known as cytotoxic T lymphocytes, CTLs, T killer cells, cytolytic T cells, CD8+ T cells, and killer T cells), natural killer (NK) cells, and lymphokine-activated killer (LAK) cells.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, a concentration of 2 billion cells/mL can be used. In some embodiments, a concentration of 1 billion cells/mL is used. In some embodiments, greater than 100 million cells/mL are used. A concentration of cells of 10, 15, 20, 25, 30, 35, 40, 45, or 50 million cells/mL can be used. In yet another embodiment, a concentration of cells from 75, 80, 85, 90, 95, or 100 million cells/mL can be used. In further embodiments, concentrations of 125 or 150 million cells/mL can be used. Using high concentrations can result in increased cell yield, cell activation, and cell expansion.

A variety of target cells can be killed using the systems and methods of the subject disclosure. A target cell to which this method can be applied includes a wide variety of cell types. A target cell can be in vitro. A target cell can be in vivo. A target cell can be ex vivo. A target cell can be an isolated cell. A target cell can be a cell inside of an organism. A target cell can be an organism. A target cell can be a cell in a cell culture. A target cell can be one of a collection of cells. A target cell can be a mammalian cell or derived from a mammalian cell. A target cell can be a rodent cell or derived from a rodent cell. A target cell can be a human cell or derived from a human cell. A target cell can be a prokaryotic cell or derived from a prokaryotic cell. A target cell can be a bacterial cell or can be derived from a bacterial cell. A target cell can be an archaeal cell or derived from an archaeal cell. A target cell can be a eukaryotic cell or derived from a eukaryotic cell. A target cell can be a pluripotent stem cell. A target cell can be a plant cell or derived from a plant cell. A target cell can be an animal cell or derived from an animal cell. A target cell can be an invertebrate cell or derived from an invertebrate cell. A target cell can be a vertebrate cell or derived from a vertebrate cell. A target cell can be a microbe cell or derived from a microbe cell. A target cell can be a fungi cell or derived from a fungi cell. A target cell can be from a specific organ or tissue.

A target cell can be a stem cell or progenitor cell. Target cells can include stem cells (e.g., adult stem cells, embryonic stem cells, induced pluripotent stem (iPS) cells) and progenitor cells (e.g., cardiac progenitor cells, neural progenitor cells, etc.). Target cells can include mammalian stem cells and progenitor cells, including rodent stem cells, rodent progenitor cells, human stem cells, human progenitor cells, etc. Clonal cells can comprise the progeny of a cell. A target cell can comprise a target nucleic acid. A target cell can be in a living organism. A target cell can be a genetically modified cell. A target cell can be a host cell.

A target cell can be a primary cell. For example, cultures of primary cells can be passaged 0 times, 1 time, 2 times, 4 times, 5 times, 10 times, 15 times or more. Cells can be unicellular organisms. Cells can be grown in culture.

A target cell can be a diseased cell. A diseased cell can have altered metabolic, gene expression, and/or morphologic features. A diseased cell can be a cancer cell, a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the target cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

Non-limiting examples of cells which can be target cells include, but are not limited to, lymphoid cells, such as B cell, T cell (Cytotoxic T cell, Natural Killer T cell, Regulatory T cell, T helper cell), Natural killer cell, cytokine induced killer (CIK) cells (see e.g. US20080241194); myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula *densa* cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus *luteum* cell of ruptured ovarian follicle, Granulosa lutein cells, Theca lutein cells, Juxtaglomerular cell (renin secretion), Macula *densa* cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

Of particular interest are cancer cells. In some embodiments, the target cell is a cancer cell. Non-limiting examples of cancer cells include cells of cancers including Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof. In some embodiments, the targeted cancer cell represents a subpopulation within a cancer cell population, such as a cancer stem cell. In some embodiments, the cancer is of a hematopoietic lineage, such as a lymphoma. The antigen can be a tumor associated antigen.

In some embodiments, the target cells form a tumor. A tumor treated with the methods herein can result in stabilized tumor growth (e.g., one or more tumors do not increase more than 1%, 5%, 10%, 15%, or 20% in size, and/or do not metastasize). In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor or the number of tumor cells is reduced by at least about 5%, 10%, 15%, 20%, 25, 30%, 35%, 40%, 45%, 50%, 55%, 60%, 65%, 70%, 75%, 80%, 85%, 90%, 95% or more. In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

Death of target cells can be determined by any suitable method, including, but not limited to, counting cells before and after treatment, or measuring the level of a marker associated with live or dead cells (e.g. live or dead target cells). Degree of cell death can be determined by any suitable method. In some embodiments, degree of cell death is determined with respect to a starting condition. For example, an individual can have a known starting amount of target cells, such as a starting cell mass of known size or circulating target cells at a known concentration. In such cases, degree of cell death can be expressed as a ratio of surviving cells after treatment to the starting cell population. In some embodiments, degree of cell death can be determined by a suitable cell death assay. A variety of cell death assays are available, and can utilize a variety of detection methodologies. Examples of detection methodologies include, without limitation, the use of cell staining, microscopy, flow cytometry, cell sorting, and combinations of these.

When a tumor is subject to surgical resection following completion of a therapeutic period, the efficacy of treatment in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%). In some embodiments, the necrosis percentage of the resected tissue is 100%, that is, no living tumor tissue is present or detectable.

Exposing a target cell to an immune cell or population of immune cells disclosed herein can be conducted either in vitro or in vivo. Exposing a target cell to an immune cell or population of immune cells generally refers to bringing the target cell in contact with the immune cell and/or in sufficient proximity such that an antigen of a target cell (e.g., membrane bound or non-membrane bound) can bind to the switch molecule expressed in the immune cell. Exposing a target cell to an immune cell or population of immune cells can also generally refer to bringing the target cell in contact with the immune cell and/or in sufficient proximity such that an antigen of a target cell (e.g., membrane bound or non-membrane bound) can bind to the CAR expressed in the immune cell. Exposing a target cell to an immune cell or population of immune cells in vitro can be accomplished by co-culturing the target cells and the immune cells. Target cells and immune cells can be co-cultured, for example, as adherent cells or alternatively in suspension. Target cells and immune cells can be co-cultured in various suitable types of cell culture media, for example with supplements, growth factors, ions, etc. Exposing a target cell to an immune cell or population of immune cells in vivo can be accomplished, in some cases, by administering the immune cells to a subject, for example a human subject, and allowing the immune cells to localize to the target cell via the circulatory system. In some cases, an immune cell can be delivered to the immediate area where a target cell is localized, for example, by direct injection.

Exposing can be performed for any suitable length of time, for example at least 1 minute, at least 5 minutes, at least 10 minutes, at least 30 minutes, at least 1 hour, at least 2 hours, at least 3 hours, at least 4 hours, at least 5 hours, at least 6 hours, at least 7 hours, at least 8 hours, at least 12 hours, at least 16 hours, at least 20 hours, at least 24 hours, at least 2 days, at least 3 days, at least 4 days, at least 5 days, at least 6 days, at least 1 week, at least 2 weeks, at least 3 weeks, at least 1 month or longer.

The various domains of switch molecules and CARs provided herein can be linked by means of chemical bond, e.g., an amide bond or a disulfide bond; a small, organic molecule (e.g., a hydrocarbon chain); an amino acid sequence such as a peptide linker (e.g., an amino acid sequence about 3-200 amino acids in length), or a combination of a small, organic molecule and peptide linker. Peptide linkers can provide desirable flexibility to permit the desired expression, activity and/or conformational positioning of the chimeric polypeptide. The peptide linker can be of any appropriate length to connect at least two domains of interest and is preferably designed to be sufficiently flexible so as to allow the proper folding and/or function and/or activity of one or both of the domains it connects. The peptide linker can have a length of at least 3, 5, 10, 15, 20, 25, 30, 35, 40, 45, 50, 55, 60, 65, 70, 75, 80, 85, 90, 95, or 100 amino acids. In some embodiments, a peptide linker has a length between about 0 and 200 amino acids, between about 10 and 190 amino acids, between about 20 and 180 amino acids, between about 30 and 170 amino acids, between about 40 and 160 amino acids, between about 50 and 150 amino acids, between about 60 and 140 amino acids, between about 70 and 130 amino acids, between about 80 and 120 amino acids, between about 90 and 110 amino acids. In some embodiments, the linker sequence can comprise an endogenous protein sequence. In some embodiments, the linker sequence comprises glycine, alanine and/or serine amino acid residues. In some embodiments, a linker can contain motifs, e.g., multiple or repeating motifs, of GS, GGS, GGGGS, GGSG, or SGGG. The linker sequence can include any naturally occurring amino acids, non-naturally occurring amino acids, or combinations thereof.

Any suitable delivery method can be used for introducing compositions and molecules (e.g., polypeptides and/or nucleic acid encoding polypeptides) of the disclosure into a host cell, such as an immune cell. The various components can be delivered simultaneously or temporally separated. The choice of method can be dependent on the type of cell being transformed and/or the circumstances under which the transformation is taking place (e.g., in vitro, ex vivo, or in vivo).

A method of delivery can involve contacting a target polynucleotide or introducing into a cell (or a population of cells such as immune cells) one or more nucleic acids comprising nucleotide sequences encoding the compositions of the disclosure. Suitable nucleic acids comprising nucleotide sequences encoding the compositions of the disclosure can include expression vectors, where an expression vector comprising a nucleotide sequence encoding one or more compositions of the disclosure is a recombinant expression vector.

Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, and nanoparticle-mediated nucleic acid delivery.

In some aspects, the present disclosure provides methods comprising delivering one or more polynucleotides, or one or more vectors as described herein, or one or more transcripts thereof, and/or one or proteins transcribed therefrom, to a host cell. In some aspects, the disclosure further provides cells produced by such methods, and organisms (such as animals, plants, or fungi) comprising or produced from such cells.

Conventional viral and non-viral based gene transfer methods can be used to introduce nucleic acids in mammalian cells or target tissues. Such methods can be used to administer nucleic acids encoding compositions of the disclosure to cells in culture, or in a host organism. Non-viral vector delivery systems can include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell.

Methods of non-viral delivery of nucleic acids can include lipofection, nucleofection, microinjection, biolistics, virosomes, liposomes, immunoliposomes, polycation or lipid:nucleic acid conjugates, naked DNA, artificial virions, and agent-enhanced uptake of DNA. Cationic and neutral lipids that are suitable for efficient receptor-recognition lipofection of polynucleotides can be used. Delivery can be to cells (e.g. in vitro or ex vivo administration) or target tissues (e.g. in vivo administration). The preparation of lipid:nucleic acid complexes, including targeted liposomes such as immunolipid complexes, can be used.

RNA or DNA viral based systems can be used to target specific cells in the body and trafficking the viral payload to the nucleus of the cell. Viral vectors can be administered directly (in vivo) or they can be used to treat cells in vitro, and the modified cells can optionally be administered (ex vivo). Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted transgene. High transduction efficiencies can be observed in many different cell types and target tissues.

The tropism of a retrovirus can be altered by incorporating foreign envelope proteins, expanding the potential target population of target cells. Lentiviral vectors are retroviral vectors that can transduce or infect non-dividing cells and produce high viral titers. Selection of a retroviral gene transfer system can depend on the target tissue. Retroviral vectors can comprise cis-acting long terminal repeats with packaging capacity for up to 6-10 kb of foreign sequence. The minimum cis-acting LTRs can be sufficient for replication and packaging of the vectors, which can be used to integrate the therapeutic gene into the target cell to provide permanent transgene expression. Retroviral vectors can include those based upon murine leukemia virus (MuLV), gibbon ape leukemia virus (GaLV), Simian Immuno deficiency virus (SIV), human immuno deficiency virus (HIV), and combinations thereof.

An adenoviral-based systems can be used. Adenoviral-based systems can lead to transient expression of the transgene. Adenoviral based vectors can have high transduction efficiency in cells and may not require cell division. High titer and levels of expression can be obtained with adenoviral based vectors. Adeno-associated virus ("AAV") vectors can be used to transduce cells with target nucleic acids, e.g., in the in vitro production of nucleic acids and peptides, and for in vivo and ex vivo gene therapy procedures.

Packaging cells can be used to form virus particles capable of infecting a host cell. Such cells can include 293 cells, (e.g., for packaging adenovirus), and Psi2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus is more sensitive than AAV. Additional methods for the delivery of nucleic acids to cells can be used, for example, as described in US20030087817, incorporated herein by reference.

A host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. In some embodiments, a cell transiently transfected with the compositions of the disclosure (such as by transient transfection of one or more vectors, or transfection with RNA) is used to establish a new cell line comprising cells containing the modification but lacking any other exogenous sequence.

Any suitable vector compatible with the host cell can be used with the methods of the disclosure. Non-limiting examples of vectors for eukaryotic host cells include pXT1, pSG5 (Stratagene™), pSVK3, pBPV, pMSG, and pSVLSV40 (Pharmacia™).

Contacting the cells with a composition of the can occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors can include polypeptides and non-polypeptide factors.

In numerous embodiments, the chosen delivery system is targeted to specific tissue or cell types. In some cases, tissue- or cell-targeting of the delivery system is achieved by binding the delivery system to tissue- or cell-specific markers, such as cell surface proteins. Viral and non-viral delivery systems can be customized to target tissue or cell-types of interest.

Pharmaceutical compositions containing molecules (e.g., polypeptides and/or nucleic acids encoding polypeptides) or immune cells described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The molecules can be packed together or separately, in a single package or in a plurality of packages. One or all of the therapeutic agents can be given in multiple doses. If not simultaneous, the timing between the multiple doses may vary to as much as about a month.

Molecules described herein can be administered before, during, or after the occurrence of a disease or condition, and the timing of administering the composition containing a compound can vary. For example, the pharmaceutical compositions can be used as a prophylactic and can be administered continuously to subjects with a propensity to conditions or diseases in order to prevent the occurrence of the disease or condition. The molecules and pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A molecule can be administered as soon as is practicable after the onset of a disease or condition is detected or suspected, and for a length of time necessary for the treatment of the disease, such as, for example, from about 1 month to about 3 months. The length of treatment can vary for each subject.

A molecule can be packaged into a biological compartment. A biological compartment comprising the molecule can be administered to a subject. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles.

For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment.

Examples of preferred amphipathic compounds used in liposomes can include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, distearoylphosphatidylcholine (DSPC), dilinoleoylphosphatidylcholine and egg sphingomyelin, or any combination thereof.

A biological compartment can comprise a nanoparticle. A nanoparticle can comprise a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers.

In some instances, as the size of the nanoparticle increases, the release rate can be slowed or prolonged and as the size of the nanoparticle decreases, the release rate can be increased.

The amount of albumin in the nanoparticles can range from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. The pharmaceutical composition can comprise up to 30, 40, 50, 60, 70 or 80% or more of the nanoparticle. In some instances, the nucleic acid molecules of the disclosure can be bound to the surface of the nanoparticle.

A biological compartment can comprise a virus. The virus can be a delivery system for the pharmaceutical compositions of the disclosure. Exemplary viruses can include lentivirus, retrovirus, adenovirus, herpes simplex virus I or II, parvovirus, reticuloendotheliosis virus, and adeno-associated virus (AAV). Pharmaceutical compositions of the disclosure can be delivered to a cell using a virus. The virus can infect and transduce the cell in vivo, ex vivo, or in vitro. In ex vivo and in vitro delivery, the transduced cells can be administered to a subject in need of therapy.

Pharmaceutical compositions can be packaged into viral delivery systems. For example, the compositions can be packaged into virions by a HSV-1 helper virus-free packaging system.

Viral delivery systems (e.g., viruses comprising the pharmaceutical compositions of the disclosure) can be administered by direct injection, stereotaxic injection, intracerebroventricularly, by minipump infusion systems, by convection, catheters, intravenous, parenteral, intraperitoneal, and/or subcutaneous injection, to a cell, tissue, or organ of a subject in need. In some instances, cells can be transduced in vitro or ex vivo with viral delivery systems. The transduced cells can be administered to a subject having a disease. For example, a stem cell can be transduced with a viral delivery system comprising a pharmaceutical composition and the stem cell can be implanted in the patient to treat a disease. In some instances, the dose of transduced cells given to a subject can be about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single dose.

Introduction of the biological compartments into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

In some embodiments, immune cells expressing a subject system are administered. Immune cells expressing a subject system can be administered before, during, or after the occurrence of a disease or condition, and the timing of administering the immune cells can vary. For example, immune cells expressing a subject system can be used as a prophylactic and can be administered continuously to subjects with a propensity to conditions or diseases in order to prevent the occurrence of the disease or condition. The immune cells can be administered to a subject during or as soon as possible after the onset of the symptoms. The administration can be initiated within the first 48 hours of the onset of the symptoms, within the first 24 hours of the onset of the symptoms, within the first 6 hours of the onset of the symptoms, or within 3 hours of the onset of the symptoms. The initial administration can be via any suitable route, such as by any route described herein using any formulation described herein. Immune cells can be administered as soon as is practicable after the onset of a disease or condition is detected or suspected, and for a length of time necessary for the treatment of the disease, such as, for example, from about 1 month to about 3 months. The length of treatment can vary for each subject.

A molecule described herein (e.g., polypeptide and/or nucleic acid) can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A molecule (e.g., polypeptide and/or nucleic acid) described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A molecule (e.g., polypeptide and/or nucleic acid) described herein can be present in a composition that provides at least 0.1, 0.5, 1, 1.5, 2, 2.5 3, 3.5, 4, 4.5, 5, 5.5, 6, 6.5, 10 or more units of activity/mg molecule. The activity can be regulation of gene expression. In some embodiments, the total number of units of activity of the molecule delivered to a subject is at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units. In some embodiments, the total number of units of activity of the molecule delivered to a subject is at most 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units.

EXAMPLES

Various aspects of the disclosure are further illustrated by the following non-limiting examples.

Example 1: Preparation of NY-ESO-1 Targeting TCR-T Cells

Tumor cells from apheresis are NY-ESO-1 positive and the patient has HLA-A:0201 leukocyte. Peripheral blood mononuclear cells (PBMCs) were isolated with Ficoll lymphocyte isolation. T cells were removed after two hour's adherent culture. NY-ESO-1 TCR lentivirus was added at multiplicity of infection (MOI) of 1. T cells were then cultured and expanded. TCR expression was determined by flow cytometry. In FIG. 1, the left panel shows TCR expression in T cells and the right panel shows expression in transduced T cells. The histogram plots in FIG. 1 indicate a greater TCR expression in the T cells with transduction of the NY-ESO-1 TCR gene.

Example 2: Preparation of Triple Positive T Cells

Tumor tissue at an amount of 10 g or more was removed from a patient. Cells were isolated via enzymatic digestion. CD3 positive T cells were isolated with CD3 magnetic beads. Other cells were grown in adherent cultures to provide tumor cells from the patient. T cells were then isolated with magnetic beads. PD-1, CD137 and TIM-3 triple positive T cells were sorted via flow cytometry and further cultured and expanded.

Example 3: Preparation of Neoantigen Reactive T Cells

Figure 2:
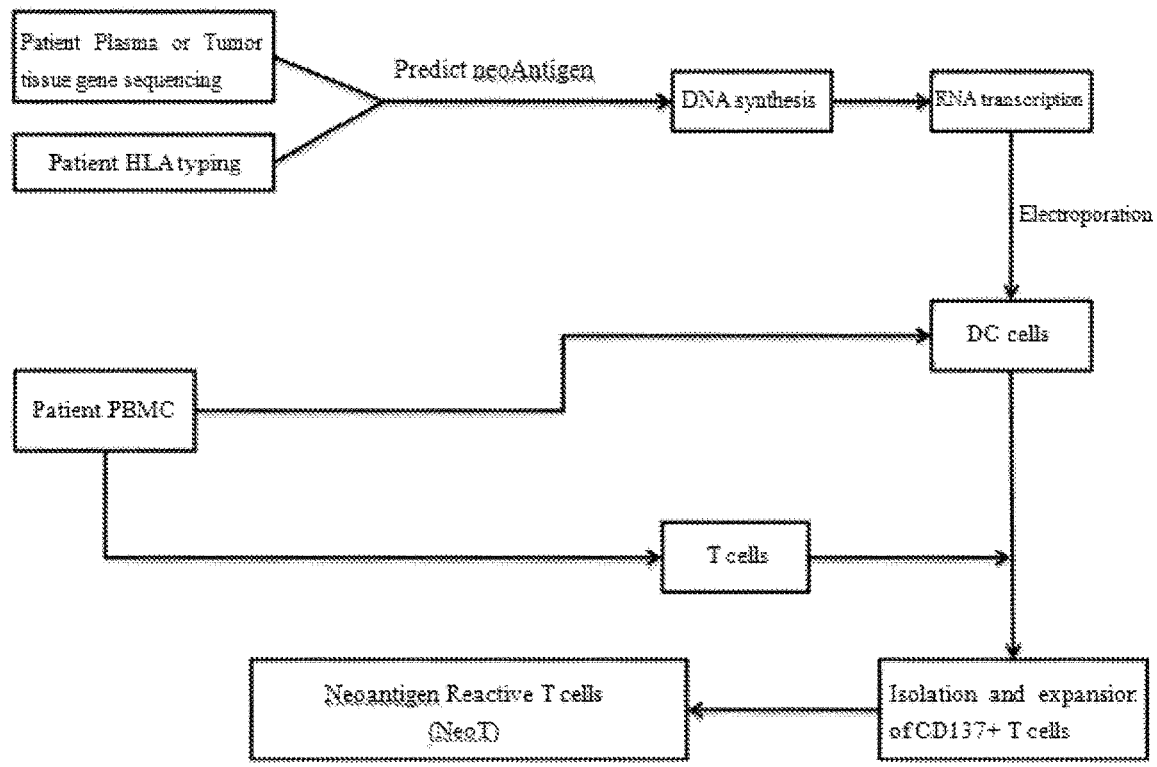
FIG. 2 illustrates a preparation process of neoantigen reactive (or recognizable) T cells.

The preparation is illustrated in FIG. 2. PBMC or tumor tissue from surgery was subject to whole exome sequencing or RNA transcriptome sequencing. 20 mutations were then selected based on affinity prediction in view of the patient's HLA typing. The gene encoding the neoantigen was synthesized and transcribed into RNA. PBMC was isolated, and subject to adherent culture for 2 hrs. Adherent monocytes were collected. Cytokines were added to promote dendritic cell differentiation and maturation. RNA was transfected into the dendritic cells via electroporation. Suspending cells were obtained mainly as T cells, and were then cultured together with the dendritic cells. CD137+ positive cells were then isolated to provide neoantigen reactive (e.g., recognizable) T cells ("neoT"). The neoTs were then expanded.

Example 4: Preparation of Lentivirus for PD1/CD28 Switch Molecule (PD1sw, SEQ ID NO.: 2

A fourth generation lentivirus vector system was used. PD1/CD28 vector, packaging vector pMDL-gag, Rev, and envelop vector pMD2.G were co-transfected into HEK293T cells with calcium phosphate or liposome-PEI. The supernatant was collected after 48 hrs, and centrifuged to concentrate the lentivirus.

Lentivirus titration was conducted on a three-fold serial dilution. HEK293T cells were collected after transduction with 50 ul lentivirus for 48 to 72 hrs, and then stained with PD-1. The percentage of PD-1+(PD-1+%) was analyzed by flow cytometry, and titration was calculated as:

Titration (TU/ml)=40000-45000(which is the number of starting HEK293T cells)*PD1$^+$%*Fold of dilution*20 (first PD1$^+$%<20%)

Figures 3A, 3B:
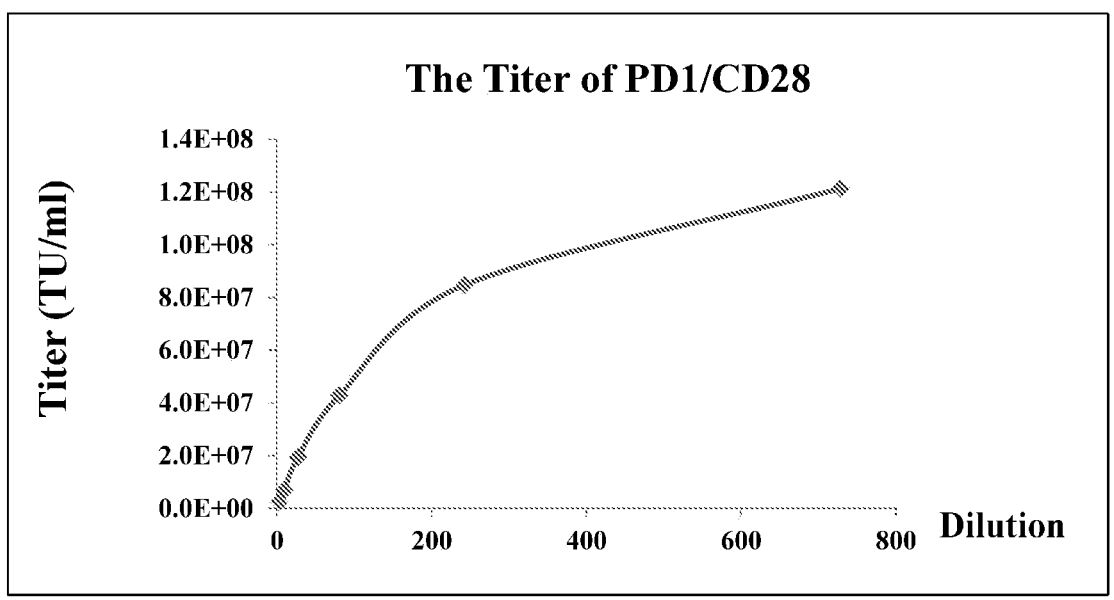
FIGS. 3A and 3B illustrate the lentivirus titration of PD1/CD28 switch molecule, wherein (a) shows the flow cytometry detection of PD1 expression; and (b) shows the titration curve.

FIGS. 3A and 3B shows calculation of PD1/CD28 lentivirus titration. Titration of over $3*10^7$ is ready for further use.

Example 5: Transduction of PD1/CD28 into Neoantigen Reactive T Cells

Figure 4:
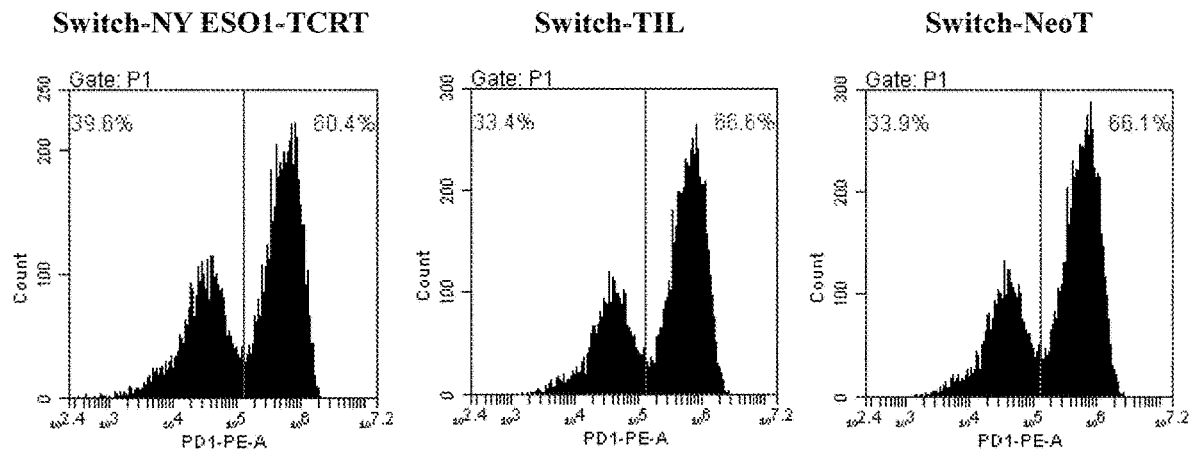
FIG. 4 illustrates the expression of PD1/CD28 switch molecule in TCR-T, TIL and neoT cells.

Three types of T cells were obtained—Switch-NY-ESO-1-TCR-T, Switch-TIL, and Switch-neoT. Switch-NY-ESO-1-TCR-T cells were obtained by expressing the Switch molecule in the ESO-1-TCR-T cells from the Example 1. Switch-TIL cells were obtained by expressing the Switch molecule in the triple positive T cell from the Example 2. Switch-neoT cells were obtained by expressing the Switch molecule in the neoT cells from the Example 3. Flow cytometry shows the expression rate of Switch to be about 60% for all three types of T cells. See FIG. 4.

Figure 5:
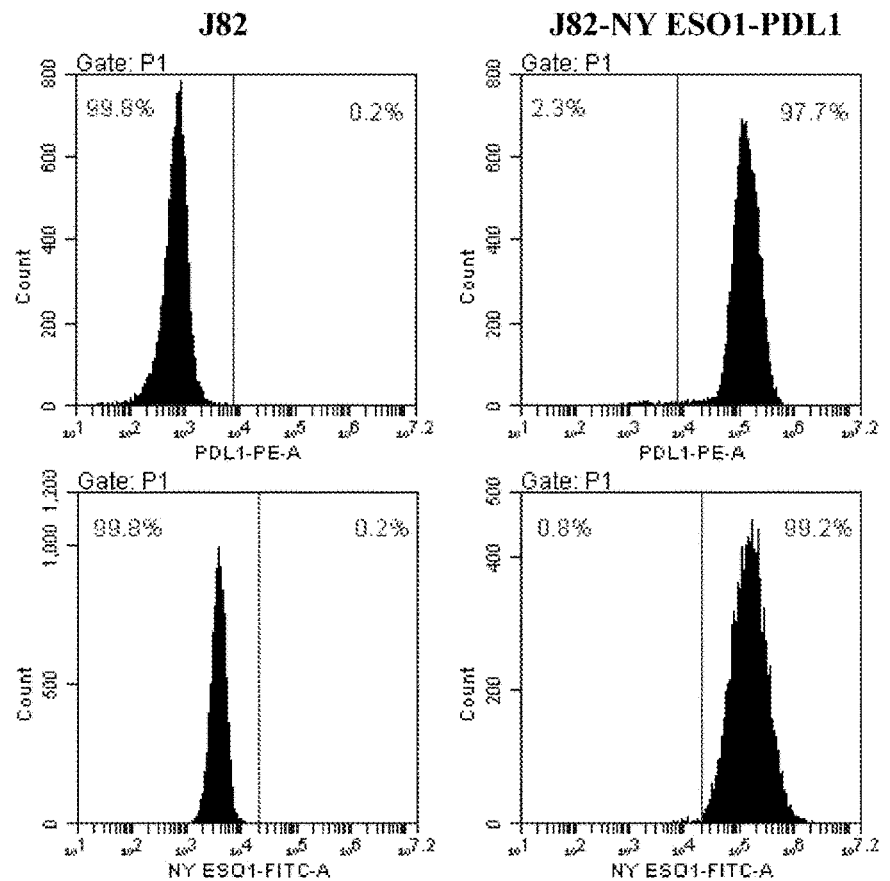
FIG. 5 illustrates assays of J82-NY-ESO-1-PDL1 bladder cancer cell line.

Example 6: In Vitro Assay of NY-ESO-1 Targeting TCR-T Cells Expressing PD1/CD28 Switch Molecule HLA typing is A:0201, J82-NY-ESO-1-PD-L1 tumor cell was constructed. Lentivirus vector was added at MOI=5 into J82 (urinary bladder, transitional cell carcinoma) to transduce PD-L1 and NY-ESO-1 transgene. G418 and Puromycin were added after 72 hr to screen positive cells. Flow cytometry was conducted to determine the expression of PD-L1 and NY-ESO-1 after about two weeks (FIG. 5). As shown in FIG. 5, over 95% of transduced J82 cells simultaneously express PDL1 and NY-ESO-1, confirming the success of cell construction. FIGS. 6A-6C shows data from an in vitro cell killing assay in which J82 or J82-NY-ESO1-PDL1 bladder cancer cells were contacted with T cells, NY-ESO1-TCR T cells, or Switch-NY-ESO1-TCR T cells. The T cells, NY-ESO1-TCR T cells, or Switch-NY-ESO1-TCR T cells were gated by the expression of CD8 and CD107a. Surface localization of the degranulation marker CD107a, also known as LAMP-1, which is normally found inside granules of T cells, is a sign of cytolytic activity as the T cells release perforin and granzymes from the granules to kill target cells. As shown in FIG. 6A, data indicates a greater cell killing ability of Switch-NY-ESO1-TCR T as compared to NY-ESO1-TCR T cells. FIGS. 6B and 6C show that an exposure to J82 bladder cancer cells does not induce secretion of IFN-γ and IL-2 in T cells, NY-ESO1-TCR T cells, or Switch-NY-ESO1-TCR T cells. On the other hand, an exposure to J82-NY-ESO1-PDL1 bladder cancer cells induces secretion of IFN-γ and IL-2 in both NY-ESO1-TCR T cells and Switch-NY-ESO1-TCR T cells, and the secretion levels of IFN-γ and IL-2 are higher in the Switch-NY-ESO1-TCR T cells.

Example 7: In Vitro Efficacy Assay of TIL Expressing PD1/CD28 Molecule

Figure 7A:
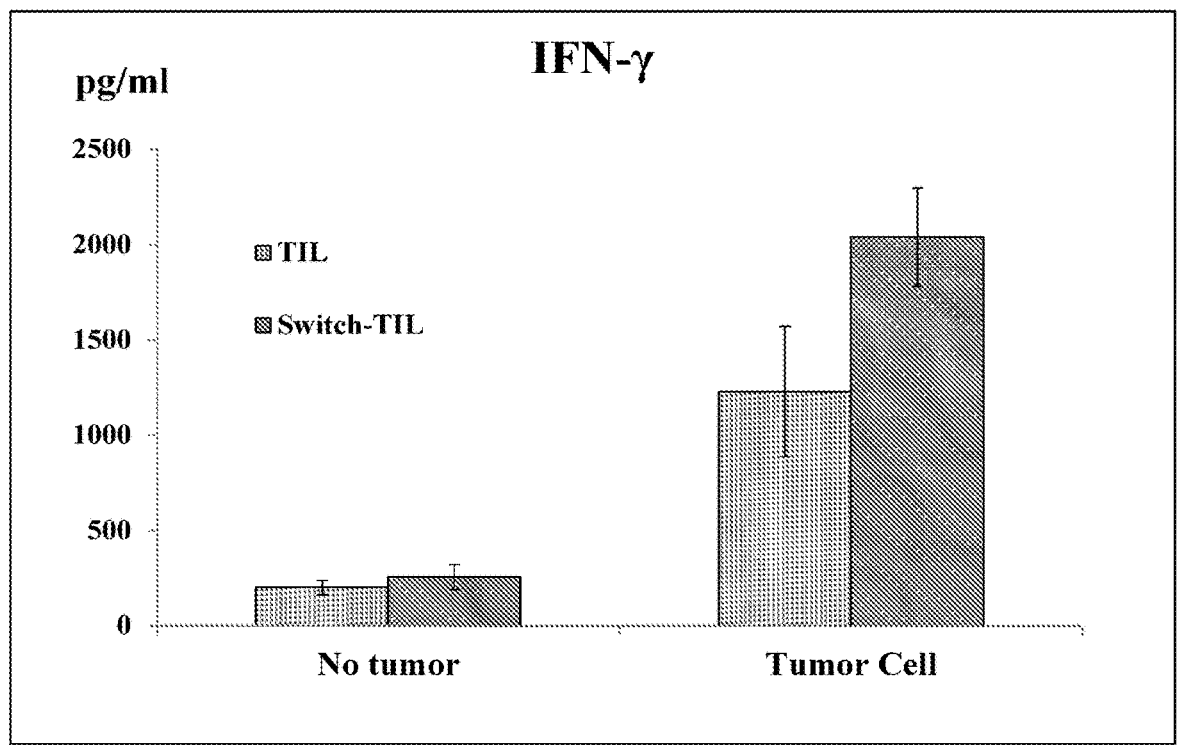
FIGS. 7A-7B illustrates the release of IFN-γ (a) and IL-2 (b) by the TIL cells, with or without the PD1/CD28 switch molecule, when cultured in the presence or absence of tumor cells.
Figure 7B:
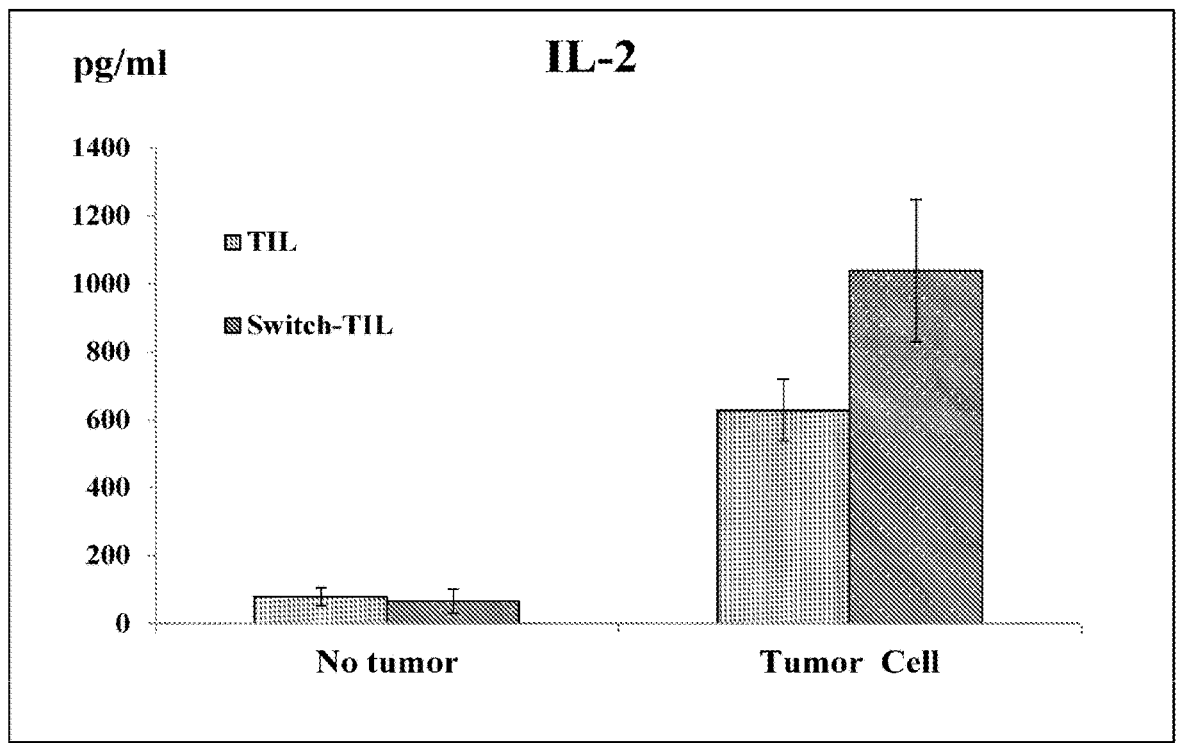

FIGS. 7A-7B show the release of IFN-γ and IL-2 in TILs (and TILs expressing PD1/CD28 switch molecule (Switch-TIL) when cultured with tumor cells. The data show that an exposure to tumor cells induces a higher secretion of IFN-γ and IL-2 by the Switch-TIL cells expressing the PD1/CD28 switch molecule than that by the TIL cells without the PD1/Cd28 switch molecule.

Example 8: In Vitro Assay of neoT Expressing PD1/CD28 Switch Molecule

Figure 8A:
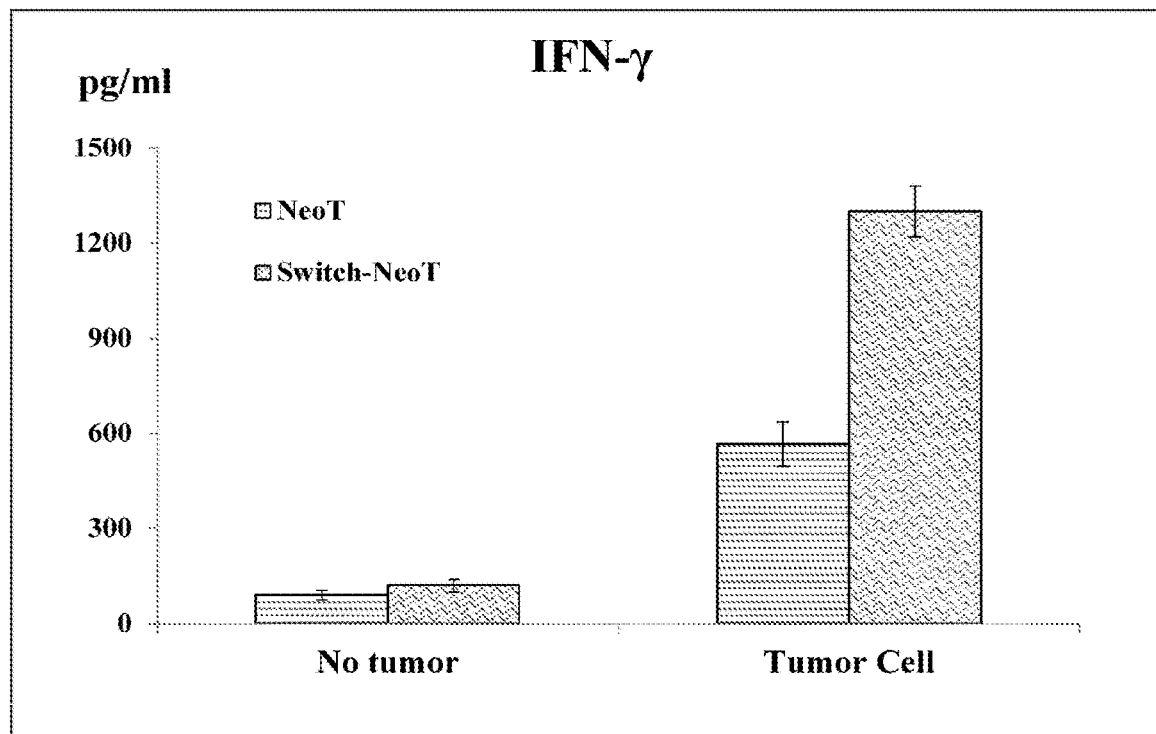
FIGS. 8A-8B illustrates the release of IFN-γ (a) and IL-2 (b) in the neoantigen reactive T cells (neoT), with or without the PD1/CD28 switch molecule, when cultured in the presence of absence of tumor cells.
Figure 8B:
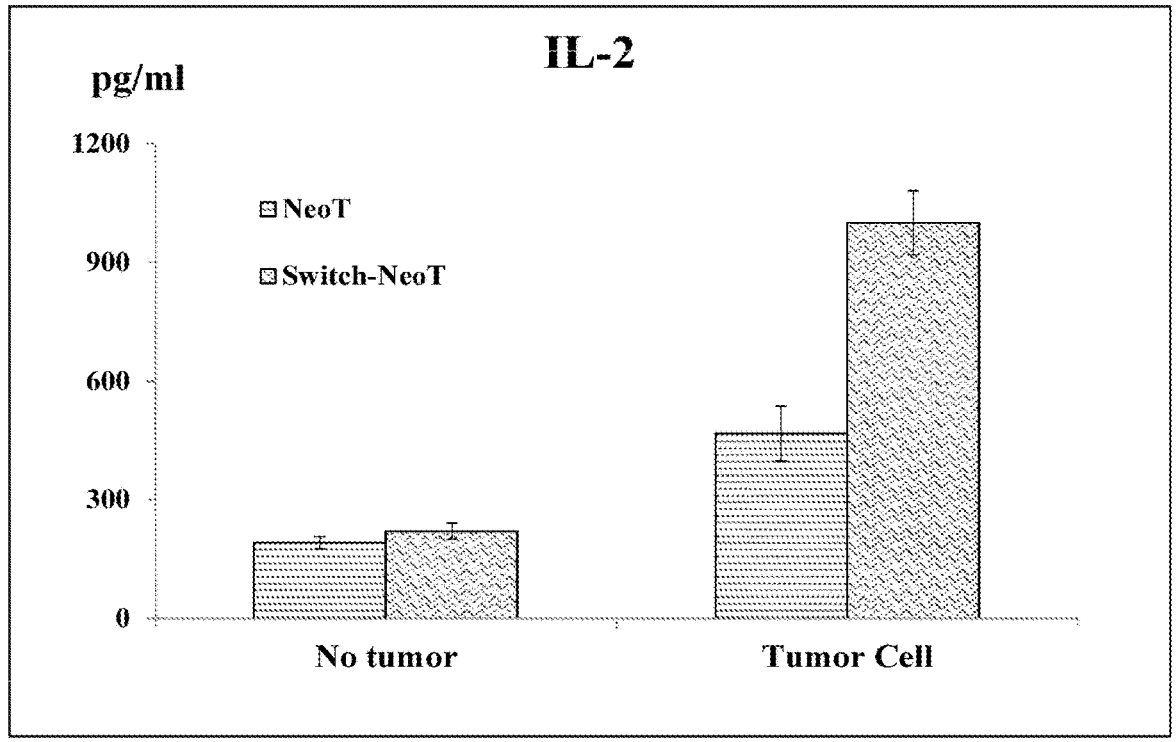

FIGS. 8A-8B show the release of IFN-γ and IL-2 in neoantigen reactive T cells (neoT) and neoT cells expressing PD1/CD28 switch molecule (Switch-neoT) when cultured with tumor cells. The data show that an exposure to tumor cells induces a higher secretion of IFN-γ and IL-2 by the Switch-neoT cells expressing the PD1/CD28 switch molecule than that by the neoT cells without the PD1/CD28 switch molecule.

Example 9: Animal Study on NY-ESO-1 TCR-T Cells Expressing PD1/CD28 Switch $1*10^6$ tumor cells, J82-NY-ESO-1-PD-L1, are subcutaneously inoculated into NSG mice. Tumor is expected to be developed after about two weeks. Tumor sizes are measured at week 23, and 30 mice are used.

Mice in control group are treated with PBS, subcutaneous injection (A0). There are 5 treatment groups: non-treatment group PBS (A1), T cell (A2), Switch-T cell (A3), NY-ESO-1 TCR-T cell group (A4) and Switch-NY-ESO-1 TCR T group (A5). Cells are given by intravenous injection of $1*10^7$ cells into tail vein.

Tumor size is measured every 2-3 days for 30 days, and general status of mice is observed. Tumor size is determined according to the formula Tumor size=½*long diameter*short diameter*short diameter.

The experiment is expected to demonstrate that tumor size of group A5 decreases, or remain more or less constant or at least the rate of increase is decreased as compared to that of groups A1-A3.

The amount of T cell at the tumor site after treatment is analyzed: Mice are chosen randomly from each of the treatment groups A3-A5 on day 10 after administration, and tumor tissue is isolated to provide TILs. Flow cytometry is conducted to measure the total amount of T cells present at the tumor site. It is expected that the treatment with the Switch-NY-ESO-1 TCR T cells (A5) results in a greater presence of T cells at the tumor site.

Example 10: Preparation of Lentivirus CAR Targeting B Cell Surface Protein (BCAR CD19 was chosen as a B-CAR target, and an antigen binding domain comprising the sequence as shown in SEQ ID NO.:1 was used to construct the B-CAR. A fourth generation lentivirus vector system was used. CA19 CAR vector, packaging vector pMDL-gag, Rev, and envelop vector pMD2.G were co-transduced into HEK293T cells with calcium phosphate or liposome-PEI. The supernatant was collected after 48 hrs, and ultra-centrifuged to concentrate the lentivirus.

CD19 lentivirus titration was conducted on a three-fold serial dilution. 293T cells were collected after transduced with 50 ul lentivirus for 48 to 72 hrs, and then stained for CAR expression. The percentage of CAR+ (CAR+%) was analyzed via flow cytometry, and titration calculated as:

Titration (TU/ml)=(Number of starting 293T cells) *CAR+%*Fold of dilution*20 (first CAR+ %<20%)

Lentivirus titration was calculated. Titration over $3*10^7$ was considered ready for further use.

Example 11: Transduction of BCAR into Tumor Recognizable T Cells

Figure 9:
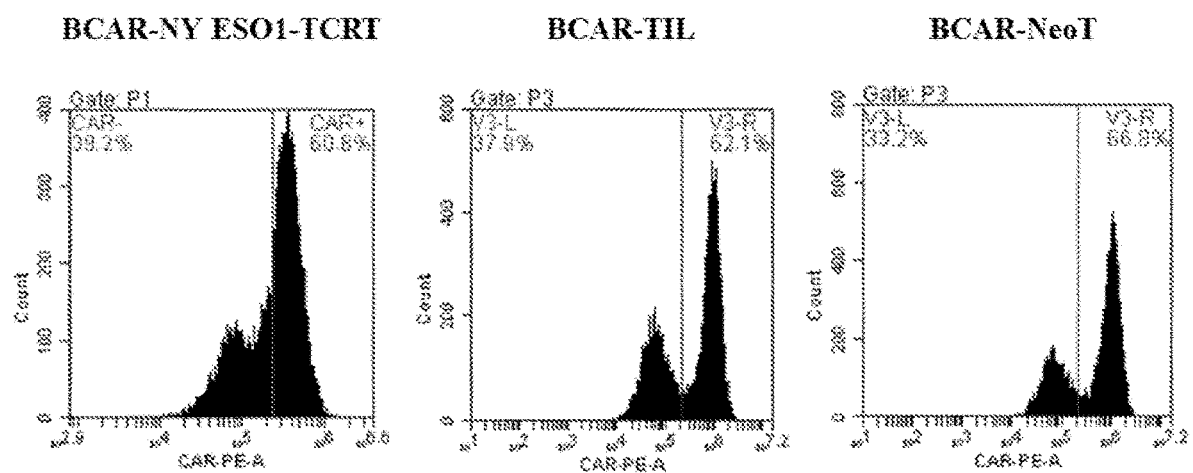
FIG. 9 shows the expression of chimeric antigen receptor targeting B cell surface protein (BCAR) in TCR-T, TILs and NeoT.

Three types of T cells were obtained by transducing NY-ESO1-TCR T cells, TILs, and neoT with BCAR lentivirus (BCAR-NY-ESO-1-TCR-T, BCAR-TIL, and BCAR-neoT). Flow cytometry showed the expression of B-CAR to be about 60% for all three types of T cells. See FIG. 9. The three types of T cells were expanded separately.

Example 12: In Vitro Assay on NY-ESO1 TCR-T Cells Expressing BCAR

Figure 10:
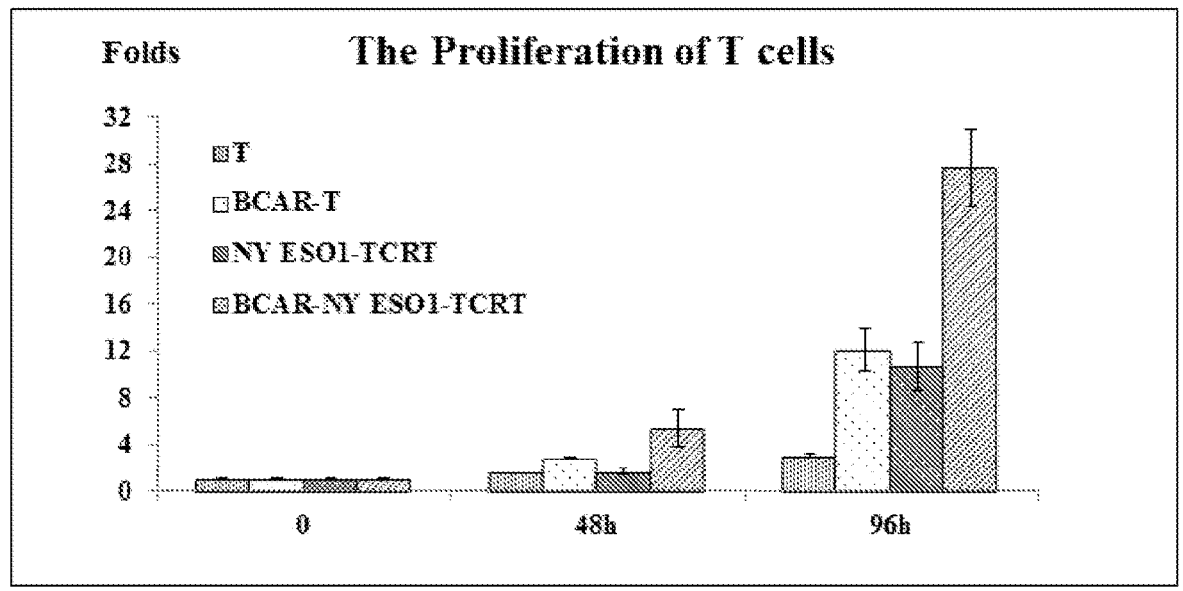
FIG. 10 illustrate the in vitro efficacy and expansion of NY-ESO1-TCR-T cells expressing BCAR.

To confirm the function of BCAR in the NY-ESO-1 targeting TCR-T cells, J82-NY-ESO-1-Luc tumor cell line having HLA type A:0201 was constructed. To confirm the dual targeting function of BCAR-NY ESO1-TCR-T cells, 1*10$^5$ J82-NY-ESO-1-Luc cells were seeded into a 24-well plate and cultured overnight allowing adherence. The cells were divided into four groups—A, B, C, and D—and each well also contained 5*10$^4$ B cells. Group A was co-cultured with 2*10$^5$ T cells. Group B was co-cultured with 2*10$^5$ BCAR-T cells (CAR positive rate 60%). Group C was co-cultured with 2*10$^5$ NY-ESO1-TCR-T cells. Group D was co-cultured with 2*10$^5$ BCAR-NY-ESO1-TCR-T cells. The following assays were conducted:

Expansion of T cells. The number of T cells was counted after culture for 48 h and 96 h. As shown in FIG. 10, after 4 days of culture, T cells of Group A expanded about 3-fold; BCAR-T cells of Group B expanded about 12-fold; NY-ESO1-TCR-T cells of Group C expanded about 10-fold; and BCAR-NY-ESO1-TCR-T cells expanded about 27-fold.

Figure 11:
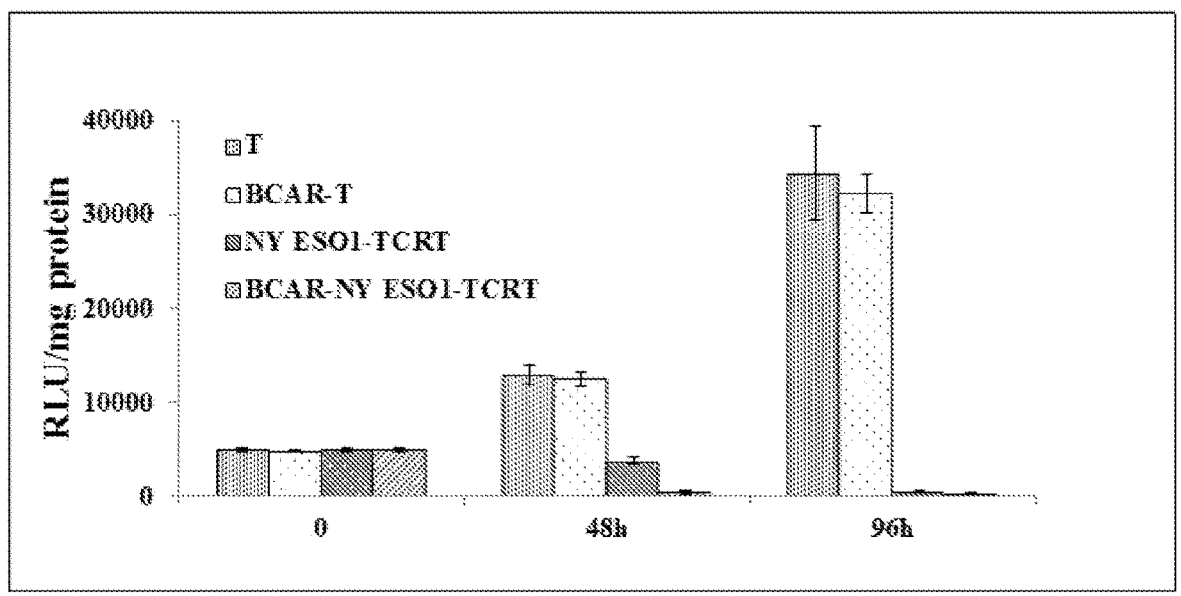
FIG. 11 illustrate the in vitro efficacy and expansion of NY-ESO1-TCR-T cells expressing BCAR.

Growth of tumor cells. Supernatant was removed from the cultures of Groups A-D after 48 h and 96 h. The culture was then rinsed with PBS 3 times. The adherent tumor cells were lysed, and luciferase activity was measured as an indication of the survival rate of tumor cells. See FIG. 11. The data show that, after culture for 48 h, the average amount of proteins from the tumor cells (thus the number of tumor cells present) is the lowest for the treatment with the BCAR-NY-ESO1-TCR-T cells relative to the other treatments.

Example 13: In Vitro Assay on TIL Expressing BCAR

Figure 12A:
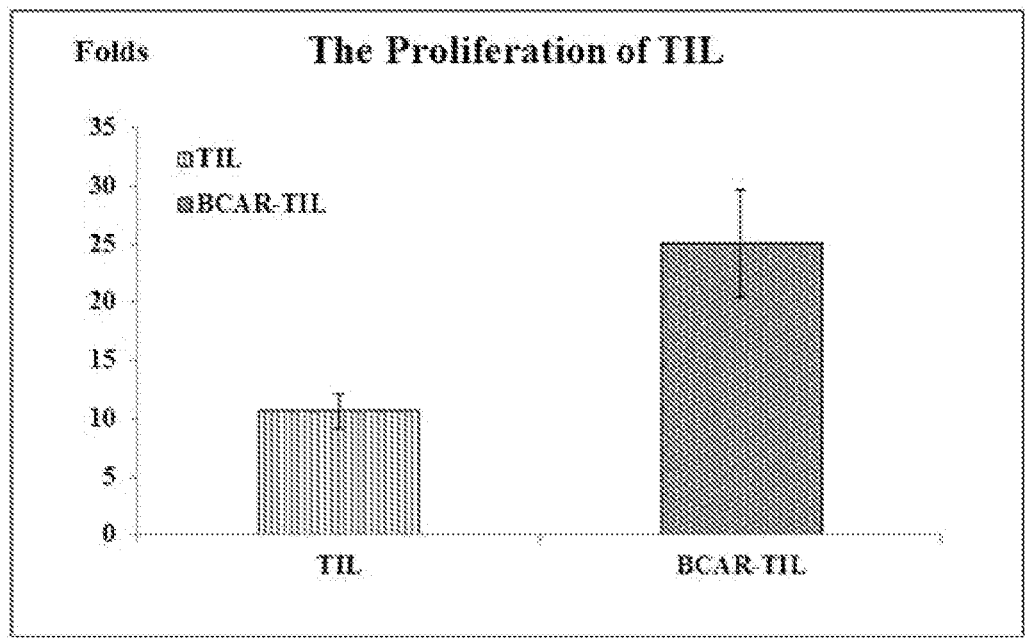
FIGS. 12A and 12B illustrate the in vitro efficacy and expansion of TILs expressing BCAR.

To confirm the function of CD19 CAR (BCAR) in TILs, tumor cells were isolated from human subject fresh tumor tissues and seeded into 24-well plate. The cells were cultured overnight allowing adherence. Into the wells, TILs and BCAR-TILs were added. The same amount of B cells were added to the wells, and the following assays were conducted:

Expansion of T cells. After 96 hours of co-culture with tumor cells, TILs expanded about 10-fold, while BCAR-TILs expanded about 25-fold, as shown in FIG. 12A. The result show greater expansion of BCAR-TILs compared to TILs lacking BCAR when co-cultured with B cells and tumor cells.

Figure 12B:
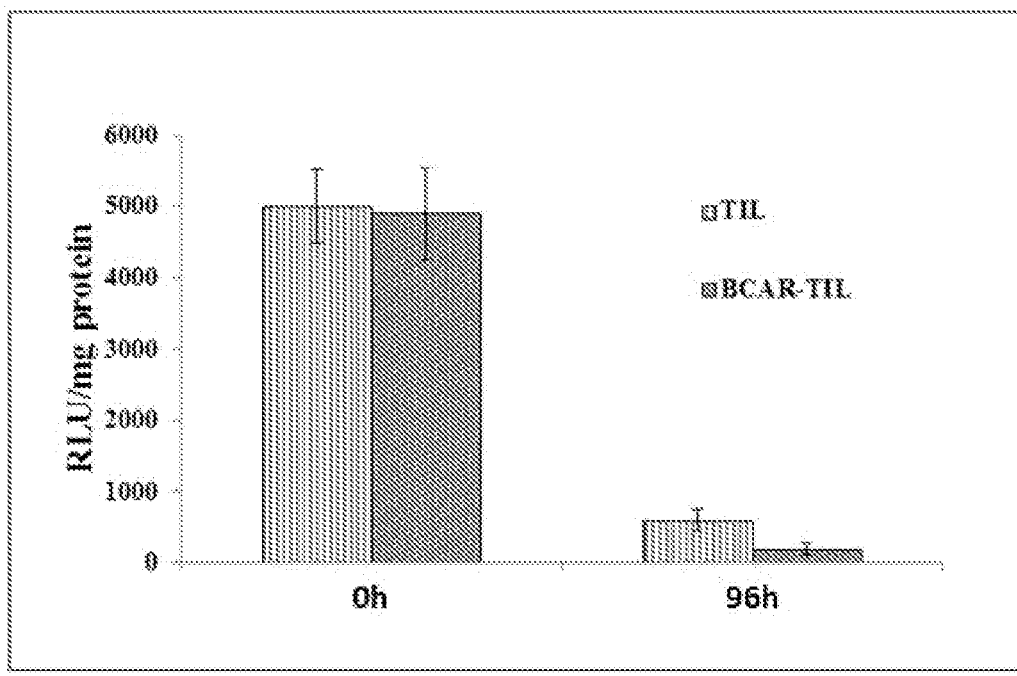

Growth of Tumor cells. Supernatant was removed from the culture mixture after 96 hours. The culture was then rinsed 3 times with PBS. Adherent tumor cells were lysed and luciferase activity was measure as an indication of tumor cell survival. Luciferase levels are shown in FIG. 12B. The data show that, after culture for 96 h, the average amount of proteins from the tumor cells (thus the number of tumor cells present) is lower when treated with the BCAR-TIL cells than when treated with the TIL cells lacking BCAR.

Example 14: In Vitro Assay on Neoantigen Reactive T Cells Expressing BCAR

Figure 13A:
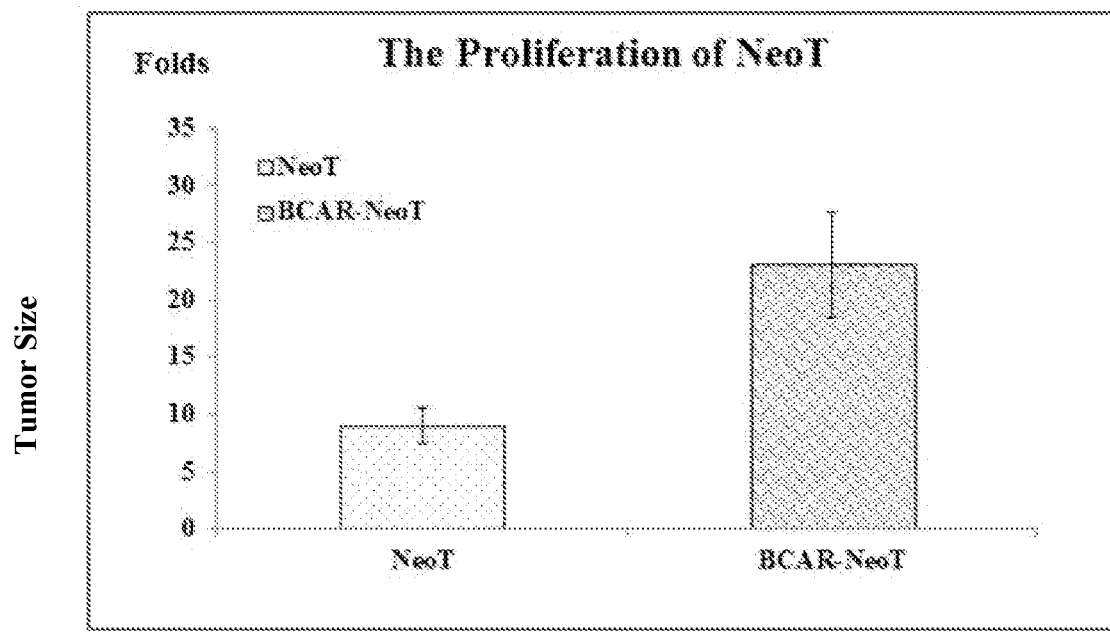
FIGS. 13A and 13B illustrate the in vitro efficacy and expansion of NeoT expressing BCAR.

To confirm the function of CD19CAR (e.g., BCAR) in neoT cells, tumor cells were isolated from human subject fresh tumor tissues and seeded into a 24-well plate. The cells were cultured overnight allowing adherence. Into the culture, neoT and BCAR-neoT cells were added. The same amount of B cells was added to the wells, and the following assays were conducted:

Expansion of T cells. After 96 hours of co-culture with tumor cells, neoT cells expanded about 9-fold, while BCAR-neoT expanded about 23-fold, as shown in FIG. 13A. The result show greater expansion of BCAR-neoT cells compared to neoT cells lacking BCAR when co-cultured with B cells and tumor cells.

Figure 13B:
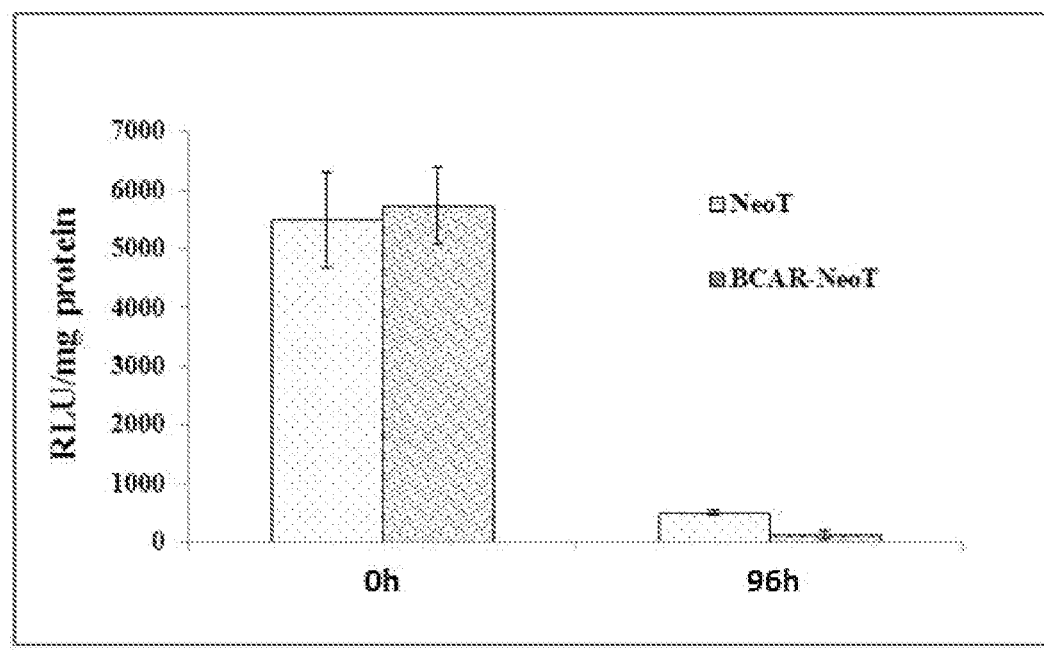

Growth of Tumor cells. Supernatant was removed from the culture mixture after 96 hours. The culture was then rinsed 3 times with PBS. Adherent tumor cells were lysed and luciferase activity was measured as an indication of tumor cell survival. Luciferase levels are shown in FIG. 13B. The data show that, after culture for 96 h, the average amount of proteins from the tumor cells (thus the number of tumor cells present) was lower when treated with the BCAR-neoT cells than when treated with the neoT cells lacking BCAR.

Example 15: Animal Test on NY-ESO-1 TCR-T Cells Expressing BCAR

Animal Model: 1*10$^6$ tumor cells (J82-NY-ESO-1) are subcutaneously injected to NSG mice. As blank control, animals of Group A0 are subcutaneously injected with PBS. Tumor form in animals about two weeks after injection of tumor cells. Tumor size is measured at Day 23. 30 mice are selected.

Administration: Blank control (A0) group animals are injected with PBS via tail vein. Tumor bearing groups are divided into 6 groups: PBS group (A1); T cell group (A2); BCAR-T group (A3); NY-ESO-1 TCR-T group (A4); BCAR & NY-ESO-1 TCR T dual targeting T cell group (A5); and NY-ESO-1 TCR T at higher dose group (A6). Animals of Groups A1-A5 are infused with 1*10$^4$ T cells via tail vein; Group A6 with 1*10$^7$. All groups are given 1*10$^7$ B cells via infusion.

Tumor size and health status of the mice are measured every 2-3 days for 28 days after administration. Tumor size is calculated as:

Tumor size=½*long_diameter*short_diameter*short_diameter

Change in Tumor Burden

This experiment is expected to demonstrate that the group 5 mice exhibit least tumor size amongst all other groups.

Change in Total Amount of the Infused T Cells

Peripheral blood is extracted at day 10 after administration from animals of Groups A2-A5. The total number of CD3+ T cells is measured with flow cytometry, expected to demonstrate that the number of T cells in BCAR bearing Group A3 and A5 are more than that of Group A4. Both the BCAR T cells and the dual targeting T cells are expected to expand in vivo.

Example 16: Animal Test on TILs Expressing BCAR

Animal Model: tumor cells are isolated from fresh tumor tissues, and are subcutaneously injected to NSG mice at an amount of 1*10$^6$ per animal. As blank control, animals of Group A0 were s.c injected with PBS. Tumor forms in animals about two weeks after injection of tumor cells. Tumor size is measured at Day 25. 30 mice are selected.

Administration: Blank control (A0) group animals are injected with PBS via tail vein. Tumor bearing groups are divided into 5 groups: PBS group (A1); T cell group (A2); BCAR-T group (A3); TILs group (A4); and BCAR TILs group (A5). Animals of Groups A1-A5 are infused with 1*10$^4$ T cells via tail vein, and all groups are given 1*10$^7$ B cells via infusion.

Tumor size and health status of the mice are measured every 2-3 days for 28 days after administration. Tumor size is calculated as:

Tumor size=½*long_diameter*short_diameter*short_diameter.

Change in Tumor Burden

This experiment is expected to demonstrate that the group 5 mice exhibit least tumor size amongst all other groups Change in Total Amount of the Infused T Cells Peripheral blood is extracted at day 10 after administration from animals of Groups A2-A5. The total number of CD3+ T cells are measured with flow cytometry, demonstrating that the number of T cells in BCAR bearing Groups A3 and A5 are more than that of Group A4. It shows that both BCAR T cells and the dual targeting T cells are expanded in vivo.

Example 17: Animal Test on neoTs Expressing BCAR

Animal Model: tumor cells are isolated from fresh tumor tissues and are subcutaneously injected to NSG mice at an amount of $1*10^6$ cells per animal. As blank control, animals of Group A0 are s.c injected with PBS. Tumors form in animals about two weeks after injection of tumor cells. Tumor size is measured at Day 25. 30 mice were selected.

Administration: Blank control (A0) group animals are injected with PBS via tail vein. Tumor bearing groups are divided into 6 groups: PBS group (A1); T cell group (A2); BCAR-T group (A3); normal neoT group (A4); BCAR neoT group (A5); and normal neoT cell at higher dose group (A6). Animals of Groups A1-A5 are infused with $1*10^4$ T cells via tail vein while those of Group A6 were infused with $1*10^7$ T cells via tail vein, and all groups were given $1*10^7$ B cells via infusion.

Tumor size and health status of the mice are measured every 2-3 days for 28 days after administration. Tumor size is calculated as:

Tumor size=½*long_diameter*short_diameter*short_diameter

Change in Tumor Burden

The experiment is expected to demonstrate that tumor size of groups A4, A5 and/or A6 is smaller as compared to that of the control A1, A2 and/or A3 groups.

Change in Total Amount of the Infused T Cells

Peripheral blood is extracted at day 10 after administration from animals of Groups A2-A5. The total number of CD3+ T cells is measured with flow cytometry, expected to indicate that the number of T cells in BCAR bearing Groups A3 and A5 is more than that of Group A4. It shows that both BCAR T cells and the dual targeting T cells are expanded in vivo.

Example 18: Preparation of Lentivirus Vector for Three Switch Molecules

Three switch molecules PD1/CD28 (hereinafter PD1sw, SEQ ID NO.: 2), TIM3/CD28 (hereinafter PD1sw, SEQ ID NO.: 3), and TGFBR2/CD28 (hereinafter TGFBR2sw, SEQ ID NO.: 4) were constructed. Extracellular domains of PD1, TIM3 and TGFBR2 were used as immune inhibitory protein of each switch molecules, while CD28 was used as the co-stimulatory signaling protein.

Taking PD1sw as an example, the fourth generation of lentivirus vector system was used. PD1/CD28 vector, packaging vector pMDL-gag, Rev, and envelop vector pMD2.G were co-transfected into HEK293T cells with calcium phosphate or liposome-PEI. The supernatant was collected after 48 hrs, and ultra-centrifuged to concentrate the lentivirus.

PD1sw lentivirus titer was determined with three-fold serial dilution. HEK293T cells were collected after transduced with 50 ul lentivirus for 48 to 72 hrs, and then stained with PD-1. The percentage of PD1+ (CAR+%) cells was analyzed via flow cytometry, and titer calculated as:

Titer (TU/ml)=(Number of starting 293T cells)*PD1+%*Fold of dilution*20 (first PD1+ %<20%)

Lentivirus titer was calculated. Titer over $3*10^7$ was considered ready for further use.

TIM3sw and TGFBR2sw were prepared with similar methods.

Example 19: Preparation of Lentivirus Vector Loaded with Switch+BCAR

Lentivirus vectors were constructed for PD1sw-2A-CD19 CAR (hereinafter "PD1sw-BCAR"), TIM3sw-2A-CD19 CAR (hereinafter "TIM3sw-BCAR"), TGFBR2sw-2A-CD19 CAR ("TGFBR2sw-BCAR) respectively according to the method of Example 18.

Example 20: Transduction of Vectors for Switches and BCARs into TILs and pTILs The lentivirus for the switches and BCARs of Example 19 and their combinations were transduced into the TILs and peripheral TILs (pTILs). The following cells were generated:

(1) TILs
1. PD1sw-TIL (PD1sw lentivirus transduced into TILs);
2. TIM3sw-TIL (TIM3sw lentivirus transduced into TILs);
3. TGFBR2sw-TIL (TGFBR2sw lentivirus transduced into TILs);
4. BCAR-TIL (CD19 CAR lentivirus transduced into TILs);
5. PD1sw-BCAR-TIL (PD1sw-CD19 CAR lentivirus transduced into TILs to provide SuperTILs, hereinafter, "PD1-STILs");
6. TIM3sw-BCAR-TIL (TIM3sw-CD19 CAR lentivirus transduced into TILs to provide SuperTILs, hereinafter, "TIM3-STIL");
7. TGFBR2sw-BCAR-TIL (TGFBR2sw-CD19 CAR lentivirus transduced into TILs to provide SuperTILs, hereinafter, "TGFBR2-STIL");
8. PD1-STIL, TIM3-STIL, and TGFBR2-STIL SuperTILs were mixed together to give "XSTIL"

(2) pTILs:
1. PD1sw-pTIL (PD1sw lentivirus transduced into pTILs);
2. TIM3sw-pTIL (TIM3sw lentivirus transduced into pTILs);
3. TGFBR2sw-pTIL (TGFBR2sw lentivirus transduced into pTILs);
4. BCAR-pTIL (CD19 CAR lentivirus transduced into pTILs);
5. PD1sw-BCAR-pTIL (PD1sw-CD19 CAR lentivirus transduced into pTILs to provide Super-pTILs, hereinafter, "PD1-SpTIL");
6. TIM3sw-BCAR-pTIL (TIM3sw-CD19 CAR lentivirus transduced into pTILs to provide Super-pTILs, hereinafter, "TIM3-SpTIL");
7. TGFBR2sw-BCAR-pTIL (TGFBR2sw-CD19 CAR lentivirus transduced into pTILs to provide Super-pTILs, hereinafter, "TGFBR2-SpTIL");
8. PD1-SpTIL, TIM3-SpTIL and TGFBR2-SpTIL were mixed together to give "XSpTIL"

It is understood that the Super-pTILs are also SuperTILs. Super-pTILs were particularly named in order to specify a different origin of the cells.

(1) Preparation of PD1sw-TILs/pTILs:

Based on the PD1sw lentivirus titer, the lentivirus were added into TILs/pTILs at MOI=5. Flow cytometric assay was conducted to sort out PD1sw-TILs/pTILs to have an expression rate of PD1 of about 60%.

TIM3sw-TIL/pTIL, TGFBR2sw-TIL/pTIL and BCAR-TIL/pTIL were prepared by similar methods.

Figure 14:
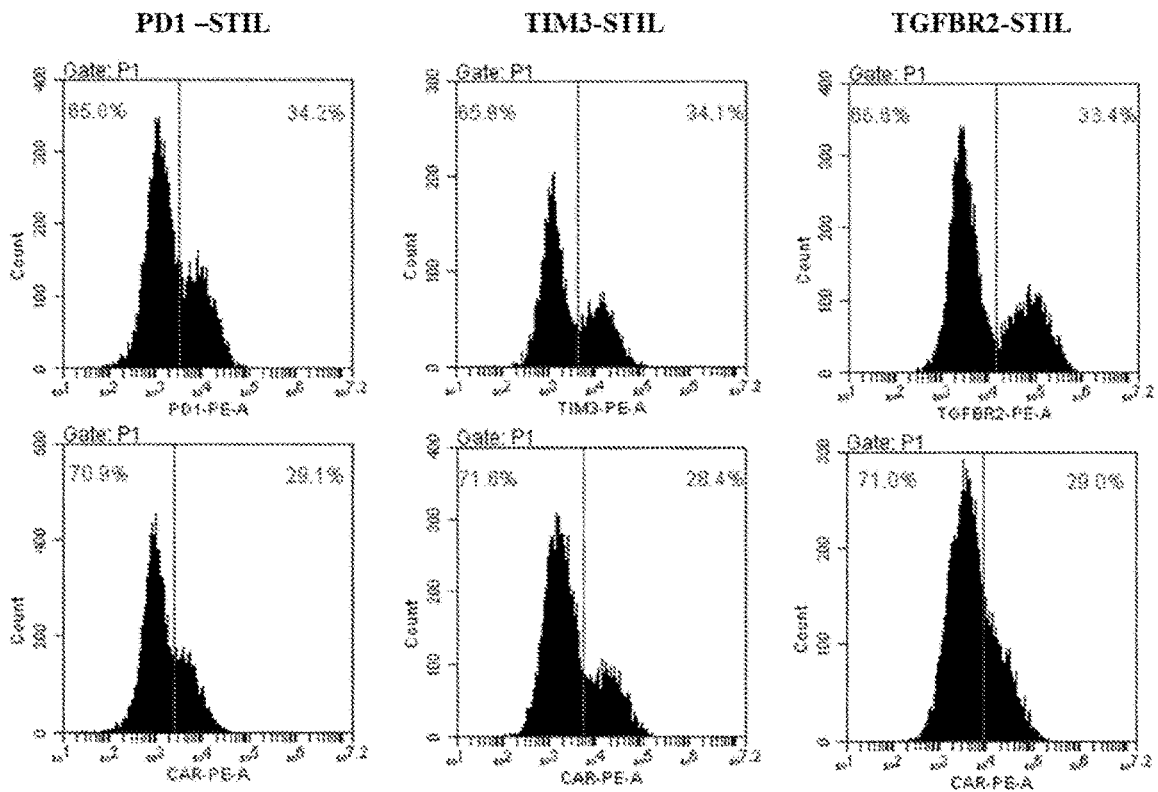
FIG. 14 illustrates expression of PD1sw-BCAR, TIM3sw-BCAR and TGFBR2sw-BCAR in TILs.
Figure 15:
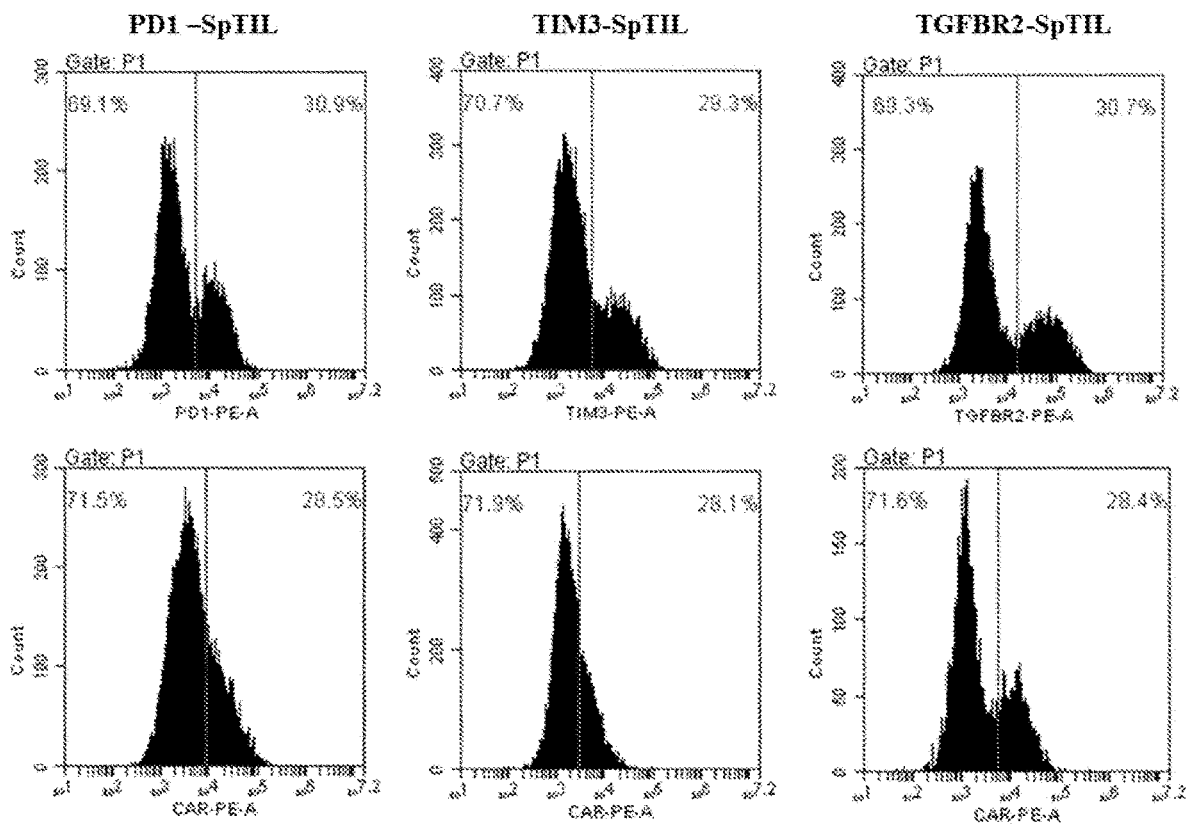
FIG. 15 illustrates expression of PD1sw-BCAR, TIM3sw-BCAR and TGFBR2sw-BCAR in pTILs.

(2) Preparation of PD1-STIL/SpTILs:

Based on the PD1sw-CD19 CAR lentivirus titer, the lentivirus were added into TILs/pTILs at MOI=5. Flow cytometric assay was conducted to sort out PD1+ cells to provide PD1-STILs/SpTILs which have an expression rate of PD1 and CD19 CAR of about 30% (FIGS. 14 and 15).

TIM3-STIL/SpTIL, and TGFBR-STIL/SpTIL were prepared with similar methods as PD1-STIL/SpTIL.

(3) Preparation of XSTIL/XsTIL

PD1-STIL/SpTIL, TIM3-STIL/SpTIL and TGFBR-STIL/SpTIL were mixed according to a certain ratio, with each of them comprised of 0-100% respectively. In this example, the ratio is 1:1:1.

Example 21: In Vitro Assay on SuperTIL Efficacy

In order to confirm the SuperTILs efficacy, efficacy is observed separately when B cells are not added and when B cells are added.

(1) Comparison of Tumor Killing Effect when No B Cells are Added.

Figure 16A:
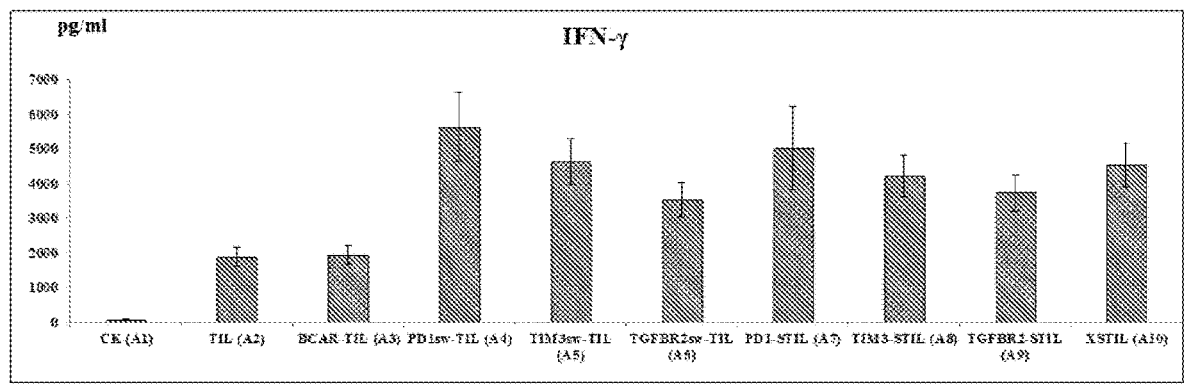
FIGS. 16A and 16B illustrate release of IFN-γ and IL-2 from different TILs without B cells.
Figure 16B:
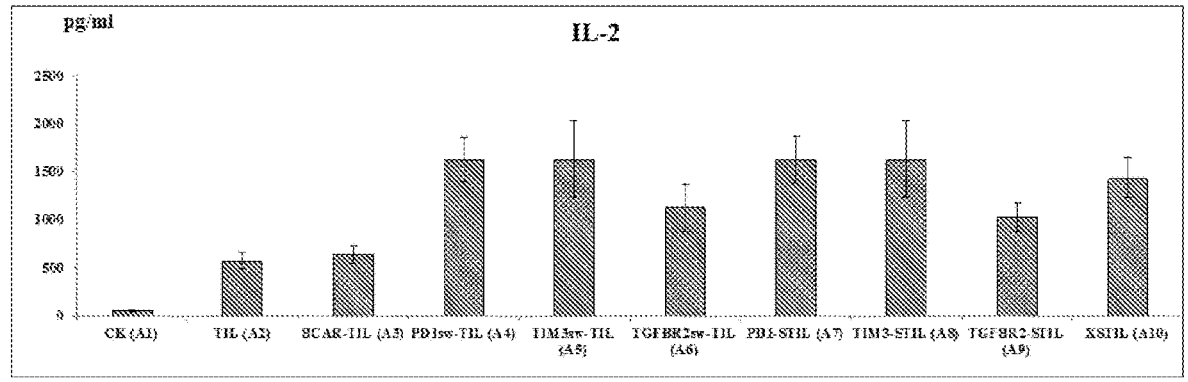
Figure 17A:
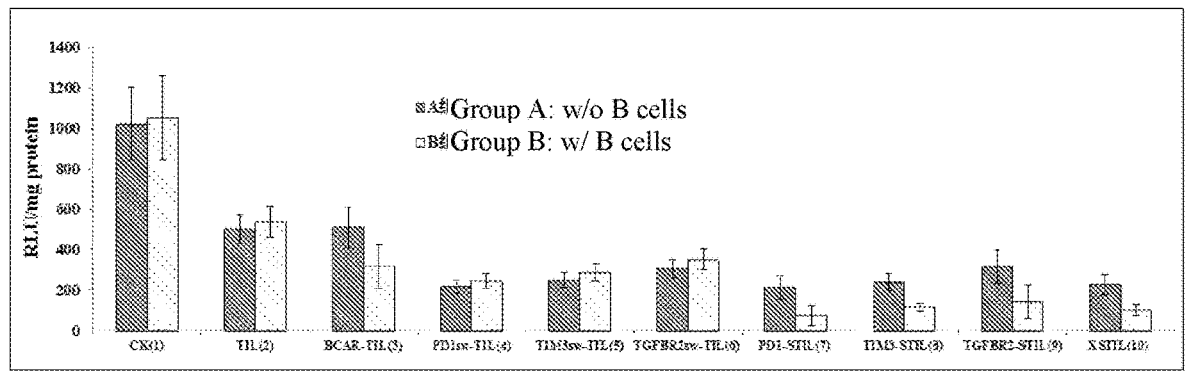
FIGS. 17A and 17B illustrate tumor killing effect (a) and in vitro expansion (b) of different TILs in the absence (Group A) or presence (Group B) of B cells.
Figure 17B:
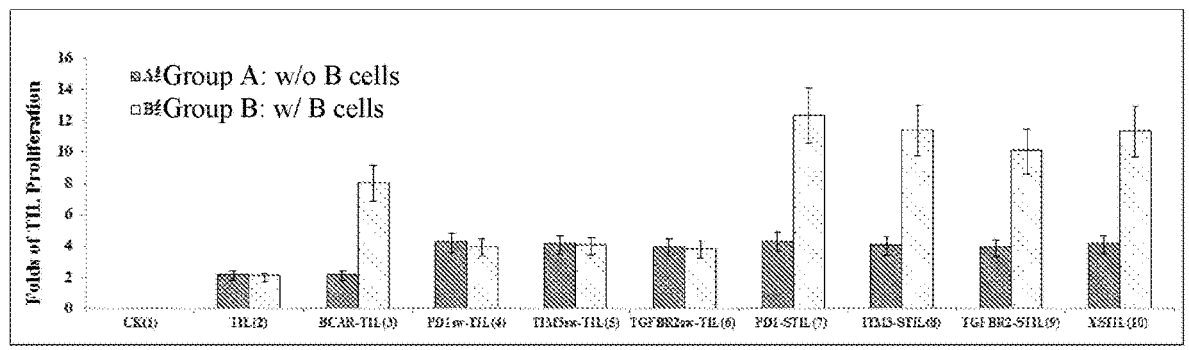

Tumor cells are isolated from a patient's fresh tumor tissues and seeded into 24-well plate together with luciferase marker. The cells were cultured overnight allowing adherence. The cells are divided into 10 groups and are co-cultured with control or T cells according to the following: Control group, with no addition of T cells-CK (Group A1); Normal TIL (Group A2); BCAR-TIL (Group A3); PD1sw-TIL (Group A4); TIM3sw-TIL (Group A5); TGFBR2sw-TIL (Group A6); PD1-STIL (Group A7); TIM3-STIL (Group A8); TGFBR2-STIL (Group A9); and XSTIL (Group A10). The following assays are conducted:

1. Secretion of cytokines by T cells. Secretion of IFN-γ and IL-2 is measured for each group with ELISA after coculture with tumor cells for 24 hours. As shown in FIGS. 16A and 16B, there is no IFN-γ or IL-2 secretion observed in control Group A1, while the IFN-γ or IL-2 secretion is observed in all the other groups (Group A2-A10). Of all the groups, those with Switch (Groups A4-A10) exhibit a higher secretion of IFN-γ or IL-2 over the groups without the Switch (Groups A2 and A3).
2. Growth of tumor cells. Supernatant is removed from the culture after 48 h and 96 h. The culture is then rinsed with PBS 3 times. The adherent tumor cells are lysed, and luciferase activity is measured to determine an amount of protein as an indication of the survival rate of tumor cells. As shown in FIG. 17A, the number of tumor cells in each group (Groups A2-A10) is reduced compared with the control group (Group A1), and the groups with the Switch (Groups A4-A10) show more significant reduction in the number of tumor cells than the groups without the Switch (Groups A2 and A3).
3. Expansion of T cells. The number of T cells is counted after culture for 48 h. As shown in FIG. 17B, T cells of those groups without the Switch (Groups A2-A3) show slight expansion while the group with the Switch (Groups A4-A10) show remarkable expansion.

(2) Tumor Killing Comparison in the Presence of B Cells

Tumor cells and TILs are isolated from a patient's fresh tumor tissues and the tumor cells are seeded into 24-well plate together with luciferase marker before cultured overnight allowing adherence. To each well the same amount of B cells are added. The cultured cells are divided into 10 groups and are co-cultured with control or T cells according to the following: Control group, with no addition of T cells-CK (Group B1); Normal TIL (Group B2); BCAR-TIL (Group B3); PD1sw-TIL (Group B4); TIM3sw-TIL (Group B5); TGFBR2sw-TIL (Group B6); PD1-STIL (Group B7); TIM3-STIL (Group B8); TGFBR2-STIL (Group B9); and XSTIL (Group B10). The following assays are conducted:

1. Growth of tumor cells. Supernatant is removed from the culture after 48 h and 96 h. The culture is then rinsed with PBS 3 times. The adherent tumor cells are lysed, and luciferase activity is measured as an indication of the survival rate of tumor cells. As shown by FIG. 17A, the number of tumor cells in each group (Groups B2-B10) is reduced compared with the control group (Group B1), and the Normal TIL group (Group B2) has the least tumor cell reduction compared to the significant reduction achieved by all the other groups (Groups B3-B10).
2. Expansion of T cells. The number of T cells is counted after culture for 48 h. As shown in FIG. 17B, Normal TIL group (Group B2) shows slight expansion, while T cells of those groups with the Switch (Groups B4-B10) show remarkable expansion, with the groups having BCAR (Groups B3 and B7-B10) showing even more expansion.

As shown by the in vitro assay, TILs' tumor killing effect is improved after being transduced with the Switch molecule. When transduced with both the Switch and BCAR molecules to provide SuperTILs, the SuperTILs yield even stronger expansion and tumor cell-killing effect in the presence of B cells.

Example 22: In Vitro Assay on Super-pTIL Efficacy

In order to confirm the Super-pTILs' efficacy, the similar experiments are conducted as for SuperTILs (see Example 21).

(1) Comparison of Tumor Killing Effect when No B Cells are Added.

Figure 18A:
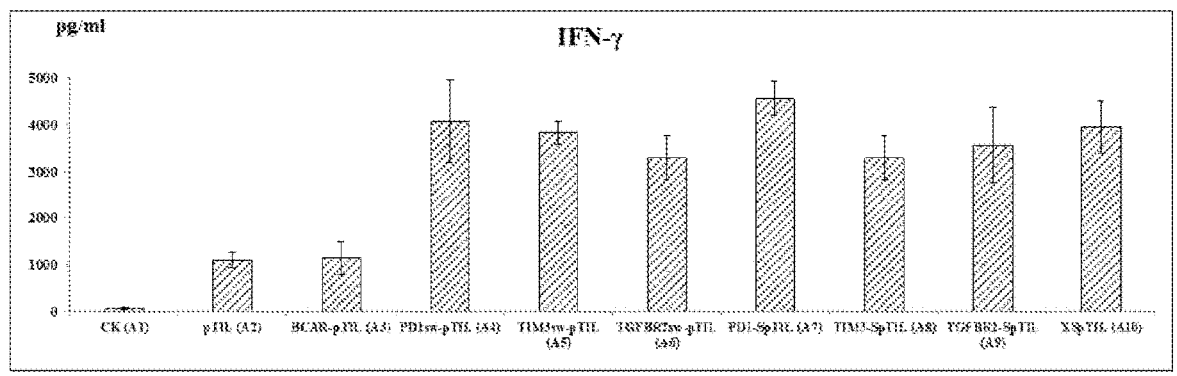
FIGS. 18A and 18B illustrates release of IFN-γ and IL-2 from different TILs without B cells.
Figure 18B:
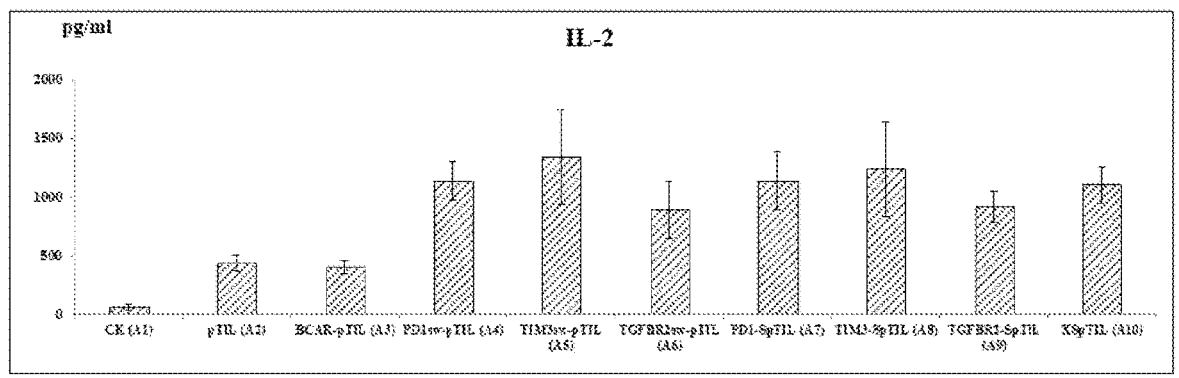
Figure 19A:
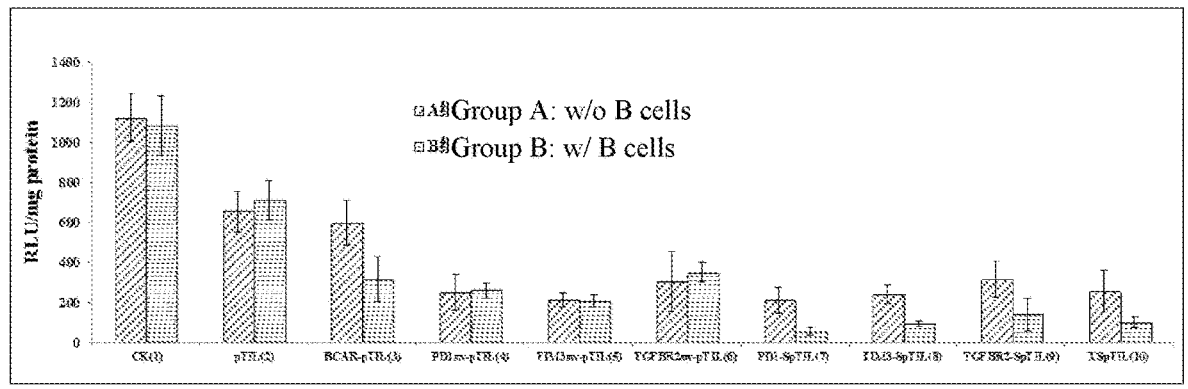
FIGS. 19A and 19B illustrate tumor killing effect (a) and in vitro expansion (b) of different pTILs in the absence (Group A) or presence (Group B) of B cells.

The groups are: Control group, with no addition of T cells-CK (Group A1); Normal pTIL (Group A2); BCAR-pTIL (Group A3); PD1sw-pTIL (Group A4); TIM3sw-pTIL (Group A5); TGFBR2sw-pTIL (Group A6); PD1-SpTIL (Group A7); TIM3-SpTIL (Group A8); TGFBR2-SpTIL (Group A9); and XSpTIL (Group A10). The following assays are conducted:

1. Secretion of cytokines by T cells. As shown in FIGS. 18A and 18B, there is no IFN-γ or IL-2 secretion observed in control Group A1, while the IFN-γ or IL-2 secretion is observed in all the other groups (Group A2-A10). Of all the groups, those with Switch (Groups A4-A10) exhibit a higher secretion of IFN-γ or IL-2 over the groups without the Switch (Groups A2 and A3).
2. Growth of tumor cells. As shown by FIG. 19A, the number of tumor cells in each group (Groups A2-A10) is reduced compared with the control group (Group A1), and the groups with the Switch (Groups A4-A10) show more significant reduction in the number of tumor cells.

Figure 19B:
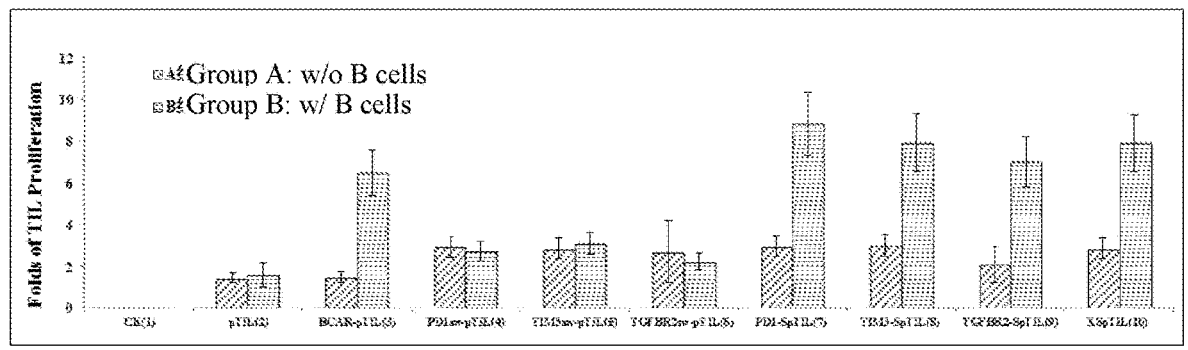

3. Expansion of T cells. The number of T cells are counted after culture for 48 h. As shown in FIG. 19B, T cells of those groups without the Switch (Groups A2-A3) show slight expansion while the group with the Switch (Groups A4-A10) show remarkable expansion.

(2) Tumor Killing Comparison in the Presence of B Cells

The groups are: Control group, with no addition of T cells-CK (Group B1); Normal pTIL (Group B2); BCAR-pTIL (Group B3); PD1sw-pTIL (Group B4); TIM3sw-pTIL (Group B5); TGFBR2sw-pTIL (Group B6); PD1-SpTIL (Group B7); TIM3-SpTIL (Group B8); TGFBR2-SpTIL (Group B9); and XSpTIL (Group B10). To each well the same amount of B cells are added. The following assays are conducted:

1. Growth of tumor cells. As shown by FIG. 19A, the number of tumor cells in each group (Groups B2-B10) are reduced compared with the control group (Group B1), and the Normal pTIL group (Group B2) has the least tumor cell reduction compared to the significant reduction achieved by all the other groups (Groups B3-B10).
2. Expansion of T cells. As shown in FIG. 19B, Normal pTIL group (Group B2) show slight expansion, while T cells of those groups with the Switch (Groups B4-B10) show remarkable expansion, with the groups having BCAR (Groups B3 and B7-B10) showing even more expansion.

As shown by the in vitro assay, pTILs' tumor killing effect is highly improved after being transduced with the Switch molecule. When transduced with both the Switch and BCAR to provide SuperTILs, the SuperTILs have even stronger expansion and tumor cell-killing effect in the presence of B cells.

Example 23: Animal Test on Super TILs

Animal Model: $1*10^6$ tumor cells from fresh tumor cells are subcutaneously injected to NSG mice. As blank control, animals of Group A0 are s.c injected with PBC. Tumors form in animals about two weeks after injection of tumor cells. Tumor size is measured at Day 25. 132 mice are selected and divided to Group A (11 subgroups) without B cells and Group B (11 subgroups) with B cells (22 groups in total) according to the following:

Group A consists of Blank control group (Group A0) injected with PBS via tail vein and 10 groups of mice inoculated with tumor cells: non-treatment-PBS group (Group A1); normal TIL (Group A2); BCAR-TIL (Group A3); PD1sw-TIL (Group A4); TIM3sw-TIL (Group A5); TGFBR2sw-TIL (Group A6); PD1-STIL (Group A7); TIM3-STIL (Group A8); TGFBR2-STIL (Group A9); and XSTIL (Group A10). Groups A2-A10 are given $1*10^4$ T cells via tail vein.

Group B consists of Blank control group (Group B0) injected with PBS via tail vein and 10 groups of mice inoculated with tumor cells: non-treatment-PBS group (Group B1); normal TIL (Group B2); BCAR-TIL (Group B3); PD1sw-TIL (Group B4); TIM3sw-TIL (Group B5); TGFBR2sw-TIL (Group B6); PD1-STIL (Group B7); TIM3-STIL (Group B8); TGFBR2-STIL (Group B9); and XSTIL (Group B10). Groups B2-B10 are given $1*10^4$ T cells via tail vein, and all groups were given $1*10^7$ B cells via infusion.

Tumor size and health status of the mice is measured every 2-3 days for 28 days after administration. Tumor size is calculated as:

Tumor size=½*long_diameter*short_diameter*short_diameter.

(1) Change in Tumor Burden

The experiment is expected to demonstrate that mice infused with TILs with Switch (Groups A4-A10 and B4-B6) exhibit delay tumor growth. The TILs with BCAR (Groups B3) are expected to highly expand in the presence of B cells, thereby yielding to a marked tumor growth delay effect.

(3) PD1, TIM3 and TFGBR2 Expression of Tumor Cells.

Tumor tissues from Groups B7-B9 are assayed before and after the tumors turn to increase again. Results are expected to show that: (i) Group B7 (PD1-STILs) tumors do not express PD1 but express TIM3 and TGFBR2; (ii) Group B8 (TIM3-STILs) tumors do not express TIM3 but express PD1 and TGFBR2; and (iii) Group B9 (TGFBR2-STILs) tumors do not express TGFBR2 but express PD1 and TIM3. In some cases, it may be possible for tumor microenvironment markers to escape, resulting in ineffectiveness of the corresponding Switch.

Example 24: Animal Test on Super-pTILs

In order to confirm the in vivo efficacy of Super-pTILs, animal test are designed similar to that for SuperTILs. Animals are also divided into Group A (in the absence of B cells) and Group B (in the presence of B cells), comprising 22 subgroups in total:

Group A consists of Blank control group (Group A0) injected with PBS via tail vein and 10 groups of mice inoculated with tumor cells: non-treatment-PBS group (Group A1); normal pTIL (Group A2); BCAR-pTIL (Group A3); PD1sw-pTIL (Group A4); TIM3sw-pTIL (Group A5); TGFBR2sw-pTIL (Group A6); PD1-SpTIL (Group A7); TIM3-SpTIL (Group A8); TGFBR2-SpTIL (Group A9); and XSpTIL (Group A10). Groups A2-A10 are given $1*10^4$ T cells via tail vein.

Group B consists of Blank control group (Group B0) injected with PBS via tail vein and 10 groups of mice inoculated with tumor cells: non-treatment-PBS group (Group B1); normal pTIL (Group B2); BCAR-pTIL (Group B3); PD1sw-pTIL (Group B4); TIM3sw-pTIL (Group B5); TGFBR2sw-pTIL (Group B6); PD1-SpTIL (Group B7); TIM3-SpTIL (Group B8); TGFBR2-SpTIL (Group B9); and XSpTIL (Group B10). Groups B2-B10 are given $1*10^4$ T cells via tail vein, and all groups are given $1*10^7$ B cells via infusion.

Tumor size and health status of the mice are measured every 2-3 days for 28 days after administration. Tumor size may be calculated as:

Tumor size=½*long_diameter*short_diameter*short_diameter.

The experiment is expected to demonstrate that Super-TILs/pTILs disclosed herein have specific tumor recognition and killing effect via multiple targets (from TILs or pTILs). The SuperTILs/pTILs may also exhibit the ability to overcome tumor environment to enhance killing (from one or more Switch), and self-expansion capability from BCAR. These modified immune cells provide an effective tumor therapy tool to address the various problems involved in tumor immune cell therapies.

Example 25: Killing Effect of BCAR-TCR T on NY ESO1 Tumor Cells In Vitro

To confirm the function of BCAR in TCR T targeting NY-ESO-1, tumor cell line J82-NY ESO1 with HLA genotype A: 0201 was used as target cells to measure the killing effect of BCAR-TCR T cells.

$1\times10^5$ J82-NY ESO1 tumor cells were seeded on the RTCA (Real Time Cell Analysis) electrode plate, and cultured overnight to allow adhesion. The cells were divided into three groups—A, B and C. In group A, $1\times10^5$, $1\times10^4$, $1\times10^3$, $1\times10^2$ BCAR-TCR T were co-cultured with J82-NY-ESO-1 cells, respectively. In group B, $1\times10^5$, $1\times10^4$, $1\times10^3$, $1\times10^2$ BCAR-TCR T together with $1\times10^5$ B cells were co-cultured with J82-NY-ESO-1 cells. Group C was blank control. RTCA system was used to record "Cell Index" every ten minutes for 24 hours.

Figure 20:
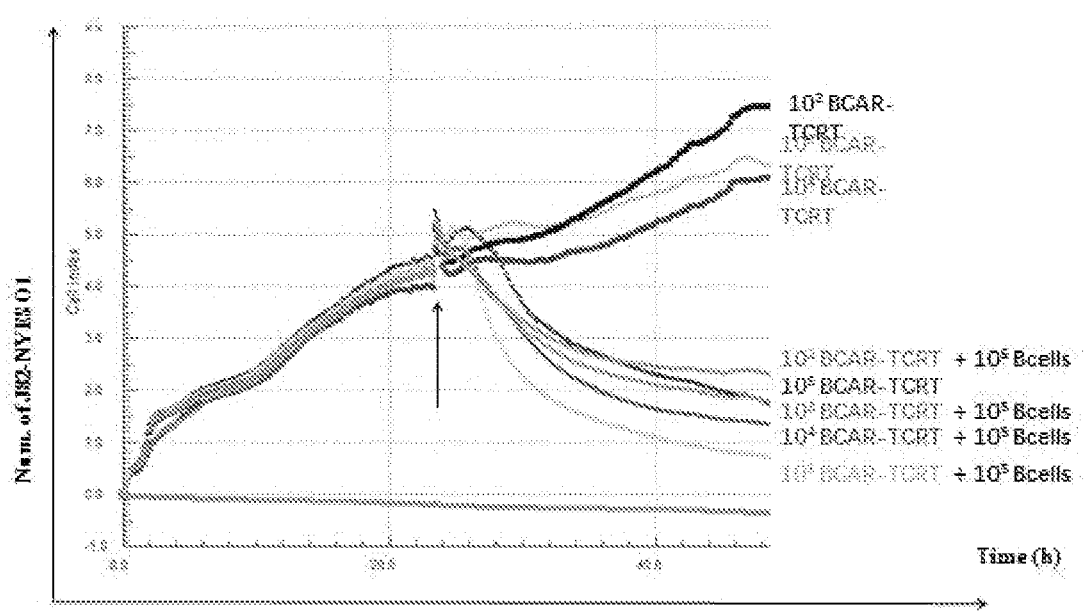
FIG. 20 illustrates the killing effect of BCAR-TCRT on J82-NY ESO1 tumor cells w/and w/o presence of B cells.
Figure 21A:
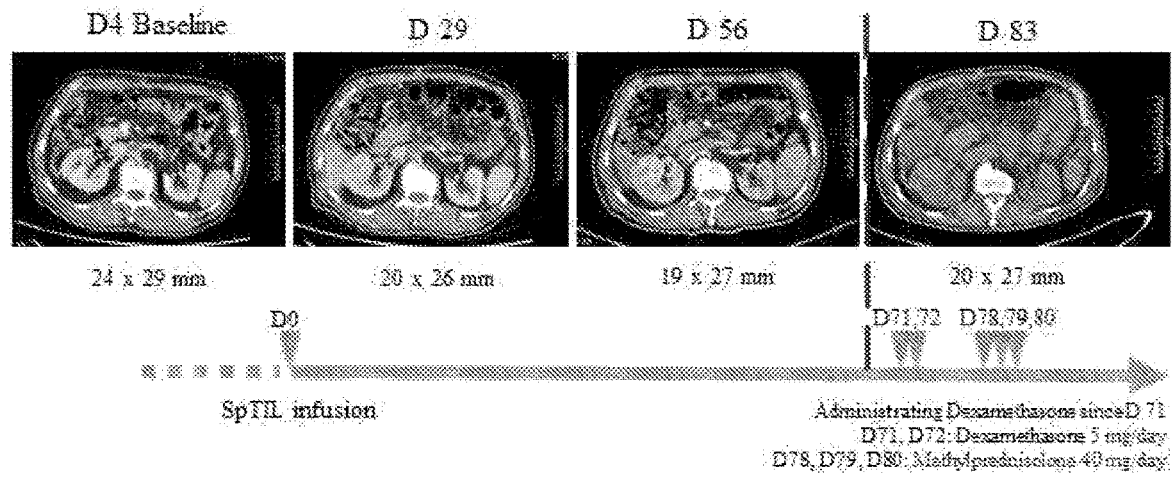
FIGS. 21A-D are tumor image analysis for Subjects 1-4.
Figure 21B:
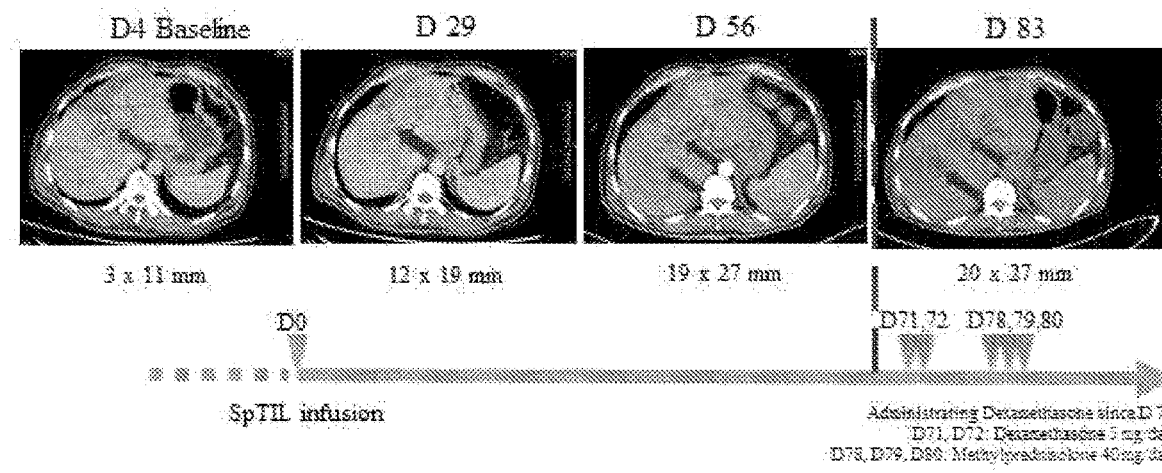
Figures 21C, 21D:
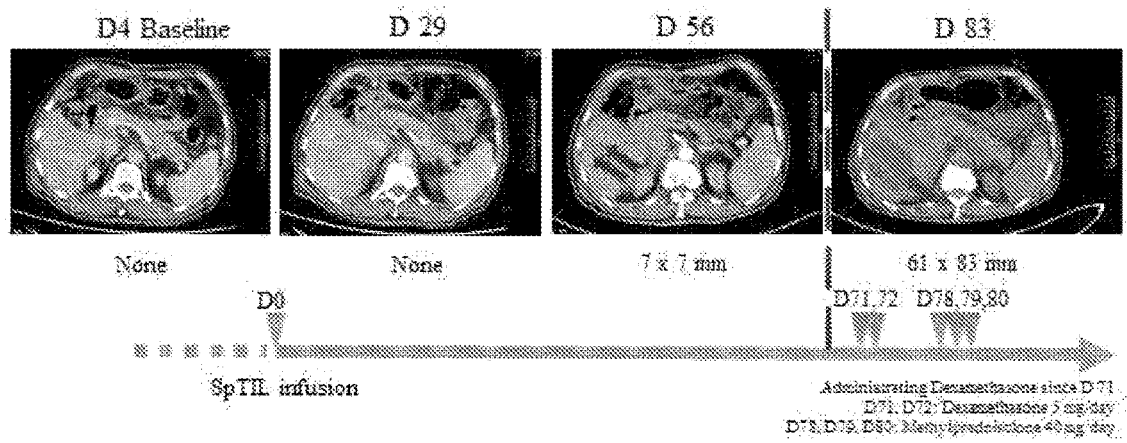
Figure 22A:
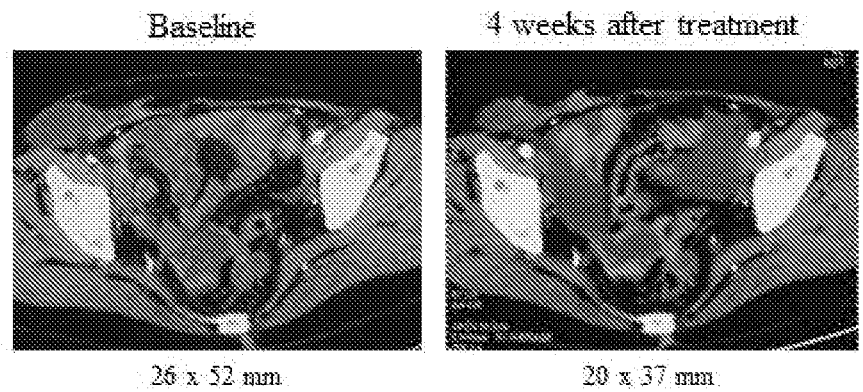
Figure 22B:
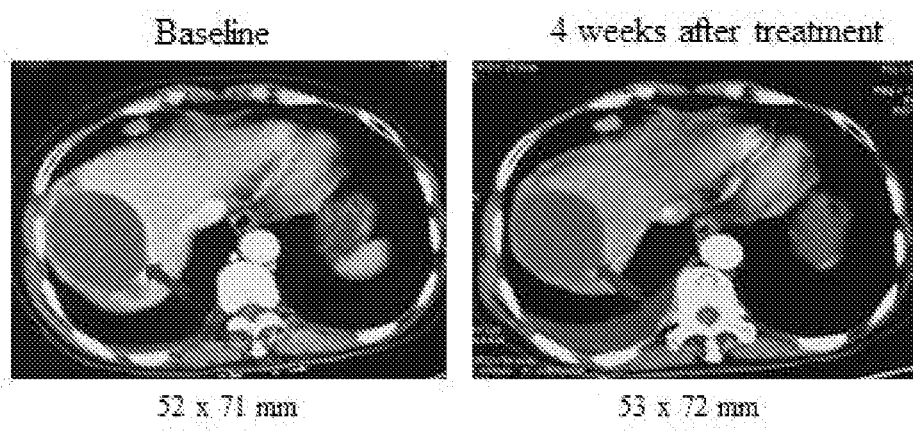
Figure 23A:
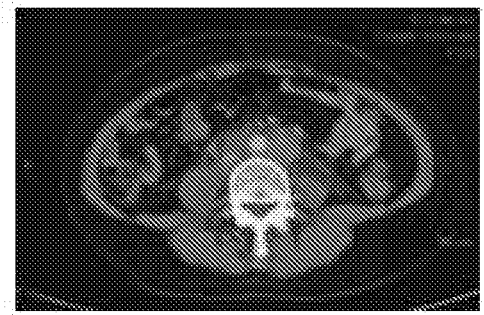
FIGS. 23A-D are tumor image analysis for Subjects 1-4.
Figure 23A:
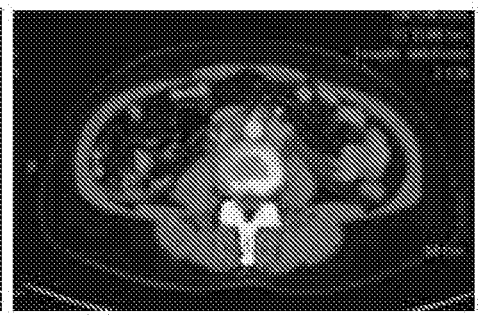
Figure 23B:
Figure 23B:
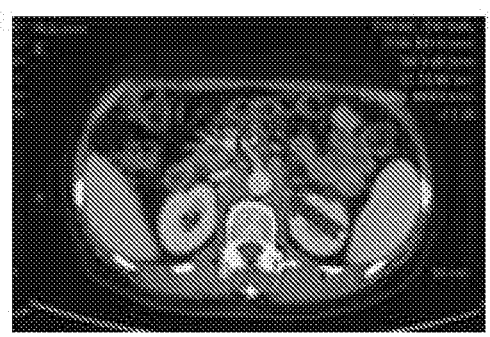
Figures 23C, 23D:
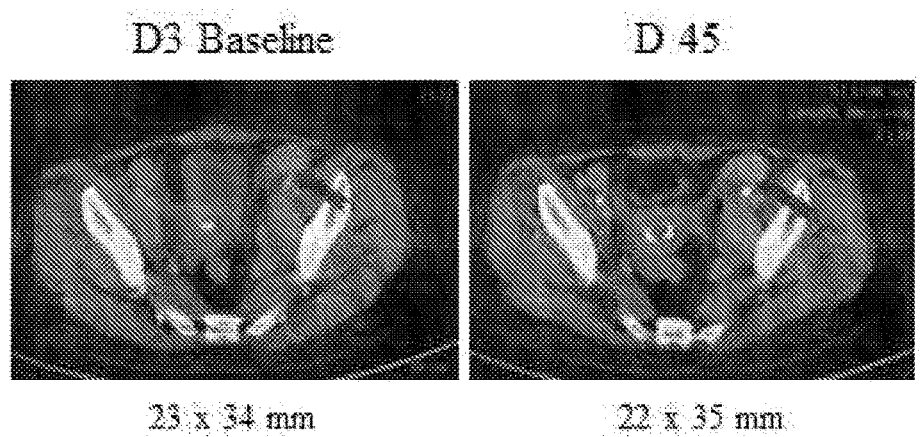

As shown in FIG. 20, in group A where B cell was absent, only the highest dose of $1\times10^5$ BCAR-TCR T showed significant killing effect on J82-NY ESO1 tumor cells, while in group B, in the presence of B cells, even the lowest dose of $1\times10^2$ BCAR-TCR T showed a significant killing effect on J82-NY ESO1 tumor cells that is comparable to that of $1\times10^5$ BCAR-TCR T dose in group A, indicating an increase of efficacy of about 1000 times.

Example 26. Clinical Anti-Tumor Effects of STILs and SpTILs

Five subjects were enrolled and infused with STILs or SpTILs in a clinical trial (as shown in Table 1):

out of the five subjects (60%) developed TP53 mutation which is resistant to targeted therapy and has a poor prognosis. TMB assessment and HLA polymorphism indicated that all these subjects were less likely to be benefited from PD1/PDL1 monoclonal antibody therapy or conventional neoantigen therapy.

Cell Preparation Before Treatment
(1) Isolation of TILs/pTILs

For subject No. 3, 4, and 5, CD3 positive TILs were isolated from newly excised tumor tissues with CD3 magnetic beads after enzymatic digestion. For subject No. 1 and 2, PBMC was isolated from the patients, wherein PD1+ T cells amount to 19% and 5% of the total T cells, respectively. Such a high ratio of PD1V T cells was considered as TILs in the peripheral blood (pTILs) originating from tumor tissues, and was further concentrated with PD1 magnetic beads to provide PD1V T cells, i.e., pTILs Preparation of STILs/SpTILs The lentivirus vector loaded with PD1sw-CD19 CAR was transfected into TILs/pTILs at transfection efficiencies of 2% to 15%. The cells were packaged into infusion bags without expansion. The whole process took place in three to ten days (excluding the identification process of T cells recognizing neoantigen).

TABLE 1

| # | Sex | Age | Primary cancer | Metastatic sites | Num. of metastatic lesions | Treatment history | Mutation hotspot | HLA polymorphism | Mutations/Mb | TMB* |
|---|---|---|---|---|---|---|---|---|---|---|
| 1 | M | 54 | Gallbladder cancer | Liver, retroperitoneal lymph nodes | >2 | Auxiliary treatment failed | TP53 | | 7.8 | Medium |
| 2 | F | 54 | Ovarian cancer | Peritoneum/abdominal wall, inguinal/abdominal lymph nodes | >2 | Three lines of treatments all failed | APC; RB1; TP53; BRCA1 | | 4.4 | Low |
| 3 | F | 55 | Melanoma | Inguinal/pelvic/peritoneal lymph nodes multiple metastases | >2 | Three lines of treatments all failed | BRAF V600E | Type A homozygous | 6.6 | Medium |
| 4 | F | 24 | Colon cancer | Bilateral lungs multiple metastases | >2 | Three lines of treatments all failed | KRAS; TP53; SMAD4 | Type B, C homozygous | 4.9 | Low |
| 5 | M | 42 | Clear cell renal cell cancer | Bilateral lungs, multiple bones and subcutaneous | >2 | Two lines of treatments failed | | | 3.3 | Low |

*Note:
Tumor MutationBurden (TMB) was assessed by the number of mutations per million bases in the genome. TMB < 5 is regarded as low mutation burden, 5-10 is medium mutation burden, and ≥ 10 is high mutation burden. It is believed that subjects with higher TMB are less likely to be benefited from PD1 monoclonal antibody and neoantigen immunotherapy.

As shown in Table 1, the enrolled subjects had different solid tumors but all of them are in late stage, refractory and highly progressive with more than two distant metastatic lesions. Multiple-lines of treatments were ineffective. Three Treatment with the resulted cells is shown in Table 2 for all the five subjects, at doses in the magnitude of $10^5$~$10^6$ cells/kg, which are much lower than reported doses at $10^8$-$10^9$ cells/kg.

TABLE 2

| Subject No. | Subject ID. | Type of tumor | Infused cell type | Total infused cell number | Body weight of the subject | Cell number/kg body weight |
|---|---|---|---|---|---|---|
| 1 | DNA-CQHA | Gallbladder cancer | SpTILs | $5.05 \times 10^5$ | 64 kg | $7.89 \times 10^3$ |
| 2 | LCA-GZQU | Ovarian cancer | SpTILs | $9.80 \times 10^4$ | 48 kg | $2.04 \times 10^3$ |
| 3 | HSSL-LHFA | Melanoma | STILs | $3.26 \times 10^6$ | 60 kg | $5.43 \times 10^4$ |

TABLE 2-continued

| Subject No. | Subject ID. | Type of tumor | Infused cell type | Total infused cell number | Body weight of the subject | Cell number/kg body weight |
|---|---|---|---|---|---|---|
| 4 | JCA-CHYU | Colon cancer | STILs | $9.45 \times 10^6$ | 60 kg | $1.58 \times 10^5$ |
| 5 | SA-ZHRU | Clear cell renal cell cancer | STILs | $3.36 \times 10^6$ | 52 kg | $6.46 \times 10^4$ |

Safety Assessment

Of the 5 subjects, 3 were observed with grade 1 Cytokine Release Syndrome (CRS), evidenced by high fever, with an incidence of 60% (3/5). All of the three were relieved, 1 without intervention and the other two treated with tocilizumab. Both the incidence and grading of CRS are much lower than those in CD19 CAR-T treatment. No post-treatment autoimmune disease observed.

Efficacy Evaluation

Efficacy of the cell infusion treatment was verified by tumor imaging (FIGS. 21A-D; FIGS. 22A-D; FIGS. 23A-D; and FIGS. 24A-C for subjects Nos. 1-4, respectively). The results are summarized below in Table 3.

TABLE 4

| Subject No. | Effective cell number infused | Effective cell number in peripheral blood on Day 14 | Expansion folds | B cell reduction |
|---|---|---|---|---|
| 1 | $5.05 \times 10^5$ | $7.07 \times 10^7$ | 140 | 75% |
| 2 | $9.80 \times 10^4$ | $7.39 \times 10^7$ | 754 | 92% |
| 3 | $3.26 \times 10^6$ | $4.01 \times 10^8$ | 125 | 88% |
| 4 | $9.45 \times 10^6$ | $6.00 \times 10^8$ | 63 | 94% |

TABLE 3

| | Before treatment | | | After treatment | |
|---|---|---|---|---|---|
| No. | Primary Cancer | Metastatic sites | Num of metastatic lesions | Efficacy within 60 days* | Notes |
| 1 | Gallbladder cancer | Liver, retroperitoneal lymph nodes | >2 | PD | Progression stabilized from Day 0 to Day 56, with only slow progression or false progression. |
| 2 | Ovarian cancer | Peritoneum/abdominal wall, inguinal/abdominal lymph nodes | >2 | SD | Abdominal wall subcutaneous metastatic lesions reduced significantly. |
| 3 | Melanoma | Inguinal/pelvic/peritoneal lymph nodes multiple metastases | >2 | PR | Multiple lesions reduced signifficantly. |
| 4 | Colon cancer | Bilateral lungs multiple metastases | >2 | SD | Disease progression significantly suppressed; and mental state improved significantly according to patient. |
| 5 | Clear cell renal cell cancer | Bilateral lungs, multiple bones and subcutaneous | >2 | SD | Disease progression significantly suppressed; and subcutaneous mass on back shrinked according to patient |

*Note:
Efficacy evaluation was performed under the RECIST criteria.

Effect of CAR on Expansion of STILs/SpTILs In Vivo

The ratio of CAR+ T cells in peripheral blood of the subjects was monitored. The folds STILs (or SpTILs) expanded in peripheral blood was calculated by the following formula:

Expansion Folds=lymphocyte count/L*circulating blood volume*T cell ratio in lymphocytes*STIL ratio in T cells.

wherein lymphocyte count/L was obtained from routine blood test; T cell ratio in lymphocytes was obtained by flow cytometry as the ratio of CD3+ cells; the STIL ratio in T cells was determined by flow cytometry as the ratio of CAR+ cells in CD3+ cells.

STIL/SpTIL expansion was calculated and B cell reduction determined on Day 14. Results are shown in Table 4.

No exogenous immunoglobulin was administered during the observation, and no immunodeficiency observed for any of the subjects.

Bispecific Recognition of STILs and SpTILs

Figure 25:
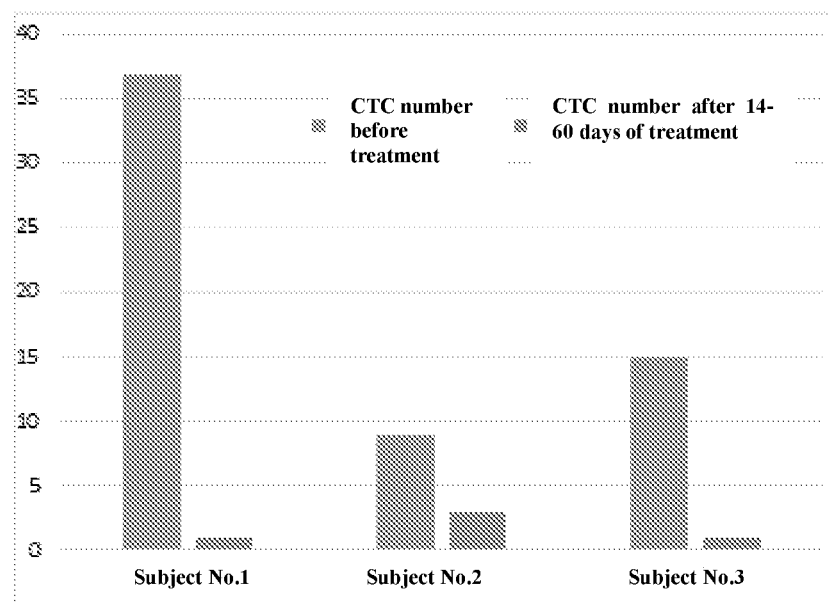
FIG. 25 illustrates change of Circulating Tumor Cell (CTC) numbers in peripheral blood after infusion of STILs or SpTILs.

Subjects 1, 2, and 4 were monitored for their circulating tumor cells (CTC) in peripheral blood. Then CTC numbers at two months after cell infusion was compared with the baseline on the infusion day. The results are provided below in Table 5 and FIG. 25, showing significantly decreased CTC numbers.

TABLE 5

| Subject No. | CTC number/5 mL (Baseline) | CTC number/5 mL (60 days treatment) | % reduction |
|---|---|---|---|
| 1 | 37 | 1 | 97% |
| 2 | 9 | 3 | 67% |
| 4 | 15 | 1 | 93% |

Enhance Killing Effect by the Switch Molecule

Three subjects (No. 1, 2, and 5) were observed to have reduced peripheral blood T cells during Day 4 to Day 28 and persistent pleural effusion or ascites. Subject 4 with pleural metastasis developed pleural effusion, while subjects 1 and 2 with peritoneal metastasis developed ascites. In both the pleural effusion and the ascites, T cells were found, together with higher concentration of IL6 than in the peripheral blood. The observation is summarized in Table 6, indicating that killing effect of the STILs/SpTILs was enhanced by the switch molecule.

TABLE 6

| Subject No. | Primary Cancer | Metastatic sites | Number of metastatic lesions | Pleural effusion or ascites | IL6 Conc. in peripheral blood (pg/L) | IL6 Conc. in pleural effusion or ascites (pg/L) |
|---|---|---|---|---|---|---|
| 1 | Gallbladder cancer | Liver, retroperitoneal lymph node | >2 | Ascites | 1074 | 3075 |
| 2 | Ovarian cancer | Peritoneum/abdominal, inguinal/abdominal lymph nodes | >2 | Ascites | 2000 | 22500 |
| 4 | Colon cancer | Bilateral lungs multiple metastasis | >2 | Pleural effusion | 200 | 15000 |

TABLE 7

Sequences

| SEQ ID NO: | Sequence |
|---|---|
| 1 | MGWSCIILFLVATATGVHSAIQLTQSPSSLSASVGDRVTITCRASQGISSALAWYQQ KPGKAPKLLIYDASSLESGVPSRFSGSGSGTDFTLTISSLQPEDFATYYCQQFNSYPY TFGQGTKLEIKGGGGSGGGGSGGGGSEVQLVQSGAEVKKPGESLKISCKGSGYSFS SSWIGWVRQMPGKGLEWMGITYPDDSDTRYSPSFQGQVTISADKSIRTAYLQWSSL KASDTAMYYCARHVTMIWGVIIDFWGQGTLVTVSSAAA |
| 2 | MQIPQAPWPVVWAVLQLGWRPGWFLDSPDRPWNPPTFSPALLVVTEGDNATFTCS FSNTSESFVLNWYRMSPSNQTDKLAAFPEDRSQPGQDCRFRVTQLPNGRDFHMSVV RARRNDSGTYLCGAISLAPKAQIKESLRAELRVTERRAEVPTAHCPSPLFPGPSKPF WVLVVVGGVLACYSLLVTVAFIIFWVRSKRSRLLHSDYMNMTPRRPGPTRKHYQP YAPPRDFAAYRS |
| 3 | MFSHLPFDCVLLLLLLLLTRSSEVEYRAEVGQNAYLPCFYTPAAPGNLVPVCWGKG ACPVFECGNVVLRTDERDVNYWTSRYWLNGDFRKGDVSLTIENVTLADSGIYCCRI QIPGIMNDEKFNLKLVIKPAKVTPAPTRQRDFTAAFPRMLTTRGHGPAETQTLGSLP DINLTQISTLANELRDSRLANDLRDSGATIRICPSPLFPGPSKPFWVLVVVGGVLACY SLLVTVAFIIFWVRSKRSRLLHSDYMNMTPRRPGPTRKHYQPYAPPRDFAAYRS |
| 4 | MGRGLLRGLWPLHIVLWTRIASTIPPHVQKSDVEMEAQKDEIICPSCNRTAHPLRHI NNDMIVTDNNGAVKFPQLCKFCDVRFSTCDNQKSCMSNCSITSICEKPQEVCVAVW RKNDENITLETVCHDPKLPYHDFILEDAASPKCIMKEKKKPGETFFMCScSSDECND NIIFSEEYNTSNPDLLLVIFQCPSPLFPGPSKPFWVLVVVGGVLACYSLLVTVAFIIFW VRSKRSRLLHSDYMNMTPRRPGPTRKHYQPYAPPRDFAAYRS |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An isolated population of modified immune cells comprising modified immune cells that specifically binds to a tumor antigen,
wherein each modified immune cell comprises
a peripheral blood mononuclear cell (PBMC) expressing both
endogenous PD1 and
a chimeric stimulating molecule or a switch molecule, wherein said chimeric stimulating molecule or a switch molecule comprises:
an extracellular domain (ECD) of a protein that, in an unmodified immune cell, elicits an immune cell inactivation signal upon binding to its ligand, wherein said ECD is fused to an intracellular domain (ICD) of a co-stimulatory molecule that mediates an immune cell activation signal,
wherein binding of the chimeric stimulating molecule or the switch molecule to the ligand yields said immune cell activation signal in said modified immune cell instead of said immune cell inactivation signal and
wherein the isolated population comprises a higher concentration of PBMCs endogenously expressing PD1 compared to a population of PBMCs in a subject.

2. The isolated population of modified immune cell of claim 1, wherein said antigen is a neoantigen.

3. The isolated population of modified immune cell of claim 2, wherein each modified immune cell further expresses a T cell receptor (TCR) complex exhibiting specific binding to said neoantigen.

4. The isolated population of modified immune cell of claim 3, wherein said TCR complex is an endogenous TCR complex.

5. The isolated population of modified immune cell of claim 3, wherein said TCR complex is an exogenous TCR complex.

6. The isolated population of modified immune cell of claim 2, wherein the neoantigen comprises a peptide fragment of a protein encoded by a mutated gene, wherein the gene is selected from ABL1, ACO1 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, and XPOT.

7. The isolated population of modified immune cell of claim 2, wherein the neoantigen is selected based on a somatic mutation profile of a tumor sample from an individual.

8. The isolated population of modified immune cell of claim 1, wherein said protein that, in an unmodified immune cell, elicits an immune cell inactivation signal upon binding to its ligand is a checkpoint receptor, a cytokine receptor, a chemokine receptor, a growth factor receptor, or a hormone receptor.

9. The isolated population of modified immune cell of claim 1, wherein said protein that, in an unmodified immune cell, elicits an immune cell inactivation signal upon binding to its ligand is selected from the group consisting of transforming growth factor-beta receptor (TGF-beta-R), programmed cell death 1 (PD-1), cytotoxic T-lymphocyte associated protein 4 (CTLA-4), B and T lymphocyte attenuator (BTLA), a killer immunoglobulin-like receptor (KIR), indoleamine 2,3-dioxygenase (IDO), lymphocyte activation gene-3 (LAG3), T cell immunoglobulin mucin 3 (TIM-3), and TIGIT.

10. The isolated population of modified immune cell of claim 1, wherein said co-stimulatory molecule is interleukin-2 receptor (IL-2R), interleukin-12 receptor (IL-12R), CD2, CD3, CD4, CD7, CD8, CD27, CD28, CD30, CD40, 4-1BB/CD137, ICOS, lymphocyte function-associated antigen-1 (LFA-1), LIGHT, NKG2C, or OX40.

11. The isolated population of modified immune cell of claim 1, wherein the switch molecule comprises an amino acid sequence of SEQ ID NO: 2, SEQ ID NO: 3 or SEQ ID NO: 4.

12. The isolated population of modified immune cell of claim 1, wherein each modified immune cell further expresses a chimeric antigen receptor comprising (i) an antigen interacting domain capable of binding a B cell surface protein; (ii) a transmembrane domain; and (iii) an intracellular signaling domain.

13. The isolated population of modified immune cell of claim 12, wherein said B cell surface protein is selected from CD19, CD20, and CD22.

14. The isolated population of modified immune cell of claim 12, wherein the antigen interacting domain capable of binding a B cell surface protein comprises an amino acid sequence of SEQ ID NO: 1.

* * * * *

SEQUENCE LISTING

<160> NUMBER OF SEQ ID NOS: 4

<210> SEQ ID NO 1
<211> LENGTH: 243
<212> TYPE: PRT
<213> ORGANISM: Artificial Sequence
<220> FEATURE:
<223> OTHER INFORMATION: Antigen binding domain targeting CD19

<400> SEQUENCE: 1

Asp Ile Val Leu Thr Gln Ser Pro Ala Ser Leu Ala Met Ser Leu Gln
1               5                   10                  15

Leu Gly Trp Arg Pro Gly Trp Phe Leu Asp Ser Pro Asp Arg Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Asp
65                  70                  75                  80

Pro Val Glu Glu Asp Asp Val Ala Ile Tyr Ser Cys Leu Gln Ser Arg
                85                  90                  95

Ile Phe Pro Arg Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Ile
        115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Thr Phe Thr Asp Tyr Ser Ile
145                 150                 155                 160

Asn Trp Val Lys Arg Ala Pro Gly Lys Gly Leu Lys Trp Met Gly Trp
                165                 170                 175

Ile Asn Thr Glu Thr Arg Glu Pro Ala Tyr Ala Tyr Asp Phe Arg Gly
            180                 185                 190

Arg Phe Ala Phe Ser Leu Glu Thr Ser Ala Ser Thr Ala Tyr Leu Gln
        195                 200                 205

Ile Asn Asn Leu Lys Tyr Glu Asp Thr Ala Thr Tyr Phe Cys Ala Leu
    210                 215                 220

Asp Tyr Ser Tyr Ala Met Asp Tyr Trp Gly Gln Gly Thr Ser Val Thr
225                 230                 235                 240

Val Ser Ser

<210> SEQ ID NO 2
<211> LENGTH: 235
<212> TYPE: PRT
<213> ORGANISM: Artificial Sequence
<220> FEATURE:
<223> OTHER INFORMATION: PD1/CD28 switch molecule

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val

```
            50                  55                  60
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Cys Pro Ser Pro Leu
145                 150                 155                 160

Phe Pro Gly Pro Ser Lys Pro Phe Trp Val Leu Val Val Val Gly Gly
                165                 170                 175

Val Leu Ala Cys Tyr Ser Leu Leu Val Thr Val Ala Phe Ile Ile Phe
            180                 185                 190

Trp Val Arg Ser Lys Arg Ser Arg Leu Leu His Ser Asp Tyr Met Asn
            195                 200                 205

Met Thr Pro Arg Arg Pro Gly Pro Thr Arg Lys His Tyr Gln Pro Tyr
210                 215                 220

Ala Pro Pro Arg Asp Phe Ala Ala Tyr Arg Ser
225                 230                 235

<210> SEQ ID NO 3
<211> LENGTH: 281
<212> TYPE: PRT
<213> ORGANISM: Artificial Sequence
<220> FEATURE:
<223> OTHER INFORMATION: TIM3/CD28 switch molecule

<400> SEQUENCE: 3

Met Phe Ser His Leu Pro Phe Asp Cys Val Leu Leu Leu Leu Leu Leu
  1               5                  10                  15

Leu Leu Thr Arg Ser Ser Glu Val Glu Tyr Arg Ala Glu Val Gly Gln
             20                  25                  30

Asn Ala Tyr Leu Pro Cys Phe Tyr Thr Pro Ala Ala Pro Gly Asn Leu
             35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
             85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
            130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
            165                 170                 175

Ser Thr Leu Ala Asn Glu Leu Arg Asp Ser Arg Leu Ala Asn Asp Leu
```

```
                180                 185                 190
Arg Asp Ser Gly Ala Thr Ile Arg Ile Cys Pro Ser Pro Leu Phe Pro
            195                 200                 205

Gly Pro Ser Lys Pro Phe Trp Val Leu Val Val Gly Gly Val Leu
    210                 215                 220

Ala Cys Tyr Ser Leu Leu Val Thr Val Ala Phe Ile Ile Phe Trp Val
225                 230                 235                 240

Arg Ser Lys Arg Ser Arg Leu Leu His Ser Asp Tyr Met Asn Met Thr
            245                 250                 255

Pro Arg Arg Pro Gly Pro Thr Arg Lys His Tyr Gln Pro Tyr Ala Pro
            260                 265                 270

Pro Arg Asp Phe Ala Ala Tyr Arg Ser
            275                 280

<210> SEQ ID NO 4
<211> LENGTH: 271
<212> TYPE: PRT
<213> ORGANISM: Artificial Sequence
<220> FEATURE:
<223> OTHER INFORMATION: TGFBR2/CD28 switch molecule

<400> SEQUENCE: 4

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
            85                  90                  95

Ser Ile Thr Ser Ile Cys Glu Lys Pro Gln Glu Val Cys Val Ala Val
        100                 105                 110

Trp Arg Lys Asn Asp Glu Asn Ile Thr Leu Glu Thr Val Cys His Asp
    115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
            165                 170                 175

Glu Tyr Asn Thr Ser Asn Pro Asp Leu Leu Leu Val Ile Phe Gln Cys
        180                 185                 190

Pro Ser Pro Leu Phe Pro Gly Pro Ser Lys Pro Phe Trp Val Leu Val
    195                 200                 205

Val Val Gly Gly Val Leu Ala Cys Tyr Ser Leu Leu Val Thr Val Ala
    210                 215                 220
```

| | | | | | | | | | | | | | |
|---|---|---|---|---|---|---|---|---|---|---|---|---|---|
| Phe | Ile | Ile | Phe | Trp | Val | Arg | Ser | Lys | Arg | Ser | Arg | Leu | Leu | His | Ser |
| 225 | | | | | 230 | | | | 235 | | | | | | 240 |
| Asp | Tyr | Met | Asn | Met | Thr | Pro | Arg | Arg | Pro | Gly | Pro | Thr | Arg | Lys | His |
| | | | | 245 | | | | | 250 | | | | | 255 | |
| Tyr | Gln | Pro | Tyr | Ala | Pro | Pro | Arg | Asp | Phe | Ala | Ala | Tyr | Arg | Ser | |
| | | | 260 | | | | | 265 | | | | | 270 | | |